US009808018B2

(12) United States Patent
De Jong et al.

(10) Patent No.: US 9,808,018 B2
(45) Date of Patent: Nov. 7, 2017

(54) ALPHA-AMYLASE VARIANTS

(71) Applicant: DSM IP ASSETS B.V., Heerlen (NL)

(72) Inventors: Rene Marcel De Jong, Echt (NL);
Hanna Elisabet Abbas, Echt (NL);
Evert Tjeerd Van Rij, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 42 days.

(21) Appl. No.: 14/767,406

(22) PCT Filed: Feb. 27, 2014

(86) PCT No.: PCT/EP2014/053853
§ 371 (c)(1),
(2) Date: Aug. 12, 2015

(87) PCT Pub. No.: WO2014/131842
PCT Pub. Date: Sep. 4, 2014

(65) Prior Publication Data
US 2015/0376588 A1      Dec. 31, 2015

Related U.S. Application Data

(63) Continuation of application No. 13/842,344, filed on Mar. 15, 2013, now Pat. No. 9,301,533.

(60) Provisional application No. 61/771,676, filed on Mar. 1, 2013.

(30) Foreign Application Priority Data

Mar. 1, 2013   (EP) ..................................... 13157398
Sep. 5, 2013   (EP) ..................................... 13183144

(51) Int. Cl.
*C12N 9/28*       (2006.01)
*A21D 8/04*       (2006.01)

(52) U.S. Cl.
CPC ........... *A21D 8/042* (2013.01); *C12N 9/2417* (2013.01); *C12Y 302/01001* (2013.01)

(58) Field of Classification Search
CPC .................................................. C12N 9/2417
USPC ......................................................... 435/202
See application file for complete search history.

(56) References Cited

U.S. PATENT DOCUMENTS

| 4,598,048 A | 7/1986 | Diderichsen et al. |
| 4,604,355 A | 8/1986 | Outtrup |
| RE38,507 E | 4/2004 | Olesen |

FOREIGN PATENT DOCUMENTS

| WO | 9943793 A1 | 9/1999 |
| WO | 9943794 A1 | 9/1999 |
| WO | 2004081171 A2 | 9/2004 |
| WO | 2006012899 A1 | 2/2006 |
| WO | 2006012902 A2 | 2/2006 |
| WO | 2008148845 A2 | 12/2008 |
| WO | 2011/058105 A1 | 5/2011 |

OTHER PUBLICATIONS

International Search Report from Corresponding PCT/EP2014/053853, dated Jul. 28, 2014.
"Novamyl/CGTase hybrid polypeptide #2", retrieved from EBI accession No. GSP:AEF76878, Database accession No. AEF76878 sequence, Apr. 6, 2006.
"Bacillus stearothermophilus maltogenic alpha-amylase variant C", retrieved from EBI accession No. GSP:AUL89266, Database accession No. AUL89266 sequence, Feb. 5, 2009.
"Bacterial maltogenic alpha amylase variant protein, SEQ ID No. 1", retrieved from EBI accession No. GSP:AEF82713, Database accession No. AEF82713 sequence, Apr. 6, 2006.

*Primary Examiner* — Tekchand Saidha
(74) *Attorney, Agent, or Firm* — McBee Moore Woodward & Vanik IP, LLC; Susan McBee; Chester Moore

(57) ABSTRACT

A variant polypeptide having alpha-amylase activity, wherein the variant has an amino acid sequence which, when aligned with the alpha-amylase comprising the sequence set out in SEQ ID NO: 2, comprises at least one substitution of an amino acid residue.

Such a variant polypeptide may be used in the preparation of a baked product.

18 Claims, 2 Drawing Sheets

ALPHA-AMYLASE VARIANTS

FIELD OF THE INVENTION

The invention relates to a variant polypeptide having alpha-amylase activity. The invention also relates to a nucleic acid sequence encoding such a variant, to a recombinant expression vector a said nucleic acid construct and to a recombinant host cell comprising a said expression vector. Further, the invention relates to a method for producing an alpha amylase via use of such a host cell. Also, the invention relates to a method of producing an alpha-amylase polypeptide variant. The invention further relates to a composition comprising an alpha-amylase variant, to use of such an alpha-amylase variant or alpha-amylase variant-containing composition in the preparation of a baked product, to a process for the production of a baked product and to the resulting baked product.

BACKGROUND OF THE INVENTION

In bread making starch plays a major role in the crumb formation and the rate of crumb staling of the baked bread. In dough starch is present as granules, absorbing only a small amount of water. During baking the starch gelatinization process is taking place. Amylose is leaking out of the granule and forms a continuous gel in the baking dough. Already during baking part of the amylose is re-crystallizing, resulting in stiffening of the gel and setting of the crumb. At the same time water is entering the granule and hydrating the amylopectin resulting in swelling of the granule. During storage of the bread over several days, the amylopectin starts to re-crystallize (also called retrogradation). The staling of bread is believed to be a direct reflection of the retrogradation of amylopectin. The starch and thus the breadcrumb become more rigid The firmness of bread after a certain storage time is depending on the initial softness, which is the softness after cooling down, and the rate of increase of firmness, the rate of staling.

Studies on bread staling have indicated that the starch fraction in bread recrystallizes during storage, thus causing an increase in crumb firmness, which may be measured as an increase in hardness of bread slices.

The present invention relates to an alpha-amylase. Alpha-amylases have been used in industry for a long time.

Alpha-amylases have traditionally been provided through the inclusion of malted wheat or barley flour and give several advantages to the baker. Alpha-amylase is used to give satisfactory gas production and gas retention during dough leavening and to give satisfactory crust color. This means that if this enzyme is not used in sufficient amount, the volume, texture, and appearance of the loaf are substantially impaired. Alpha-amylase occurs naturally within the wheat crop itself, measured routinely by Hagberg Falling Number (ICC method 107), and steps are taken to minimise such variations by the addition of alpha-amylase at the mill and through the use of specialty ingredients at the bakery as the enzyme is of such critical importance.

In more recent times, alpha-amylase from cereal has been largely replaced with enzymes from microbial sources, including fungal and bacterial sources. Through use of biotechnology in strain selection, fermentation and processing, enzymes can be prepared from such microbial sources and this brings advantage over malt flour because the enzyme is of more controlled quality, relatively pure and more cost effective in use.

The properties of alpha-amylases, and their technological effects, do however show important differences. Besides giving influence to gas production, gas retention and crust color, alpha-amylase can have bearing on the shelf-life of the baked product.

Starch within the wheat flour contains two principal fractions, amylose and amylopectin, and these are organised in the form of starch granules. A proportion of these granules from hard-milling wheat varieties become "damaged", with granules splitting apart as a consequence of the energy of milling. In the process of baking, the starch granules gelatinise; this process involves a swelling of the granule by the uptake of water and a loss of the crystalline nature of the granule; in particular amylopectins within the native granule are known to exist as crystallites and these molecules dissociate and lose crystallinity during gelatinisation. Once the bread has been baked, amylopectin recrystallises slowly over a numbers of days and it is this recrystallisation, or retrogradation of starch, that is regarded as being the principal cause of bread staling.

These varying forms of the starch and their interaction with alpha-amylase dictate the role the enzyme has with respect to baking technology. Alpha-amylase from fungal sources, most typically coming from *Aspergillus* species, acts principally on damaged starch during the mixing of dough and throughout fermentation/proof. The low heat stability of the enzyme means that the enzyme is inactivated during baking and, critically before starch gelatinisation has taken place, such that there is little or no breakdown of the starch from the undamaged fraction. As a consequence, fungal amylase is useful in providing sugars for fermentation and color, but has practically no value in extending shelf-life. Bacterial alpha-amylase, most typically from *Bacillus amyloliquifaciens*, on the other hand does bring extended temperature stability and activity during the baking of bread and while starch is undergoing gelatinisation. Bacterial amylase then leads to more extensive modification of the starch and, in turn, the qualities of the baked bread; in particular the crumb of the baked bread can be perceptibly softer throughout shelf-life and can permit the shelf-life to be increased. However, while bacterial alpha-amylase can be useful with regard to shelf-life extension, it is difficult to use practically as small over-doses lead to an unacceptable crumb structure of large and open pores, while the texture can become too soft and "gummy".

There is a need for an alpha-amylase with improved performance in industry, especially in the baking industry.

U.S. Pat. No. 4,598,048 describes the preparation of a maltogenic amylase enzyme. U.S. Pat. No. 4,604,355 describes a maltogenic amylase enzyme, preparation and use thereof. U.S. RE38,507 describes an antistaling process and agent.

WO99/43793 discloses amylolytic enzyme variants.
WO99/43794 maltogenic alpha-amylase variants.
WO2004/081171 discloses and enzyme.
WO2006/012899 discloses maltogenic alpha-amylase variants.

SUMMARY OF THE INVENTION

The invention relates to variant polypeptides having alpha-amylase activity, i.e. to alpha-amylase variants. An alpha-amylase variant of the invention may have one or more improved properties in comparison with a reference polypeptide, the reference polypeptide typically having alpha-amylase activity. A reference polypeptide may be a wild-type alpha-amylase, such as wild-type alpha-amylase, for example from *Alicyclobacillus pohliae*, in particular *Alicyclobacillus pohliae* NCIMB14276 strain. Variant polypeptides of the invention may be referred to as a "alpha-amylase variant", an "improved alpha-amylase" and the like.

The improved property will typically be a property with relevance to the use of the variant alpha-amylase in the preparation of a baked product.

An alpha-amylase variant with an improved property relevant for a baked product making may demonstrate reduced of hardness after storage of a baked product and/or reduced loss of resilience over storage of a baked product.

The improved property may include increased strength of the dough, increased elasticity of the dough, increased stability of the dough, reduced stickiness of the dough, improved extensibility of the dough, improved machineability of the dough, increased volume of the baked product, improved flavour of the baked product, improved crumb structure of the baked product, improved crumb softness of the baked product, reduced blistering of the baked product, improved crispiness, improved resilience both initial and in particular after storage, reduced hardness after storage and/or improved anti-staling of the baked product.

The improved property may include faster dough development time of the dough and/or reduced dough stickiness of the dough.

The improved property may include improved foldability of the baked product, such as improved foldability of a tortilla, a pancake, a flat bread, a pizza crust, a roti and/or a slice of bread.

The improved property may include improved flexibility of the baked product including improved flexibility of a tortilla, a pancake, a flat bread, a pizza crust, a roti and/or a slice of bread.

The improved property may include improved stackability of flat baked products including tortillas, pancakes, flat breads, pizza crusts, roti.

The improved property may include reduced stickiness of noodles and/or increased flexibility of noodles.

The improved property may include reduced clumping of cooked noodles and/or improved flavor of noodles even after a period of storage.

The improved property may include reduction of formation of hairline cracks in a product in crackers as well as creating a leavening effect and improved flavor development.

The improved property may include improved mouth feel and/or improved softness on squeeze, The improved property may include reduced damage during transport, including reduced breaking during transport.

The improved property may include reduced hardness after storage of gluten-free bread.

The improved property may include improved resilience of gluten-free bread. The improved property may include improved resilience both initial and in particular after storage of gluten-free bread.

The improved property may include reduced hardness after storage of rye bread.

The improved property may include reduced loss of resilience over storage of rye bread.

The improved property may include improved slice ability. This may be demonstrated by observing the amount of crumbs after slicing. Less crumbs indicate a better slice ability The improved property may include improved crumb structure and/or resilience, without creating gumminess.

The improved property may include improved cohesiveness of the baked product, including improved cohesiveness of a sponge cake.

The improved property may include reduced loss of resilience over storage of a baked product comprising at least 5 wt % sugar, in an aspect comprising at least 8 wt % sugar, in an aspect comprising at least 12 wt % sugar, in an aspect comprising at least 15 wt % sugar based on flour. In an aspect comprising at least 18 wt % sugar, in an aspect comprising at least 20 wt % sugar, in an aspect comprising at least 25 wt % sugar, in an aspect comprising at least 30 wt % sugar based on flour. Herein 5 wt % sugar means 50 grams sugar per 1000 gram of flour used in the recipe, etc.

The improved property may include reduced hardness after storage of a baked product comprising at least 5 wt % sugar, in an aspect comprising at least 8 wt % sugar, in an aspect comprising at least 12 wt % sugar, in an aspect comprising at least 15 wt % sugar based on flour. In an aspect comprising at least 18 wt % sugar, in an aspect comprising aspect at least 20 wt % sugar, in an aspect comprising at least 25 wt % sugar, in an aspect comprising at least 30 wt % sugar based on flour. Herein 5 wt % sugar means 50 grams sugar per 1000 gram of flour used in the recipe, etc.

Each of these improvements may be determined as compared with a reference polypeptide. The improved property may be demonstrated by preparing a baked product comprising the alpha-amylase variant and another comprising a parent polypeptide and comparing the results.

The improved property may be demonstrated in an assay or (bio)chemical analysis.

In particular, a variant alpha-amylase of the invention may show improved productivity in comparison with a reference polypeptide. Alternatively, or in addition, a variant alpha-amylase of the invention may show an altered, such as reduced or increased, temperature stability or an altered activity at pH relevant for the baked product making process, such as a lower pH or a higher pH, as compared with a reference polypeptide.

The improved property may include:
increased (thermo)stability in comparison with a parent polypeptide having alpha-amylase activity,
increased specific activity in comparison with a parent polypeptide having alpha-amylase activity,
increased sucrose tolerance in comparison with a parent polypeptide having alpha-amylase activity,
increased stability/activity at different pH range in comparison with a parent polypeptide having alpha-amylase activity,
change in product spectrum (defined as ratio of one product over another) in comparison with a parent polypeptide having alpha-amylase activity,
increased activity on raw starch in comparison with a parent polypeptide having alpha-amylase activity,
altered temperature optimum,
alter substrate specificity, or
increased productivity in the production of the alpha-amylase variant; in comparison with a parent polypeptide having alpha-amylase activity.

In an aspect of the invention, there is provided a variant polypeptide having alpha-amylase activity, wherein the variant has an amino acid sequence which, when aligned with the alpha-amylase comprising the sequence set out in SEQ ID NO: 2, comprises at least one substitution of an amino acid residue corresponding to any of amino acids 1, 2, 3, 4, 5, 6, 7, 8, 9, 10, 11, 12, 13, 14, 15, 6, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200,
201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 251, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 351, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 451, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 551, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619,
620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 651, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686,
said positions being defined with reference to SEQ ID NO: 2 and wherein the variant has one or more altered properties as compared with a reference polypeptide having alpha-amylase activity.

In an embodiment according to the invention there is provided a variant polypeptide having alpha-amylase activity, wherein the variant has an amino acid sequence which, when aligned with the alpha-amylase comprising the sequence set out in SEQ ID NO: 2, comprises at least one substitution of an amino acid residue corresponding to any of amino acids 4, 6, 13, 14, 15, 16, 20, 45, 47, 51, 54, 61, 68, 69, 70, 71, 72, 73, 74, 75, 77, 78, 80, 82, 87, 88, 94, 95, 100, 103, 104, 117, 124, 125, 126, 128, 130, 133, 134, 136, 143, 144, 146, 168, 174, 177, 178, 183, 186, 188, 189, 190, 194, 195, 199, 200, 201, 204, 207, 210, 214, 217, 219, 222, 225, 227, 233, 234, 235, 236, 240, 251, 252, 254, 258, 259, 260, 261, 262, 263, 264, 266, 267, 269, 271, 273, 281, 282, 283, 284, 286, 288, 299, 322, 323, 325, 327, 328, 331, 334, 350, 356, 358, 367, 370, 371, 374, 377, 378, 388, 391, 414, 421, 422, 445, 450, 467, 488, 505, 536, 548, 554, 583, 588, 603, 637, 648, 651, 652, 660, 676, 677,
said positions being defined with reference to SEQ ID NO: 2 and wherein the variant has one or more altered properties as compared with a reference polypeptide having alpha-amylase activity.

The invention also provides:
a nucleic acid sequence encoding a variant of the invention;
a nucleic acid construct comprising such a nucleic acid sequence operably linked to one or more control sequences capable of directing the expression of an alpha-amylase in a suitable expression host;
a recombinant expression vector comprising such a nucleic acid construct; and
a recombinant host cell comprising such an expression vector.

The invention also relate to a method for producing an alpha-amylase comprising cultivating the host cell of the invention under conditions conducive to production of the alpha-amylase and recovering the alpha-amylase.

Also, the invention relates to a method of producing an alpha-amylase polypeptide variant, which method comprises:
a) selecting a polypeptide having alpha-amylase activity;
b) substituting at least one amino acid residue corresponding to any of amino acids
4, 6, 13, 14, 15, 16, 20, 45, 47, 51, 54, 61, 68, 69, 70, 71, 72, 73, 74, 75, 77, 78, 80, 82, 87, 88, 94, 95, 100, 103, 104, 117, 124, 125, 126, 128, 130, 133, 134, 136, 143, 144, 146, 168, 174, 177, 178, 183, 186, 188, 189, 190, 194, 195, 199, 200, 201, 204, 207, 210, 214, 217, 219, 222, 225, 227, 233, 234, 235, 236, 240, 251, 252, 254, 258, 259, 260, 261, 262, 263, 264, 266, 267, 269, 271, 273, 281, 282, 283, 284, 286, 288, 299, 322, 323, 325, 327, 328, 331, 334, 350, 356, 358, 367, 370, 371, 374, 377, 378, 388, 391, 414, 421, 422, 445, 450, 467, 488, 505, 536, 548, 554, 583, 588, 603, 637, 648, 651, 652, 660, 676, 677,
said positions being defined with reference to SEQ ID NO: 2;
c) optionally substituting one or more further amino acids as defined in b);
d) preparing the variant resulting from steps a)-c);
e) determining a property of the variant; and
f) selecting a variant having an altered property in comparison to the alpha-amylase comprising the sequence set out in SEQ ID NO: 2, thereby to produce an alpha-amylase polypeptide variant.

Further the invention relates to:
a composition comprising the variant of the invention or obtainable by a method of the invention;
use of a variant alpha-amylase according to the invention or of a composition of the invention in the preparation of a baked product;
a process for the production of a baked product, which method comprises comprising adding an effective amount of a variant polypeptide according to the invention of a composition according to the invention to dough and carrying out appropriate further baking manufacturing steps; and
a baked product obtainable by such process or use.

DESCRIPTION OF THE SEQUENCE LISTING

Figure 1:
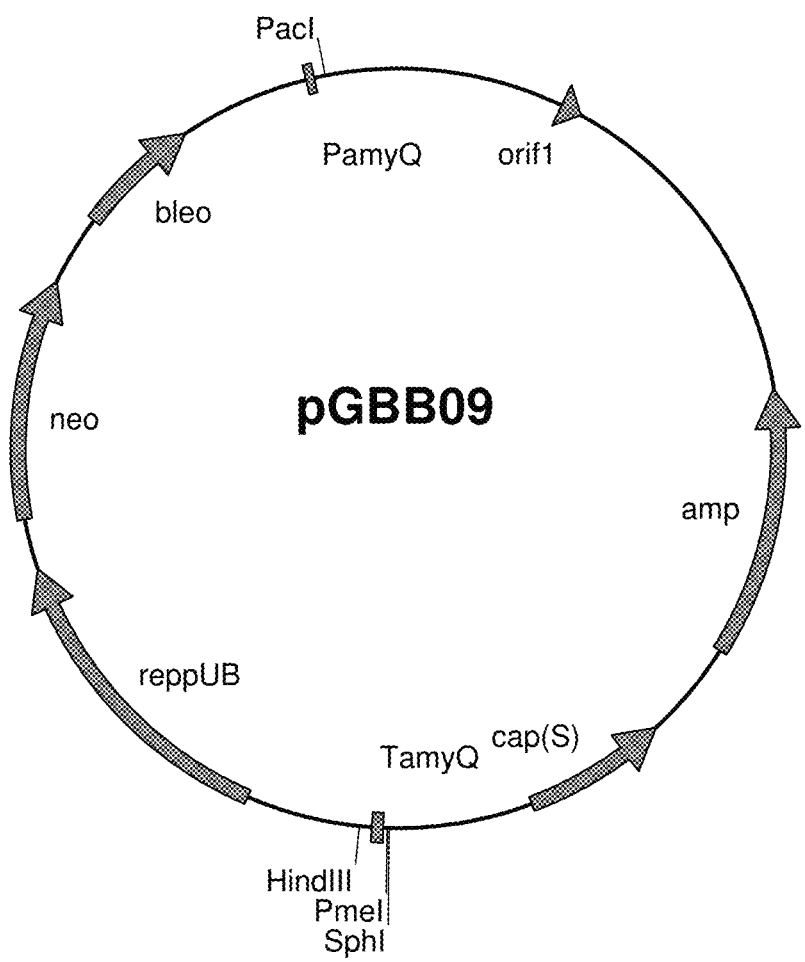
FIG. 1. Sets out the plasmid map op pGBB09, the plasmid is used to construct the expression vectors for alpha-amylase variants.

SEQ ID NO: 1 sets out the polynucleotide sequence from *Alicyclobacillus pohliae* NCIMB14276 encoding the wild type signal sequence (set out in nucleotides 1 to 99), the wild-type alpha-amylase polypeptide (set out in nucleotides 100 to 2157), and a stop codon at the 3'-terminus (set out in nucleotides 2157 to 2160).

SEQ ID NO: 2 sets out the amino acid sequence of the *Alicyclobacillus pohliae* NCIMB14276 wild type alpha-amylase polypeptide.

SEQ ID NO: 3 sets out a synthetic DNA fragment containing the PmeI restriction site, the amyQ terminator and the SphI and HindIII restriction site.

SEQ ID NO: 4 sets out a synthetic DNA fragment containing a ribosome binding site and PacI restriction site.

SEQ ID NO: 5 sets out a synthetic DNA fragment containing a double stop codon and PmeI restriction site.

SEQ ID NO 6: sets out the polynucleotide sequence of a synthetic DNA construct exciting of a PacI site, ribosome binding site, wild type DSM-AM sequence as set out in SEQ ID NO:1, double stop codon and PmeI restriction site.

SEQ ID NO 7: sets out the amino acid sequence of a variant of the *Alicyclobacillus pohliae* NCIMB14276 wild type alpha-amylase polypeptide.

SEQ ID NO 8: sets out the amino acid sequence of another variant of the *Alicyclobacillus pohliae* NCIMB14276 wild type alpha-amylase polypeptide.

DETAILED DESCRIPTION OF THE INVENTION

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

Alpha-Amylase Activity

The alpha-amylase variant according to the invention and the parent polypeptide herein are a starch degrading enzymes. The alpha-amylase variant according to the invention and the parent polypeptide herein have alpha-amylase activity. Alpha-amylase activity can suitably be determined using the Ceralpha® procedure, which is recommended by the American Association of Cereal Chemists (AACC).

NBAU Activity

Enzymatic activity of a alpha-amylase variant and of a parent polypeptide may be expressed as NBAU. NBAU activity can suitably be determined using the NBAU assay as described herein.

Pre-mix

The term "pre-mix" is defined herein to be understood in its conventional meaning, i.e. as a mix of baking agents, generally including flour, which may be used not only in industrial bread-baking plants/facilities, but also in retail bakeries. The pre-mix may be prepared by mixing the alpha-amylase polypeptide and the G4-forming amylase or the enzyme composition according to the invention with a suitable carrier such as flour, starch or a salt. The pre-mix may contain additives as mentioned herein.

Baked Product

The term 'baked product' refers to a baked food product prepared from a dough.

Examples of baked products, whether of a white, brown or whole-meal type, which may be advantageously produced by the present invention include bread (in particular white, whole-meal or rye bread), typically in the form of loaves or rolls, French baguette-type bread, pastries, croissants, brioche, panettone, pasta, noodles (boiled or (stir-)fried), pita bread and other flat breads, tortillas, tacos, cakes, pancakes, cookies in particular biscuits, doughnuts, including yeasted doughnuts, bagels, pie crusts, steamed bread, crisp bread, brownies, sheet cakes, snack foods (e.g., pretzels, tortilla chips, fabricated snacks, fabricated potato crisps). The term baked product includes, bread containing from 2 to 30 wt % sugar, fruit containing bread, breakfast cereals, cereal bars, eggless cake, soft rolls and gluten-free bread. Gluten free bread herein and herein after is bread than contains at most 20 ppm gluten. Several grains and starch sources are considered acceptable for a gluten-free diet. Frequently used sources are potatoes, rice and tapioca (derived from cassava) Baked product includes without limitation tin bread, loaves of bread, twists, buns, such as hamburger buns or steamed buns, chapati, rusk, dried steam bun slice, bread crumb, matzos, focaccia, melba toast, zwieback, croutons, soft pretzels, soft and hard bread, bread sticks, yeast leavened and chemically-leavened bread, laminated dough products such as Danish pastry, croissants or puff pastry products, muffins, danish, bagels, confectionery coatings, crackers, wafers, pizza crusts, tortillas, pasta products, crepes, waffles, parbaked products and refrigerated and frozen dough products.

An example of a parbaked product includes, without limitation, partially baked bread that is completed at point of sale or consumption with a short second baking process.

The bread may be white or brown pan bread; such bread may for example be manufactured using a so called American style Sponge and Dough method or an American style Direct method.

The term tortilla herein includes corn tortilla and wheat tortilla. A corn tortilla is a type of thin, flat bread, usually unleavened made from finely ground maize (usually called "corn" in the United States). A flour tortilla is a type of thin, flat bread, usually unleavened, made from finely ground wheat flour. The term tortilla further includes a similar bread from South America called arepa, though arepas are typically much thicker than tortillas. The term tortilla further includes a laobing, a pizza-shaped thick "pancake" from China and an Indian Roti, which is made essentially from wheat flour. A tortilla usually has a round or oval shape and may vary in diameter from about 6 to over 30 cm.

Dough

The term "dough" is defined herein as a mixture of flour and other ingredients. In one aspect the dough is firm enough to knead or roll. The dough may be fresh, frozen, prepared or parbaked. The preparation of frozen dough is described by Kulp and Lorenz in Frozen and Refrigerated Doughs and Batters.

Dough is made using dough ingredients, which include without limitation (cereal) flour, a lecithin source including egg, water, salt, sugar, flavours, a fat source including butter, margarine, oil and shortening, baker's yeast, chemical leavening systems such as a combination of an acid (generating compound) and bicarbonate, a protein source including milk, soy flour, oxidants (including ascorbic acid, bromate and Azodicarbonamide (ADA)), reducing agents (including L-cysteine), emulsifiers (including mono/di glycerides, monoglycerides such as glycerol monostearate (GMS), sodium stearoyl lactylate (SSL), calcium stearoyl lactylate (CSL), polyglycerol esters of fatty acids (PGE) and diacetyl tartaric acid esters of mono- and diglycerides (DATEM), gums (including guargum and xanthangum), flavours, acids (including citric acid, propionic acid), starch, modified starch, gluten, humectants (including glycerol) and preservatives.

Cereals include maize, rice, wheat, barley, sorghum, millet, oats, rye, triticale, buckwheat, quinoa, spelt, einkorn, emmer, durum and kamut.

Dough is usually made from basic dough ingredients including (cereal) flour, such as wheat flour or rice flour, water and optionally salt. For leavened products, primarily baker's yeast is used next to chemical leavening systems such as a combination of an acid (generating compound) and bicarbonate.

The term dough herein includes a batter. A batter is a semi-liquid mixture, being thin enough to drop or pour from a spoon, of one or more flours combined with liquids such as water, milk or eggs used to prepare various foods, including cake.

The dough may be made using a mix including a cake mix, a biscuit mix, a brownie mix, a bread mix, a pancake mix and a crepe mix.

The term dough includes frozen dough, which may also be referred to as refrigerated dough. There are different types of frozen dough; that which is frozen before proofing and that which is frozen after a partial or complete proofing stage. The frozen dough is typically used for manufacturing baked products including without limitation biscuits, breads, bread sticks and croissants.

A gene or cDNA coding for an alpha-amlyase or pro-alpha-amylase, for example a variant of the invention, may be cloned and over-expressed in a host organism. Well known host organisms that have been used for alpha amylase over-expression in the past include *Aspergillus, Kluyveromyces, Trichoderma, Escherichia coli, Pichia, Saccharomyces, Yarrowia, Neurospora* or *Bacillus*.

The alpha-amylase variant may be manufactured industrially using recombinant DNA technology, e.g. using filamentous fungi such as *Aspergillus* species, yeast strains, e.g. of *Klyuveromyces* species, or *bacterial* species, e.g. *E. coli*, as host organisms. Such recombinant microbial production strains are constructed and continuously improved using DNA technology as well as classical strain improvement measures directed towards optimising the expression and secretion of a heterologous protein.

In the invention, an alpha-amylase variant may be provided in the form of prealpha-amylase variant or (mature) alpha-amylase variant. A corresponding nucleic acid sequence may also be provided, i.e. a polynucleotide that encodes a pre-alpha-amylase or a (mature) alpha-amylase may be provided.

Herein, positions which may be substituted to achieve a variant of the invention are defined with reference to SEQ ID NO: 2 which is a mature alpha-amylase, i.e. it is a sequence which does not include a presequence.

The invention concerns variant polypeptides having alpha-amylase activity as compared with a reference polypeptide having alpha-amylase activity. The reference polypeptide may typically be a wild-type polypeptide having alpha-amylase activity, such as the alpha-amylase of SEQ ID NO: 2. The reference polypeptide may also be referred to as a parent polypeptide or comparison polypeptide.

More concretely, the invention relates to a variant polypeptide having alpha-amylase activity, wherein the variant has an amino acid sequence which, when aligned with the alpha-amylase comprising the sequence set out in SEQ ID NO: 2, comprises at least one substitution of an amino acid residue corresponding to any of amino acids 1, 2, 3, 4, 5, 6, 7, 8, 9, 10, 11, 12, 13, 14, 15, 6, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200,
201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 251, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 351, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 451, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 551, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 651, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, said positions being defined with reference to SEQ ID NO: 2 and wherein the variant has one or more altered properties as compared with a reference polypeptide having alpha-amylase activity.

A wild type reference polypeptide may be obtained from any suitable organisms.

Suitable wild type reference polypeptides may be obtained from *Alicyclobacillus pohliae* NCIMB14276.

Preferably, the reference polypeptide is the alpha amylase set out in SEQ ID NO: 2.

The parent polypeptide having alpha-amylase activity is preferably is the alpha amylase set out in SEQ ID NO: 2.

A variant polypeptide will typically have an improved property as compared to a reference polypeptide, in particular with respect to a property relevant to the use of the variant polypeptide in baked product making.

Improved productivity may be demonstrated by an alpha-amylase variant that shows improved expression as compared with a parent polypeptide.

The improved property will typically be a property with relevance to the use of the variant alpha-amylase in the preparation of a baked product.

An alpha-amylase variant with an improved property relevant for a baked product making may demonstrate reduced of hardness after storage of a baked product and/or reduced loss of resilience over storage of a baked product.

The improved property may include increased strength of the dough, increased elasticity of the dough, increased stability of the dough, reduced stickiness of the dough, improved extensibility of the dough, improved machineability of the dough, increased volume of the baked product, improved flavour of the baked product, improved crumb structure of the baked product, improved crumb softness of the baked product, reduced blistering of the baked product, improved crispiness, improved resilience both initial and in particular after storage, reduced hardness after storage and/or improved anti-staling of the baked product.

The improved property may include faster dough development time of the dough and/or reduced dough stickiness of the dough.

The improved property may include improved foldability of the baked product, such as improved foldability of a tortilla, a pancake, a flat bread, a pizza crust, a roti and/or a slice of bread.

The improved property may include improved flexibility of the baked product including improved flexibility of a tortilla, a pancake, a flat bread, a pizza crust, a roti and/or a slice of bread.

The improved property may include improved stackability of flat baked products including tortillas, pancakes, flat breads, pizza crusts, roti.

The improved property may include reduced stickiness of noodles and/or increased flexibility of noodles.

The improved property may include reduced clumping of cooked noodles and/or improved flavor of noodles even after a period of storage.

The improved property may include reduction of formation of hairline cracks in a product in crackers as well as creating a leavening effect and improved flavor development.

The improved property may include improved mouth feel and/or improved softness on squeeze, The improved property may include reduced damage during transport, including reduced breaking during transport.

The improved property may include reduced hardness after storage of gluten-free bread.

The improved property may include improved resilience of gluten-free bread. The improved property may include improved resilience both initial and in particular after storage of gluten-free bread.

The improved property may include reduced hardness after storage of rye bread.

The improved property may include reduced loss of resilience over storage of rye bread The improved property may include reduced loss of resilience over storage of a baked product comprising at least 5 wt % sugar, in an aspect comprising at least 8 wt % sugar, in an aspect comprising at least 12 wt % sugar, in an aspect comprising at least 15 wt % sugar based on flour. In an aspect comprising at least 18 wt % sugar, in an aspect comprising at least 20 wt % sugar, in an aspect comprising at least 25 wt % sugar, in an aspect comprising at least 30 wt % sugar based on flour. Herein 5 wt % sugar means 50 grams sugar per 1000 grams of flour used in the recipe.

The improved property may include reduced hardness after storage of a baked product comprising at least 5 wt % sugar, in an aspect comprising at least 8 wt % sugar, in an aspect comprising at least 12 wt % sugar, in an aspect comprising at least 15 wt % sugar based on flour. In an aspect comprising at least 18 wt % sugar, in an aspect comprising aspect at least 20 wt % sugar, in an aspect comprising at least 25 wt % sugar, in an aspect comprising at least 30 wt % sugar based on flour. Herein 5 wt % sugar means 50 grams sugar per 1000 grams of flour used in the recipe, etc.

Each of these improvements may be determined as compared with a reference polypeptide. The improved property may be demonstrated by preparing a baked product comprising the alpha-amylase variant and another comprising a parent polypeptide and comparing the results.

The improved property may be demonstrated in an assay or (bio)chemical analysis.

In particular, a variant alpha-amylase of the invention may show improved productivity in comparison with a reference polypeptide. Alternatively, or in addition, a variant alpha-amylase of the invention may show an altered, such as reduced or increased, temperature stability or an altered activity at pH relevant for the baked product making process, such as a lower pH or a higher pH, as compared with a reference polypeptide.

The improved property may include:

increased (thermo)stability in comparison with a parent polypeptide having alpha-amylase activity, increased specific activity in comparison with a parent polypeptide having alpha-amylase activity, increased sucrose tolerance in comparison with a parent polypeptide having alpha-amylase activity, increased stability/activity at different pH range in comparison with a parent polypeptide having alpha-amylase activity, change in product spectrum (defined as ratio of one product over another) in comparison with a parent polypeptide having alpha-amylase activity, increased activity on raw starch in comparison with a parent polypeptide having alpha-amylase activity, altered temperature optimum,
alter substrate specificity, or
increased productivity in the production of the alpha-amylase variant; in comparison with a parent polypeptide having alpha-amylase activity.

Thermostability may be determined by measuring the residual activity after incubation at a higher temperature (e.g. 50-100° C. for 1-20 min), using a suitable activity assay (such as Ceralpha) or alternatively the NBAU assay as described herein.

Thermostability may be determined using an assay described herein. Thermostability may be determined at a suitable pH such as at pH 4 or at pH 5. Thermostability may be determined in the presence of sucrose.

In an embodiment of the alpha-amylase polypeptide variant according to the invention, said variant has at least 70% identity with the polypeptide sequence as set out in SEQ ID NO: 2,
which, when aligned with the sequence as set out in SEQ ID NO: 2, comprises at least one substitution of an amino acid residue corresponding to any of amino acids
13, 61, 68, 70, 75, 88, 128, 133, 168, 188, 200, 222, 254, 261, 264, 281, 282, 327, 371, 388,
said positions being defined with reference to SEQ ID NO: 2;
and wherein the variant has an increased thermostability compared with the reference polypeptide as set out in SEQ ID NO: 2.

In an embodiment the alpha-amylase polypeptide variant according to the invention has an increased thermostability compared with the polypeptide as set out in SEQ ID NO: 2 and has at least 75%, in an aspect at least 80%, in an aspect at least 85%, in an aspect at least 90%, in an aspect at least 95%, in an aspect at least 96%, in an aspect at least 97% in an aspect at least 98%, in an aspect at least 99%, in an aspect at least 99.5% identity with the polypeptide sequence as set out in SEQ ID NO: 2.

In an embodiment of the alpha-amylase polypeptide variant according to the invention, said variant has at least 70% identity with the polypeptide sequence as set out in SEQ ID NO: 2,
which, when aligned with the sequence as set out in SEQ ID NO: 2, comprises at least one substitution of an amino acid residue corresponding to Q13E, L61F, T68A, W70Y, L75F, G88A, F128I, S133T, F168Y, F188I, S200N, A222V, V254F, D261G, A264S, V281L, L282F, L282M, L282I, L282T, N327S, N371G, A388L,
said positions being defined with reference to SEQ ID NO: 2;
and wherein the variant has an increased thermostability compared with the reference polypeptide as set out in SEQ ID NO: 2.

Specific activity may be determined by measuring the activity per mg of protein (amount of protein can e.g. be estimated from SDS-PAGE, or if sample is pure enough can be determined using Bradford assay). Suitable examples of an assay to determine the specific activity include the NBAU assay and the Maltotriose assay as described herein.

Sucrose tolerance may be determined by measuring the activity in the presence of increasing concentration of sucrose (for example incubate with Phadebas tablets for 15 min at 60° C. in the presence of 0-40% (by weight) sucrose. Express as a percentage of the activity at 0% sucrose.) The activity may be determined using a suitable activity assay (such as Ceralpha) or alternatively the NBAU assay as described herein.

pH stability may be determined by measuring the thermostability in a pH range (measure thermostability as described above, but do incubation in a range of pH values, e.g. 2-12).

In an embodiment of the alpha-amylase polypeptide variant according to the invention, said variant has at least 70% identity with the polypeptide sequence as set out in SEQ ID NO: 2,
which, when aligned with the sequence as set out in SEQ ID NO: 2, comprises at least one substitution of an amino acid residue corresponding to any of amino acids
13, 61, 68, 70, 75, 88, 128, 133, 168, 188, 200, 222, 254, 261, 264, 281, 282, 327, 371, 388,
said positions being defined with reference to SEQ ID NO: 2;
and wherein the variant has an increased thermostability compared with the reference polypeptide as set out in SEQ ID NO: 2, while the specific activity of the variant has reduced by at most 10% as compared with the reference polypeptide.

In an aspect of this embodiment the specific activity of the variant has reduced by at most 20%, in an aspect by at most 30%, in an aspect by at most 40%, in an aspect by at most 50% as compared to the reference polypeptide. In a further aspect of this embodiment the specific activity of the variant is at least the same or has increased compared to the reference polypeptide. In a further aspect of this embodiment the specific activity is determined using maltotriose as a substrate.

In an embodiment the alpha-amylase polypeptide variant according to the invention has an increased thermostability compared with the polypeptide as set out in SEQ ID NO: 2 and has at least 75%, in an aspect at least 80%, in an aspect at least 85%, in an aspect at least 90%, in an aspect at least 95%, in an aspect at least 96%, in an aspect at least 97% in an aspect at least 98%, in an aspect at least 99%, in an aspect at least 99.5% identity with the polypeptide sequence as set out in SEQ ID NO: 2, while the specific activity of the variant has reduced by at most 10% as compared with the reference polypeptide.

In an aspect of this embodiment the specific activity of the variant has reduced by at most 20%, in an aspect by at most 30%, in an aspect by at most 40%, in an aspect by at most 50% as compared to the reference polypeptide. In a further aspect of this embodiment the specific activity of the variant is at least the same or has increased compared to the reference polypeptide. In a further aspect of this embodiment the specific activity is determined using maltotriose as a substrate.

In an embodiment of the alpha-amylase polypeptide variant according to the invention, said variant has at least 70% identity with the polypeptide sequence as set out in SEQ ID NO: 2,
which, when aligned with the sequence as set out in SEQ ID NO: 2, comprises at least one substitution of an amino acid residue corresponding to Q13E, L61F, T68A, W70Y, L75F, G88A, F128I, S133T, F168Y, F188I, S200N, A222V, V254F, D261G, A264S, V281L, L282F, L282M, L282I, L282T, N327S, N371G, A388L,
said positions being defined with reference to SEQ ID NO: 2;
and wherein the variant has an increased thermostability compared with the reference polypeptide as set out in SEQ ID NO: 2, while the specific activity of the variant has reduced by at most 10% as compared with the reference polypeptide.

In an aspect of this embodiment the specific activity of the variant has reduced by at most 20%, in an aspect by at most 30%, in an aspect by at most 40%, in an aspect by at most 50% as compared to the reference polypeptide. In a further aspect of this embodiment the specific activity of the variant is at least the same or has increased compared to the reference polypeptide. In a further aspect of this embodiment the specific activity is determined using maltotriose as a substrate.

Sucrose Tolerance

Sucrose tolerance of a variant according to the invention may be expressed as the ratio of

[Activity of a variant in the presence of sucrose] to [Activity of the variant in the absence of sucrose], expressed as a percentage of the ratio of

[Activity of a reference polypeptide having alpha-amylase activity in the presence of sucrose] to [Activity of the reference polypeptide having alpha-amylase activity in the absence of sucrose].

Sucrose tolerance of a variant according to the invention may be expressed as the ratio of

[Activity on maltotriose of a variant in the presence of sucrose] to [Activity on maltotriose of the variant in the absence of sucrose], expressed as a percentage of the ratio of

[Activity on maltotriose of a reference polypeptide having alpha-amylase activity in the presence of sucrose] to [Activity on maltotriose of the reference polypeptide having alpha-amylase activity in the absence of sucrose].

In an aspect sucrose tolerance of a variant according to the invention may be expressed as the ratio of

[Activity of the variant in Assay 2B (as described herein)] to [Activity of the variant in Assay 2A (as described herein)], expressed as a percentage of the ratio of

[Activity of the reference polypeptide in Assay 2B (as described herein)] to [Activity of the reference polypeptide in Assay 2A (as described herein)].

The percentage thus obtained may be used as measure for the sucrose tolerance of the variant according to the invention. A sucrose tolerance of more than 100% shows that the variant has an increased sucrose tolerance compared to the reference polypeptide having alpha-amylase activity.

In an aspect of the invention the variant according to the invention has an increased sucrose tolerance compared with a reference polypeptide having alpha-amylase activity, preferably the reference polypeptide having alpha-amylase activity has an amino acid sequence as set out in SEQ ID NO: 2.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to any of amino acids 15, 16, 45, 75, 94, 94, 129, 134, 174, 177, 178, 186, 194, 210, 234, 254, 281, 323, 325, 358, 371, 652, 13, 70, 72, 282, 283, 284, 261, 77, 88, 78, 134, 133, said positions being defined with reference to SEQ ID NO: 2;

and wherein the variant has an increased sucrose tolerance compared with the reference polypeptide as set out in SEQ ID NO: 2.

In an embodiment the alpha-amylase polypeptide variant according to the invention has an increased sucrose tolerance compared with the polypeptide as set out in SEQ ID NO: 2 and has at least 75%, in an aspect at least 80%, in an aspect at least 85%, in an aspect at least 90%, in an aspect at least 95%, in an aspect at least 96%, in an aspect at least 97% in an aspect at least 98%, in an aspect at least 99%, in an aspect at least 99.5% identity with the polypeptide sequence as set out in SEQ ID NO: 2.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to any of amino acids 15, 16, 45, 75, 94, 94, 129, 134, 174, 177, 178, 186, 194, 210, 234, 254, 281, 323, 325, 358, 371, 652, 13, 70, 72, 282, 283, 284, 261, 133, said positions being defined with reference to SEQ ID NO: 2;

and wherein the variant has an increased sucrose tolerance compared with the reference polypeptide as set out in SEQ ID NO: 2.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to I15V, I16T, M45L, L75V, T94A, T94P, V129A, T134S, I174L, W177F, D178N, K186Q, F194Y, L210F, N234P, V254F, V281L, T323N, I325F, S358A, N371G, F652I, Q13E, W70Y, S72T, L282F, L282M, L282T, D283N, D283S, F284W, D261G, S133L, said positions being defined with reference to SEQ ID NO: 2;

and wherein the variant has an increased sucrose tolerance compared with the reference polypeptide as set out in SEQ ID NO: 2.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises a Cysteine amino acid at both positions 77 and 88 or a Cysteine amino acid at both positions 78 and 134, said positions being defined with reference to SEQ ID NO: 2; and wherein the variant has an increased sucrose tolerance compared with the reference polypeptide as set out in SEQ ID NO: 2.

In an aspect of the invention the variant according to the invention has an increased sucrose tolerance at pH 5 compared with a reference polypeptide having alpha-amylase activity, preferably the reference polypeptide having alpha-amylase activity has an amino acid sequence as set out in SEQ ID NO: 2.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to any of amino acids 15, 16, 45, 75, 94, 94, 129, 134, 174, 177, 178, 186, 194, 210, 234, 254, 281, 323, 325, 358, 371, 652, 13, 70, 72, 282, 283, 284, 261, 77, 88, 78, 134, 133, said positions being defined with reference to SEQ ID NO: 2;

and wherein the variant has an increased sucrose tolerance at pH 5 compared with the reference polypeptide as set out in SEQ ID NO: 2.

In an embodiment the alpha-amylase polypeptide variant according to the invention has an increased sucrose tolerance at pH 5 compared with the polypeptide as set out in SEQ ID NO: 2 and has at least 75%, in an aspect at least 80%, in an aspect at least 85%, in an aspect at least 90%, in an aspect at least 95%, in an aspect at least 96%, in an aspect at least 97% in an aspect at least 98%, in an aspect at least 99%, in an aspect at least 99.5% identity with the polypeptide sequence as set out in SEQ ID NO: 2.

In an embodiment of the alpha-amylase polypeptide variant according to the invention, said variant has at least 70% identity with the polypeptide sequence as set out in SEQ ID NO: 2,
which, when aligned with the sequence as set out in SEQ ID NO: 2, comprises at least one substitution of an amino acid residue corresponding to any of amino acids
15, 16, 45, 75, 94, 94, 129, 134, 174, 177, 178, 186, 194, 210, 234, 254, 281, 323, 325, 358, 371, 652, 13, 70, 72, 282, 283, 284, 261, 133,
said positions being defined with reference to SEQ ID NO: 2;
and wherein the variant has an increased sucrose tolerance at pH 5 compared with the reference polypeptide as set out in SEQ ID NO: 2.

In an embodiment of the alpha-amylase polypeptide variant according to the invention, said variant has at least 70% identity with the polypeptide sequence as set out in SEQ ID NO: 2,
which, when aligned with the sequence as set out in SEQ ID NO: 2, comprises at least one substitution of an amino acid residue corresponding to
I15V, I16T, M45L, L75V, T94A, T94P, V129A, T134S, I174L, W177F, D178N, K186Q, F194Y, L210F, N234P, V254F, V281L, T323N, I325F, S358A, N371G, F652I, Q13E, W70Y, S72T, L282F, L282M, L282T, D283N, D283S, F284W, D261G, S133L,
said positions being defined with reference to SEQ ID NO: 2;
and wherein the variant has an increased sucrose tolerance at pH 5 compared with the reference polypeptide as set out in SEQ ID NO: 2.

In an embodiment of the alpha-amylase polypeptide variant according to the invention, said variant has at least 70% identity with the polypeptide sequence as set out in SEQ ID NO: 2,
which, when aligned with the sequence as set out in SEQ ID NO: 2, comprises a Cysteine amino acid at both positions 77 and 88 or a Cysteine amino acid at both positions 78 and 134,
said positions being defined with reference to SEQ ID NO: 2; and wherein the variant has an increased sucrose tolerance at pH 5 compared with the reference polypeptide as set out in SEQ ID NO: 2.

In an embodiment of the alpha-amylase polypeptide variant according to the invention, said variant has at least 70% identity with the polypeptide sequence as set out in SEQ ID NO: 2,
which, when aligned with the sequence as set out in SEQ ID NO: 2, comprises substitution of an amino acid residue corresponding to amino acid
129 and/or 194,
said positions being defined with reference to SEQ ID NO: 2;
and wherein the variant has an increased sucrose tolerance at pH 5, compared with the reference polypeptide as set out in SEQ ID NO: 2.

In an embodiment of the alpha-amylase polypeptide variant according to the invention, said variant has at least 70% identity with the polypeptide sequence as set out in SEQ ID NO: 2,
which, when aligned with the sequence as set out in SEQ ID NO: 2, comprises substitution of an amino acid residue corresponding to amino acid
129 and/or 194,
said positions being defined with reference to SEQ ID NO: 2;
and wherein the variant has an increased sucrose tolerance at pH 5, compared with the reference polypeptide as set out in SEQ ID NO: 2.

In an embodiment of the alpha-amylase polypeptide variant according to the invention, said variant has at least 70% identity with the polypeptide sequence as set out in SEQ ID NO: 2,
which, when aligned with the sequence as set out in SEQ ID NO: 2, comprises at least one substitution of an amino acid residue corresponding to V129A and/or F194Y said positions being defined with reference to SEQ ID NO: 2; and wherein the variant has an increased sucrose tolerance, compared with the reference polypeptide as set out in SEQ ID NO: 2.

In an embodiment of the alpha-amylase polypeptide variant according to the invention, said variant has at least 70% identity with the polypeptide sequence as set out in SEQ ID NO: 2,
which, when aligned with the sequence as set out in SEQ ID NO: 2, comprises at least one substitution of an amino acid residue corresponding to V129A and/or F194Y said positions being defined with reference to SEQ ID NO: 2; and wherein the variant has an increased sucrose tolerance at pH 5, compared with the reference polypeptide as set out in SEQ ID NO: 2.

In an embodiment of the alpha-amylase polypeptide variant according to the invention, said variant has at least 70% identity with the polypeptide sequence as set out in SEQ ID NO: 2,
which, when aligned with the sequence as set out in SEQ ID NO: 2, comprises at least one substitution of an amino acid residue corresponding to any of amino acids
15, 16, 45, 75, 94, 94, 129, 134, 174, 177, 178, 186, 194, 210, 234, 254, 281, 323, 325, 358, 371, 652, 13, 70, 72, 282, 283, 284, 261, 77, 88, 78, 134, 133,
said positions being defined with reference to SEQ ID NO: 2;
and wherein the variant has an increased sucrose compared with the reference polypeptide as set out in SEQ ID NO: 2 tolerance, while the specific activity of the variant has reduced by at most 10% as compared with the reference polypeptide.

In an aspect of this embodiment the specific activity of the variant has reduced by at most 20%, in an aspect by at most 30%, in an aspect by at most 40%, in an aspect by at most 50% as compared to the reference polypeptide. In a further aspect of this embodiment the specific activity of the variant is at least the same or has increased compared to the reference polypeptide. In a further aspect of this embodiment the specific activity is determined using maltotriose as a substrate.

In an embodiment the alpha-amylase polypeptide variant according to the invention has an increased sucrose tolerance compared with the polypeptide as set out in SEQ ID NO: 2 and has at least 75%, in an aspect at least 80%, in an aspect at least 85%, in an aspect at least 90%, in an aspect at least 95%, in an aspect at least 96%, in an aspect at least 97% in an aspect at least 98%, in an aspect at least 99%, in an aspect at least 99.5% identity with the polypeptide sequence as set out in SEQ ID NO: 2, while the specific activity of the variant has reduced by at most 10% as compared with the reference polypeptide.

In an aspect of this embodiment the specific activity of the variant has reduced by at most 20%, in an aspect by at most 30%, in an aspect by at most 40%, in an aspect by at most 50% as compared to the reference polypeptide. In a further aspect of this embodiment the specific activity of the variant is at least the same or has increased compared to the reference polypeptide. In a further aspect of this embodiment the specific activity is determined using maltotriose as a substrate.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to any of amino acids 15, 16, 45, 75, 94, 94, 129, 134, 174, 177, 178, 186, 194, 210, 234, 254, 281, 323, 325, 358, 371, 652, 13, 70, 72, 282, 283, 284, 261, 133, said positions being defined with reference to SEQ ID NO: 2;

and wherein the variant has an increased sucrose tolerance compared with the reference polypeptide as set out in SEQ ID NO: 2, while the specific activity of the variant has reduced by at most 10% as compared with the reference polypeptide.

In an aspect of this embodiment the specific activity of the variant has reduced by at most 20%, in an aspect by at most 30%, in an aspect by at most 40%, in an aspect by at most 50% as compared to the reference polypeptide. In a further aspect of this embodiment the specific activity of the variant is at least the same or has increased compared to the reference polypeptide. In a further aspect of this embodiment the specific activity is determined using maltotriose as a substrate.

Thermostability at pH 5

Thermostability at pH 5 of a variant according to the invention may be expressed as the ratio of

[Residual Activity of a variant determined after an incubation at a temperature of above 37 degrees Celsius at pH 5] to [Activity of the variant determined after an incubation at a temperature of 37 degrees Celsius at pH 5], expressed as a percentage of the ratio of

[Residual Activity of a reference polypeptide having alpha-amylase activity after an incubation at a temperature of above 37 degrees Celsius at pH 5] to [Activity of the reference polypeptide having alpha-amylase activity after an incubation at a temperature of 37 degrees Celsius at pH 5].

Thermostability at pH 5 of a variant according to the invention may be expressed as the ratio of

[Residual Activity on maltotriose of a variant determined after an incubation at a temperature of above 37 degrees Celsius at pH 5] to [Activity on maltotriose of the variant determined after an incubation at a temperature of 37 degrees Celsius at pH 5], expressed as a percentage of the ratio of

[Residual Activity on maltotriose of a reference polypeptide having alpha-amylase activity after an incubation at a temperature of above 37 degrees Celsius at pH 5] to [Activity on maltotriose of the reference polypeptide having alpha-amylase activity after an incubation at a temperature of 37 degrees Celsius at pH 5].

In an aspect thermostability at pH 5 of a variant according to the invention may be expressed as the ratio of

[Activity of the variant in Assay 2C (as described herein)] to [Activity of the variant in Assay 2A (as described herein)], expressed as a percentage of the ratio of

[Activity of the reference polypeptide in Assay 2C (as described herein)] to [Activity of the reference polypeptide in Assay 2A (as described herein)].

The percentage thus obtained may be used as measure for the thermostability at pH 5 of the variant according to the invention. A thermostability at pH 5 of more than 100% shows that the variant has an increased thermostability at pH 5 compared to the reference polypeptide having alpha-amylase activity.

In an aspect of the invention the variant according to the invention has an increased thermostability at pH 5 compared with a reference polypeptide having alpha-amylase activity, preferably the reference polypeptide having alpha-amylase activity has an amino acid sequence as set out in SEQ ID NO: 2.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to any of amino acids 61, 75, 88, 133, 168, 188, 200, 222, 254, 264, 281, 327, 13, 70, 128, 282, 388, 261, said positions being defined with reference to SEQ ID NO: 2;

and wherein the variant has an increased Thermostability at pH5 compared with the reference polypeptide as set out in SEQ ID NO: 2.

In an embodiment the alpha-amylase polypeptide variant according to the invention has an increased Thermostability at pH5 compared with the polypeptide as set out in SEQ ID NO: 2 and has at least 75%, in an aspect at least 80%, in an aspect at least 85%, in an aspect at least 90%, in an aspect at least 95%, in an aspect at least 96%, in an aspect at least 97% in an aspect at least 98%, in an aspect at least 99%, in an aspect at least 99.5% identity with the polypeptide sequence as set out in SEQ ID NO: 2.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to L61F, L75F, G88A, S133T, F168Y, F188I, S200N, A222V, V254F, A264S, V281L, N327S, Q13E, W70Y, F128I, L282F, L282M, L282M, A388L, D261G, said positions being defined with reference to SEQ ID NO: 2;

and wherein the variant has an increased Thermostability at pH5 compared with the reference polypeptide as set out in SEQ ID NO: 2.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises substitution of an amino acid residue corresponding to amino acid 129 and/or 225, said positions being defined with reference to SEQ ID NO: 2; and wherein the variant has an increased Thermostability at pH5 compared with the reference polypeptide as set out in SEQ ID NO: 2.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises substitution of an amino acid residue corresponding to V129A and/or L225F, said positions being defined with reference to SEQ ID NO: 2; and wherein the variant has an increased Thermostability at pH5 compared with the reference polypeptide as set out in SEQ ID NO: 2.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to any of amino acids 61, 75, 88, 133, 168, 188, 200, 222, 254, 264, 281, 327, 13, 70, 128, 282, 388, 261, said positions being defined with reference to SEQ ID NO: 2;

and wherein the variant has an increased Thermostability at pH5 compared with the reference polypeptide as set out in SEQ ID NO: 2, while the specific activity of the variant has reduced by at most 10% as compared with the reference polypeptide.

In an aspect of this embodiment the specific activity of the variant has reduced by at most 20%, in an aspect by at most 30%, in an aspect by at most 40%, in an aspect by at most 50% as compared to the reference polypeptide. In a further aspect of this embodiment the specific activity of the variant is at least the same or has increased compared to the reference polypeptide. In a further aspect of this embodiment the specific activity is determined using maltotriose as a substrate.

In an embodiment the alpha-amylase polypeptide variant according to the invention has an increased Thermostability at pH5 compared with the polypeptide as set out in SEQ ID NO: 2 and has at least 75%, in an aspect at least 80%, in an aspect at least 85%, in an aspect at least 90%, in an aspect at least 95%, in an aspect at least 96%, in an aspect at least 97% in an aspect at least 98%, in an aspect at least 99%, in an aspect at least 99.5% identity with the polypeptide sequence as set out in SEQ ID NO: 2, while the specific activity of the variant has reduced by at most 10% as compared with the reference polypeptide.

In an aspect of this embodiment the specific activity of the variant has reduced by at most 20%, in an aspect by at most 30%, in an aspect by at most 40%, in an aspect by at most 50% as compared to the reference polypeptide. In a further aspect of this embodiment the specific activity of the variant is at least the same or has increased compared to the reference polypeptide. In a further aspect of this embodiment the specific activity is determined using maltotriose as a substrate.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to L61F, L75F, G88A, S133T, F168Y, F188I, S200N, A222V, V254F, A264S, V281L, N327S, Q13E, W70Y, F128I, L282F, L282M, L282M, A388L, D261G, said positions being defined with reference to SEQ ID NO: 2;

and wherein the variant has an increased Thermostability at pH5 compared with the reference polypeptide as set out in SEQ ID NO: 2, while the specific activity of the variant has reduced by at most 10% as compared with the reference polypeptide.

In an aspect of this embodiment the specific activity of the variant has reduced by at most 20%, in an aspect by at most 30%, in an aspect by at most 40%, in an aspect by at most 50% as compared to the reference polypeptide. In a further aspect of this embodiment the specific activity of the variant is at least the same or has increased compared to the reference polypeptide. In a further aspect of this embodiment the specific activity is determined using maltotriose as a substrate.

Activity at pH4:Activity to pH5 Ratio

Activity at pH 4 and Activity at pH 5 may be determined using a suitable assay such as the NBAU assay or Maltotriose assay as described herein and adjusting the pH accordingly.

Activity at pH4:Activity to pH5 ratio of a variant according to the invention may be expressed as the ratio of

[Activity of a variant determined at pH 4] to [Activity of the variant determined at pH 5], expressed as a percentage of the ratio of

[Activity of a reference polypeptide at pH 4] to [Activity of the reference polypeptide at a pH 5].

Activity at pH4:Activity to pH5 ratio of a variant according to the invention may be expressed as the ratio of

[Activity on maltotriose of a variant determined at pH 4] to [Activity on maltotriose of the variant determined at pH 5], expressed as a percentage of the ratio of

[Activity on maltotriose of a reference polypeptide at pH 4] to [Activity on maltotriose of the reference polypeptide at pH 5].

In an aspect Activity at pH4:Activity to pH5 ratio of a variant according to the invention may be expressed as the ratio of

[Activity of the variant in Assay 2D (as described herein)] to [Activity of the variant in Assay 2A (as described herein)], expressed as a percentage of the ratio of

[Activity on maltotriose of the reference polypeptide in Assay 2D (as described herein)] to [Activity on maltotriose of the reference polypeptide in Assay 2A (as described herein)].

The percentage thus obtained may be used as measure for the Activity at pH4:Activity to pH5 ratio of the variant according to the invention. An Activity at pH4:Activity to pH5 ratio of more than 100% shows that the variant has an increased Activity at pH4:Activity to pH5 ratio compared to the reference polypeptide having alpha-amylase activity. that the variant has an increased Activity at pH4:Activity to pH5 ratio compared to the reference polypeptide having alpha-amylase activity.

An Activity at pH4:Activity to pH5 ratio of more than 100% may be used to demonstrate an altered pH profile in comparison with a parent polypeptide having alpha-amylase activity.

An Activity at pH4:Activity to pH5 ratio of more than 100% may be used to demonstrate an increased activity at different pH range in comparison with a parent polypeptide having alpha-amylase activity.

An Activity at pH4:Activity to pH5 ratio of more than 100% may be used to demonstrate a specific activity which is higher at at least one pH between pH 3 and pH 7, in comparison with a parent polypeptide having alpha-amylase activity.

In an aspect an Activity at pH4:Activity to pH5 ratio of more than 100% may be used to demonstrate a specific activity which is higher at at least one pH between pH 3 and pH 6, in comparison with a parent polypeptide having alpha-amylase activity.

In an aspect of the invention the variant according to the invention has an increased Activity at pH4:Activity to pH5 ratio compared with a reference polypeptide having alpha-amylase activity, preferably the reference polypeptide having alpha-amylase activity has an amino acid sequence as set out in SEQ ID NO: 2.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to any of amino acids 124, 126, 129, 136, 168, 186, 195, 199, 219, 222, 267, 269, 271, 288, 325, 331, 370, 377, 421, 450, 652, 20, 68, 72, 225, 282, 334, said positions being defined with reference to SEQ ID NO: 2;

and wherein the variant has an increased Activity at pH4:Activity to pH5 ratio compared with the reference polypeptide as set out in SEQ ID NO: 2.

In an embodiment the alpha-amylase polypeptide variant according to the invention has an increased Activity at pH4:Activity to pH5 ratio compared with the polypeptide as set out in SEQ ID NO: 2 and has at least 75%, in an aspect at least 80%, in an aspect at least 85%, in an aspect at least 90%, in an aspect at least 95%, in an aspect at least 96%, in an aspect at least 97% in an aspect at least 98%, in an aspect at least 99%, in an aspect at least 99.5% identity with the polypeptide sequence as set out in SEQ ID NO: 2.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to V124I, V126I, V129A, F136A, F168Y, K186Q, S195A, L199F, A219D, A222V, A222I, H267N, E269D, V271T, T288S, T288N, I325F, S331 D, G370N, G377A, I421V, T450S, F652I, Y20L, Y20V, T68A, T68G, S72T, L225F, L282I, L282M, L334H, said positions being defined with reference to SEQ ID NO: 2;

and wherein the variant has an increased Activity at pH4:Activity to pH5 ratio compared with the reference polypeptide as set out in SEQ ID NO: 2.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises substitution of an amino acid residue corresponding to amino acid 129 and/or 225, said positions being defined with reference to SEQ ID NO: 2; and wherein the variant has an increased Activity at pH4:Activity to pH5 ratio compared with the reference polypeptide as set out in SEQ ID NO: 2.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises substitution of an amino acid residue corresponding to V129A and/or L225F, said positions being defined with reference to SEQ ID NO: 2; and wherein the variant has an increased Activity at pH4:Activity to pH5 ratio compared with the reference polypeptide as set out in SEQ ID NO: 2.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to any of amino acids 124, 126, 129, 136, 168, 186, 195, 199, 219, 222, 267, 269, 271, 288, 325, 331, 370, 377, 421, 450, 652, 20, 68, 72, 225, 282, 334, said positions being defined with reference to SEQ ID NO: 2;

and wherein the variant has an increased Activity at pH4:Activity to pH5 ratio compared with the reference polypeptide as set out in SEQ ID NO: 2, while the specific activity of the variant has reduced by at most 10% as compared with the reference polypeptide.

In an aspect of this embodiment the specific activity of the variant has reduced by at most 20%, in an aspect by at most 30%, in an aspect by at most 40%, in an aspect by at most 50% as compared to the reference polypeptide. In a further aspect of this embodiment the specific activity of the variant is at least the same or has increased compared to the reference polypeptide. In a further aspect of this embodiment the specific activity is determined using maltotriose as a substrate.

In an embodiment the alpha-amylase polypeptide variant according to the invention has an increased Activity at pH4:Activity to pH5 ratio compared with the polypeptide as set out in SEQ ID NO: 2 and has at least 75%, in an aspect at least 80%, in an aspect at least 85%, in an aspect at least 90%, in an aspect at least 95%, in an aspect at least 96%, in an aspect at least 97% in an aspect at least 98%, in an aspect at least 99%, in an aspect at least 99.5% identity with the polypeptide sequence as set out in SEQ ID NO: 2, while the specific activity of the variant has reduced by at most 10% as compared with the reference polypeptide.

In an aspect of this embodiment the specific activity of the variant has reduced by at most 20%, in an aspect by at most 30%, in an aspect by at most 40%, in an aspect by at most 50% as compared to the reference polypeptide. In a further aspect of this embodiment the specific activity of the variant is at least the same or has increased compared to the reference polypeptide. In a further aspect of this embodiment the specific activity is determined using maltotriose as a substrate.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to V124I, V126I, V129A, F136A, F168Y, K186Q, S195A, L199F, A219D, A222V, A222I, H267N, E269D, V271T, T288S, T288N, I325F, S331 D, G370N, G377A, I421V, T450S, F652I, Y20L, Y20V, T68A, T68G, S72T, L225F, L282I, L282M, L334H, said positions being defined with reference to SEQ ID NO: 2;

and wherein the variant has an increased Activity at pH4:Activity to pH5 ratio compared with the reference polypeptide as set out in SEQ ID NO: 2, while the specific activity of the variant has reduced by at most 10% as compared with the reference polypeptide.

In an aspect of this embodiment the specific activity of the variant has reduced by at most 20%, in an aspect by at most 30%, in an aspect by at most 40%, in an aspect by at most 50% as compared to the reference polypeptide. In a further aspect of this embodiment the specific activity of the variant is at least the same or has increased compared to the reference polypeptide. In a further aspect of this embodiment the specific activity is determined using maltotriose as a substrate.

Thermostability at pH 4

Thermostability at pH 4 of a variant according to the invention may be expressed as the ratio of

[Residual Activity of a variant determined after an incubation at a temperature of above 37 degrees Celsius at pH 4] to [Activity of the variant determined after an incubation at a temperature of 37 degrees Celsius at pH 4], expressed as a percentage of the ratio of

[Activity of a reference polypeptide after an incubation temperature of above 37 degrees Celsius at pH 4] to [Activity of the reference polypeptide after an incubation at a temperature of 37 degrees Celsius at pH 4].

Thermostability at pH 4 of a variant according to the invention may be expressed as the ratio of

[Residual Activity on maltotriose of a variant determined after an incubation at a temperature of above 37 degrees Celsius at pH 4] to [Activity on maltotriose of the variant determined after an incubation at a temperature of 37 degrees Celsius at pH 4], expressed as a percentage of the ratio of

[Activity on maltotriose of a reference polypeptide after an incubation temperature of above 37 degrees Celsius at pH 4] to [Activity on maltotriose of the reference polypeptide after an incubation at a temperature of 37 degrees Celsius at pH 4].

In an aspect thermostability at pH 4 of a variant according to the invention may be expressed as the ratio of

[Activity of the variant in Assay 2E (as described herein)] to [Activity of the variant in Assay 2A (as described herein)], expressed as a percentage of the ratio of

[Activity of the reference polypeptide in Assay 2E (as described herein)] to [Activity of the reference polypeptide in Assay 2A (as described herein)].

The percentage thus obtained may be used as measure for the thermostability at pH 4 of the variant according to the invention. A thermostability at pH 4 of more than 100% shows that the variant has an increased thermostability at pH 4 compared to the reference polypeptide having alpha-amylase activity.

In an aspect of the invention the variant according to the invention has an increased thermostability at pH 4 compared with a reference polypeptide having alpha-amylase activity, preferably the reference polypeptide having alpha-amylase activity has an amino acid sequence as set out in SEQ ID NO: 2.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to any of amino acids 88, 188, 200, 222, 70, 282, said positions being defined with reference to SEQ ID NO: 2;

and wherein the variant has an increased thermostability at pH 4 compared with the reference polypeptide as set out in SEQ ID NO: 2.

In an embodiment the alpha-amylase polypeptide variant according to the invention has an increased thermostability at pH 4 compared with the polypeptide as set out in SEQ ID NO: 2 and has at least 75%, in an aspect at least 80%, in an aspect at least 85%, in an aspect at least 90%, in an aspect at least 95%, in an aspect at least 96%, in an aspect at least 97% in an aspect at least 98%, in an aspect at least 99%, in an aspect at least 99.5% identity with the polypeptide sequence as set out in SEQ ID NO: 2.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to

G88A, F188I, S200N, A222V, W70Y, L282F, L282I, L282M, L282T, L282M, said positions being defined with reference to SEQ ID NO: 2;

and wherein the variant has an increased thermostability at pH 4 compared with the reference polypeptide as set out in SEQ ID NO: 2.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to any of amino acids 70, 188, 281, 282, said positions being defined with reference to SEQ ID NO: 2;

and wherein the variant has an increased thermostability at pH 4 compared with the reference polypeptide as set out in SEQ ID NO: 2.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to

W70Y, F188I, L282F, said positions being defined with reference to SEQ ID NO: 2;

and wherein the variant has an increased thermostability at pH 4 compared with the reference polypeptide as set out in SEQ ID NO: 2.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to any of amino acids 88, 188, 200, 222, 70, 282, said positions being defined with reference to SEQ ID NO: 2;

and wherein the variant has an increased thermostability at pH 4 compared with the reference polypeptide as set out in SEQ ID NO: 2, while the specific activity of the variant has reduced by at most 10% as compared with the reference polypeptide.

In an aspect of this embodiment the specific activity of the variant has reduced by at most 20%, in an aspect by at most 30%, in an aspect by at most 40%, in an aspect by at most 50% as compared to the reference polypeptide. In a further aspect of this embodiment the specific activity of the variant is at least the same or has increased compared to the reference polypeptide. In a further aspect of this embodiment the specific activity is determined using maltotriose as a substrate.

In an embodiment the alpha-amylase polypeptide variant according to the invention has an increased thermostability at pH 4 compared with the polypeptide as set out in SEQ ID NO: 2 and has at least 75%, in an aspect at least 80%, in an aspect at least 85%, in an aspect at least 90%, in an aspect at least 95%, in an aspect at least 96%, in an aspect at least 97% in an aspect at least 98%, in an aspect at least 99%, in an aspect at least 99.5% identity with the polypeptide sequence as set out in SEQ ID NO: 2, while the specific activity of the variant has reduced by at most 10% as compared with the reference polypeptide.

In an aspect of this embodiment the specific activity of the variant has reduced by at most 20%, in an aspect by at most 30%, in an aspect by at most 40%, in an aspect by at most 50% as compared to the reference polypeptide. In a further aspect of this embodiment the specific activity of the variant is at least the same or has increased compared to the reference polypeptide. In a further aspect of this embodiment the specific activity is determined using maltotriose as a substrate.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to

G88A, F188I, S200N, A222V, W70Y, L282F, L282I, L282M, L282T, L282M, said positions being defined with reference to SEQ ID NO: 2;

and wherein the variant has an increased thermostability at pH 4 compared with the reference polypeptide as set out in SEQ ID NO: 2, while the specific activity of the variant has reduced by at most 10% as compared with the reference polypeptide.

In an aspect of this embodiment the specific activity of the variant has reduced by at most 20%, in an aspect by at most 30%, in an aspect by at most 40%, in an aspect by at most 50% as compared to the reference polypeptide. In a further aspect of this embodiment the specific activity of the variant is at least the same or has increased compared to the reference polypeptide. In a further aspect of this embodiment the specific activity is determined using maltotriose as a substrate.

Thermostability in the Presence of Sucrose

Thermostability in the presence of sucrose of a variant according to the invention may be expressed as the ratio of

[Residual Activity of a variant determined after incubation in the presence of sucrose at a temperature of above 37 degrees Celsius] to [Activity of the variant determined after incubation in the absence of sucrose at a temperature of 37 degrees Celsius], expressed as a percentage of the ratio of

[Residual Activity of a reference polypeptide having alpha-amylase activity determined after incubation in the presence of sucrose at a temperature of above 37 degrees Celsius] to [Activity of the reference polypeptide having alpha-amylase activity determined after incubation in the absence of sucrose at a temperature of 37 degrees Celsius].

Thermostability in the presence of sucrose of a variant according to the invention may be expressed as the ratio of

[Residual Activity on maltotriose of a variant determined after incubation in the presence of sucrose at a temperature of above 37 degrees Celsius] to [Activity on maltotriose of the variant determined after incubation in the absence of sucrose at a temperature of 37 degrees Celsius], expressed as a percentage of the ratio of

[Residual Activity on maltotriose of a reference polypeptide having alpha-amylase activity determined after incubation in the presence of sucrose at a temperature of above 37 degrees Celsius] to [Activity on maltotriose of the reference polypeptide having alpha-amylase activity determined after incubation in the absence of sucrose at a temperature of 37 degrees Celsius].

In an aspect thermostability in the presence of sucrose of a variant according to the invention may be expressed as the ratio of

[Residual Activity of the variant in Assay 2F (as described herein)] to [Activity on of the variant in Assay 2A (as described herein)], expressed as a percentage of the ratio of

[Residual Activity on maltotriose of the reference polypeptide in Assay 2F (as described herein)] to [Activity on maltotriose of the reference polypeptide in Assay 2A (as described herein)].

The percentage thus obtained may be used as measure for the thermostability in the presence of sucrose of the variant according to the invention. A thermostability in the presence of sucrose of more than 100% shows that the variant has an increased thermostability in the presence of sucrose compared to the reference polypeptide having alpha-amylase activity.

In an aspect of the invention the variant according to the invention has an increased thermostability in the presence of sucrose compared with a reference polypeptide having alpha-amylase activity, preferably the reference polypeptide having alpha-amylase activity has an amino acid sequence as set out in SEQ ID NO: 2.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to any of amino acids 61, 75, 133, 168, 188, 200, 254, 264, 281, 327, 371, 68, 70, 282, 388, 261, said positions being defined with reference to SEQ ID NO: 2;

and wherein the variant has an increased thermostability in the presence of sucrose compared with the reference polypeptide as set out in SEQ ID NO: 2.

In an embodiment the alpha-amylase polypeptide variant according to the invention has an increased thermostability in the presence of sucrose compared with the polypeptide as set out in SEQ ID NO: 2 and has at least 75%, in an aspect at least 80%, in an aspect at least 85%, in an aspect at least 90%, in an aspect at least 95%, in an aspect at least 96%, in an aspect at least 97% in an aspect at least 98%, in an aspect at least 99%, in an aspect at least 99.5% identity with the polypeptide sequence as set out in SEQ ID NO: 2.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to L61F, L75F, S133T, F168Y, F188I, S200N, V254F, A264S, V281L, N327S, N371G, T68A, W70Y, L282F, L282I, L282M, L282T, L282M, A388L, D261G, said positions being defined with reference to SEQ ID NO: 2;

and wherein the variant has an increased thermostability in the presence of sucrose compared with the reference polypeptide as set out in SEQ ID NO: 2.

In an aspect of the invention the variant according to the invention has an increased thermostability in the presence of sucrose at pH 5 compared with a reference polypeptide having alpha-amylase activity, preferably the reference polypeptide having alpha-amylase activity has an amino acid sequence as set out in SEQ ID NO: 2.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to any of amino acids 61, 75, 133, 168, 188, 200, 254, 264, 281, 327, 371, 68, 70, 282, 388, 261, said positions being defined with reference to SEQ ID NO: 2;

and wherein the variant has an increased thermostability in the presence of sucrose at pH 5 compared with the reference polypeptide as set out in SEQ ID NO: 2.

In an embodiment the alpha-amylase polypeptide variant according to the invention has an increased thermostability in the presence of sucrose at pH 5 compared with the polypeptide as set out in SEQ ID NO: 2 and has at least 75%, in an aspect at least 80%, in an aspect at least 85%, in an aspect at least 90%, in an aspect at least 95%, in an aspect at least 96%, in an aspect at least 97% in an aspect at least 98%, in an aspect at least 99%, in an aspect at least 99.5% identity with the polypeptide sequence as set out in SEQ ID NO: 2.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to L61F, L75F, S133T, F168Y, F188I, S200N, V254F, A264S, V281L, N327S, N371G, T68A, W70Y, L282F, L282I, L282M, L282T, L282M, A388L, D261G, said positions being defined with reference to SEQ ID NO: 2;

and wherein the variant has an increased thermostability in the presence of sucrose at pH 5 compared with the reference polypeptide as set out in SEQ ID NO: 2.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to any of amino acids 70, 188, 200, 254, 282, said positions being defined with reference to SEQ ID NO: 2;

and wherein the variant has an increased thermostability in the presence of sucrose compared with the reference polypeptide as set out in SEQ ID NO: 2.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to

W70Y, F188I, S200N, V254F, L282M, said positions being defined with reference to SEQ ID NO: 2;

and wherein the variant has an increased thermostability in the presence of sucrose compared with the reference polypeptide as set out in SEQ ID NO: 2.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to any of amino acids 70, 188, 200, 254, 282, said positions being defined with reference to SEQ ID NO: 2;

and wherein the variant has an increased thermostability in the presence of sucrose at pH5 compared with the reference polypeptide as set out in SEQ ID NO: 2.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to

W70Y, F188I, S200N, V254F, L282M, said positions being defined with reference to SEQ ID NO: 2;

and wherein the variant has an increased thermostability in the presence of sucrose at pH 5 compared with the reference polypeptide as set out in SEQ ID NO: 2.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to any of amino acids 61, 75, 133, 168, 188, 200, 254, 264, 281, 327, 371, 68, 70, 282, 388, 261, said positions being defined with reference to SEQ ID NO: 2;

and wherein the variant has an increased thermostability in the presence of sucrose compared with the reference polypeptide as set out in SEQ ID NO: 2, while the specific activity of the variant has reduced by at most 10% as compared with the reference polypeptide.

In an aspect of this embodiment the specific activity of the variant has reduced by at most 20%, in an aspect by at most 30%, in an aspect by at most 40%, in an aspect by at most 50% as compared to the reference polypeptide. In a further aspect of this embodiment the specific activity of the variant is at least the same or has increased compared to the reference polypeptide. In a further aspect of this embodiment the specific activity is determined using maltotriose as a substrate.

In an embodiment the alpha-amylase polypeptide variant according to the invention has an increased thermostability in the presence of sucrose compared with the polypeptide as set out in SEQ ID NO: 2 and has at least 75%, in an aspect at least 80%, in an aspect at least 85%, in an aspect at least 90%, in an aspect at least 95%, in an aspect at least 96%, in an aspect at least 97% in an aspect at least 98%, in an aspect at least 99%, in an aspect at least 99.5% identity with the polypeptide sequence as set out in SEQ ID NO: 2, while the specific activity of the variant has reduced by at most 10% as compared with the reference polypeptide.

In an aspect of this embodiment the specific activity of the variant has reduced by at most 20%, in an aspect by at most 30%, in an aspect by at most 40%, in an aspect by at most 50% as compared to the reference polypeptide. In a further aspect of this embodiment the specific activity of the variant is at least the same or has increased compared to the reference polypeptide. In a further aspect of this embodiment the specific activity is determined using maltotriose as a substrate.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to L61F, L75F, S133T, F168Y, F188I, S200N, V254F, A264S, V281L, N327S, N371G, T68A, W70Y, L282F, L282I, L282M, L282T, L282M, A388L, D261G, said positions being defined with reference to SEQ ID NO: 2;

and wherein the variant has an increased thermostability in the presence of sucrose compared with the reference polypeptide as set out in SEQ ID NO: 2, while the specific activity of the variant has reduced by at most 10% as compared with the reference polypeptide.

In an aspect of this embodiment the specific activity of the variant has reduced by at most 20%, in an aspect by at most 30%, in an aspect by at most 40%, in an aspect by at most 50% as compared to the reference polypeptide. In a further aspect of this embodiment the specific activity of the variant is at least the same or has increased compared to the reference polypeptide. In a further aspect of this embodiment the specific activity is determined using maltotriose as a substrate.

Activity at different pH (determine pH optimum) may be determined by measuring the activity in a pH range (e.g. 2-12)

Product spectrum may be determined by measuring the amount of different oligosaccharides formed from starch, for example using HPLC.

Activity on raw starch may be determined by incubating the enzyme with a suspension of native starch (e.g. wheat or maize), followed by centrifuging to remove starch granules, and determining the amount of reducing sugars released (e.g. with DNS method)

Altered temperature optimum may be determined by measuring activity as described above over a temperature range (e.g. 50-100° C.).

Substrate specificity may be determined by measuring activity as described above on different substrates.

The present invention also relates to methods for preparing a dough or a baked product comprising incorporating into the dough an effective amount of the alpha-amylase variant, which improves one or more properties of the dough or the baked product obtained from the dough relative to a dough or a baked product in which a parent polypeptide is incorporated.

The phrase "incorporating into the dough" is defined herein as adding the alpha-amylase variant or a parent polypeptide to the dough, any ingredient from which the dough is to be made, and/or any mixture of dough ingredients from which the dough is to be made. In other words, the alpha-amylase variant or a parent polypeptide may be added in any step of the dough preparation and may be added in one, two or more steps. The alpha-amylase variant or a parent polypeptide to the dough are added to the ingredients of a dough that is kneaded and baked to make the baked product using methods well known in the art. See, for example, U.S. Pat. No. 4,567,046, EP-A-426, 211, JP-A-60-78529, JP-A-62-111629, and JP-A-63-258528.

The term "effective amount" is defined herein as an amount of the alpha-amylase variant that is sufficient for providing a measurable effect on at least one property of interest of the dough and/or baked product. A suitable amount of alpha-amylase variant is in a range of 0.5-1500 NBAU/kg flour, in an embodiment 5-200 NBAU/kg flour, in a further embodiment 20-100 NBAU/kg flour. A suitable amount includes 1 ppm-2000 ppm of an enzyme having an activity in a range of about 700 to 1100 NBAU/g. In an embodiment an effective amount is in a range of 10-200 ppm of an enzyme having an activity in a range of about 700 to 1100 NBAU/g, in another embodiment 30-100 ppm of an enzyme having an activity in a range of about 700 to 1100 NBAU/g. In an embodiment an effective amount is in a range of 10-200 ppm of an enzyme having an activity of about 700 to 1100 NBAU/g. Herein and hereinafter NBAU stands for New Baking Amylase Unit as defined in the examples under the heading NBAU Assay The term "improved property" is defined herein as any property of a dough and/or a product obtained from the dough, particularly a baked product, which is improved by the action of the alpha-amylase variant, the composition according to the invention or the pre-mix according to the invention relative to a dough or product in which a parent polypeptide is incorporated. The improved property may include, but is not limited to, increased strength of the dough, increased elasticity of the dough, increased stability of the dough, reduced stickiness of the dough, improved extensibility of the dough, improved machineability of the dough, increased volume of the baked product, improved flavour of the baked product, improved crumb structure of the baked product, improved crumb softness of the baked product, reduced blistering of the baked product, improved crispiness, improved resilience both initial and in particular after storage, reduced hardness after storage and/or improved anti-staling of the baked product.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to any of amino acids 13, 61, 68, 70, 75, 88, 128, 133, 168, 188, 200, 222, 254, 261, 264, 281, 282, 327, 371, 388, said positions being defined with reference to SEQ ID NO: 2;

and wherein the variant provides improved anti-staling to a baked product compared with the reference polypeptide as set out in SEQ ID NO: 2.

In an embodiment the alpha-amylase polypeptide variant according to the invention provides improved anti-staling to a baked product compared with the polypeptide as set out in SEQ ID NO: 2 and has at least 75%, in an aspect at least 80%, in an aspect at least 85%, in an aspect at least 90%, in an aspect at least 95%, in an aspect at least 96%, in an aspect at least 97% in an aspect at least 98%, in an aspect at least 99%, in an aspect at least 99.5% identity with the polypeptide sequence as set out in SEQ ID NO: 2.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to Q13E, L61F, T68A, W70Y, L75F, G88A, F128I, S133T, F168Y, F188I, S200N, A222V, V254F, D261G, A264S, V281L, L282F, L282M, L282I, L282T, N327S, N371G, A388L, said positions being defined with reference to SEQ ID NO: 2;

and wherein the variant provides improved anti-staling to a baked product compared with the reference polypeptide as set out in SEQ ID NO: 2.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to any of amino acids 13, 61, 68, 70, 75, 88, 128, 133, 168, 188, 200, 222, 254, 261, 264, 281, 282, 327, 371, 388, said positions being defined with reference to SEQ ID NO: 2;

and wherein the variant provides a further reduced hardness after storage to a baked product compared with the reference polypeptide as set out in SEQ ID NO: 2.

In an embodiment the alpha-amylase polypeptide variant according to the invention provides a further reduced hardness after storage to a baked product compared with the polypeptide as set out in SEQ ID NO: 2 and has at least 75%, in an aspect at least 80%, in an aspect at least 85%, in an aspect at least 90%, in an aspect at least 95%, in an aspect at least 96%, in an aspect at least 97% in an aspect at least 98%, in an aspect at least 99%, in an aspect at least 99.5% identity with the polypeptide sequence as set out in SEQ ID NO: 2.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to Q13E, L61F, T68A, W70Y, L75F, G88A, F128I, S133T, F168Y, F188I, S200N, A222V, V254F, D261G, A264S, V281L, L282F, L282M, L282I, L282T, N327S, N371G, A388L, said positions being defined with reference to SEQ ID NO: 2;

and wherein the variant provides a further reduced hardness after storage to a baked product compared with the reference polypeptide as set out in SEQ ID NO: 2.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to any of amino acids 13, 61, 68, 70, 75, 88, 128, 133, 168, 188, 200, 222, 254, 261, 264, 281, 282, 327, 371, 388, said positions being defined with reference to SEQ ID NO: 2;

and wherein the variant provides a further decreased loss of resilience after storage to a baked product compared with the reference polypeptide as set out in SEQ ID NO: 2.

In an embodiment the alpha-amylase polypeptide variant according to the invention provides a further decreased loss of resilience after storage to a baked product compared with the polypeptide as set out in SEQ ID NO: 2 and has at least 75%, in an aspect at least 80%, in an aspect at least 85%, in an aspect at least 90%, in an aspect at least 95%, in an aspect at least 96%, in an aspect at least 97% in an aspect at least 98%, in an aspect at least 99%, in an aspect at least 99.5% identity with the polypeptide sequence as set out in SEQ ID NO: 2.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to Q13E, L61F, T68A, W70Y, L75F, G88A, F128I, S133T, F168Y, F188I, S200N, A222V, V254F, D261G, A264S, V281L, L282F, L282M, L282I, L282T, N327S, N371G, A388L, said positions being defined with reference to SEQ ID NO: 2;

and wherein the variant provides a further decreased loss of resilience after storage to a baked product compared with the reference polypeptide as set out in SEQ ID NO: 2.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to any of amino acids 13, 61, 68, 70, 75, 88, 128, 133, 168, 188, 200, 222, 254, 261, 264, 281, 282, 327, 371, 388, said positions being defined with reference to SEQ ID NO: 2;

and wherein the variant further retards staling of a baked product compared with the reference polypeptide as set out in SEQ ID NO: 2.

In an embodiment the alpha-amylase polypeptide variant according to the invention further retards staling of a baked product compared with the polypeptide as set out in SEQ ID NO: 2 and has at least 75%, in an aspect at least 80%, in an aspect at least 85%, in an aspect at least 90%, in an aspect at least 95%, in an aspect at least 96%, in an aspect at least 97% in an aspect at least 98%, in an aspect at least 99%, in an aspect at least 99.5% identity with the polypeptide sequence as set out in SEQ ID NO: 2.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to Q13E, L61F, T68A, W70Y, L75F, G88A, F128I, S133T, F168Y, F188I, S200N, A222V, V254F, D261G, A264S, V281L, L282F, L282M, L282I, L282T, N327S, N371G, A388L, said positions being defined with reference to SEQ ID NO: 2;

and wherein the variant further retards staling of a baked product compared with the reference polypeptide as set out in SEQ ID NO: 2.

The improved property may include faster dough development time of the dough and/or reduced dough stickiness of the dough.

The improved property may include improved foldability of the baked product, such as improved foldability of a tortilla, a pancake, a flat bread, a pizza crust, a roti and/or a slice of bread.

The improved property may include improved flexibility of the baked product including improved flexibility of a tortilla, a pancake, a flat bread, a pizza crust, a roti and/or a slice of bread.

The improved property may include improved stackability of flat baked products including tortillas, pancakes, flat breads, pizza crusts, roti.

The improved property may include reduced stickiness of noodles and/or increased flexibility of noodles.

The improved property may include reduced clumping of cooked noodles and/or improved flavor of noodles even after a period of storage.

The improved property may include reduction of formation of hairline cracks in a product in crackers as well as creating a leavening effect and improved flavor development.

The improved property may include improved mouth feel and/or improved softness on squeeze.

The improved property may include reduced damage during transport, including reduced breaking during transport.

The improved property may include reduced hardness after storage of gluten-free bread.

The improved property may include improved resilience of gluten-free bread. The improved property may include improved resilience both initial and in particular after storage of gluten-free bread.

The improved property may include reduced hardness after storage of rye bread.

The improved property may include reduced loss of resilience over storage of rye bread, The improved property may include reduced loss of resilience over storage of a baked product comprising at least 5 wt % sugar, in an aspect comprising at least 8 wt % sugar, in an aspect comprising at least 12 wt % sugar, in an aspect comprising at least 15 wt % sugar based on flour. In an aspect comprising at least 18 wt % sugar, in an aspect comprising at least 20 wt % sugar, in an aspect comprising at least 25 wt % sugar, in an aspect comprising at least 30 wt % sugar based on flour. Herein 5 wt % sugar means 50 grams sugar per 1000 gram of flour used in the recipe, etc.

The improved property may include reduced hardness after storage of a baked product comprising at least 5 wt % sugar, in an aspect comprising at least 8 wt % sugar, in an aspect comprising at least 12 wt % sugar, in an aspect comprising at least 15 wt % sugar based on flour. In an aspect comprising at least 18 wt % sugar, in an aspect comprising aspect at least 20 wt % sugar, in an aspect comprising at least 25 wt % sugar, in an aspect comprising at least 30 wt % sugar based on flour. Herein 5 wt % sugar means 50 grams sugar per 1000 gram of flour used in the recipe, etc.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to any of amino acids 15, 16, 45, 75, 94, 94, 129, 134, 174, 177, 178, 186, 194, 210, 234, 254, 281, 323, 325, 358, 371, 652, 13, 70, 72, 282, 283, 284, 261, 133, said positions being defined with reference to SEQ ID NO: 2;

and wherein the variant provides a further reduced hardness after storage to a baked product, said baked product comprising at least 5 wt % sugar, as compared with the reference polypeptide as set out in SEQ ID NO: 2. In an further aspect of this embodiment the baked product comprises at least 8 wt % sugar, in an aspect at least 12 wt % sugar, in an aspect at least 15 wt % sugar based on flour. In a further aspect of this embodiment the baked product comprises at least 18 wt % sugar, in an aspect at least 20 wt % sugar, in an aspect at least 25 wt % sugar, in an aspect at least 30 wt % sugar based on flour.

In an embodiment the alpha-amylase polypeptide variant according to the invention a further reduced hardness after storage to a baked product, said baked product comprising at least 5 wt % sugar, compared with the polypeptide as set out in SEQ ID NO: 2 and has at least 75%, in an aspect at least 80%, in an aspect at least 85%, in an aspect at least 90%, in an aspect at least 95%, in an aspect at least 96%, in an aspect at least 97% in an aspect at least 98%, in an aspect at least 99%, in an aspect at least 99.5% identity with the polypeptide sequence as set out in SEQ ID NO: 2. In an further aspect of this embodiment the baked product comprises at least 8 wt % sugar, in an aspect at least 12 wt % sugar, in an aspect at least 15 wt % sugar based on flour. In a further aspect of this embodiment the baked product comprises at least 18 wt % sugar, in an aspect at least 20 wt % sugar, in an aspect at least 25 wt % sugar, in an aspect at least 30 wt % sugar based on flour.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to I15V, I16T, M45L, L75V, T94A, T94P, V129A, T134S, I174L, W177F, D178N, K186Q, F194Y, L210F, N234P, V254F, V281L, T323N, I325F, S358A, N371G, F652I, Q13E, W70Y, S72T, L282F, L282M, L282T, D283N, D283S, F284W, D261G, S133L, said positions being defined with reference to SEQ ID NO: 2;

and wherein the variant a further reduced hardness after storage to a baked product, said baked product comprising at least 5 wt % sugar compared with the reference polypeptide as set out in SEQ ID NO: 2. In an further aspect of this embodiment the baked product comprises at least 8 wt % sugar, in an aspect at least 12 wt % sugar, in an aspect at least 15 wt % sugar based on flour. In a further aspect of this embodiment the baked product comprises at least 18 wt % sugar, in an aspect at least 20 wt % sugar, in an aspect at least 25 wt % sugar, in an aspect at least 30 wt % sugar based on flour.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to any of amino acids 15, 16, 45, 75, 94, 94, 129, 134, 174, 177, 178, 186, 194, 210, 234, 254, 281, 323, 325, 358, 371, 652, 13, 70, 72, 282, 283, 284, 261, 133, said positions being defined with reference to SEQ ID NO: 2;

and wherein the variant provides a further decreased loss of resilience after storage to a baked product, said baked product comprising at least 5 wt % sugar, as compared with the reference polypeptide as set out in SEQ ID NO: 2. In an further aspect of this embodiment the baked product comprises at least 8 wt % sugar, in an aspect at least 12 wt % sugar, in an aspect at least 15 wt % sugar based on flour. In a further aspect of this embodiment the baked product comprises at least 18 wt % sugar, in an aspect at least 20 wt % sugar, in an aspect at least 25 wt % sugar, in an aspect at least 30 wt % sugar based on flour.

In an embodiment the alpha-amylase polypeptide variant according to the invention a further decreased loss of resilience to a baked product, said baked product comprising at least 5 wt % sugar, compared with the polypeptide as set out in SEQ ID NO: 2 and has at least 75%, in an aspect at least 80%, in an aspect at least 85%, in an aspect at least 90%, in an aspect at least 95%, in an aspect at least 96%, in an aspect at least 97% in an aspect at least 98%, in an aspect at least 99%, in an aspect at least 99.5% identity with the polypeptide sequence as set out in SEQ ID NO: 2. In an further aspect of this embodiment the baked product comprises at least 8 wt % sugar, in an aspect at least 12 wt % sugar, in an aspect at least 15 wt % sugar based on flour. In a further aspect of this embodiment the baked product comprises at least 18 wt % sugar, in an aspect at least 20 wt % sugar, in an aspect at least 25 wt % sugar, in an aspect at least 30 wt % sugar based on flour.

In an embodiment of the alpha-amylase polypeptide variant according to the invention, said variant has at least 70% identity with the polypeptide sequence as set out in SEQ ID NO: 2, which, when aligned with the sequence as set out in SEQ ID NO: 2, comprises at least one substitution of an amino acid residue corresponding to I15V, I16T, M45L, L75V, T94A, T94P, V129A, T134S, I174L, W177F, D178N, K186Q, F194Y, L210F, N234P, V254F, V281L, T323N, I325F, S358A, N371G, F652I, Q13E, W70Y, S72T, L282F, L282M, L282T, D283N, D283S, F284W, D261G, S133L, said positions being defined with reference to SEQ ID NO: 2;

and wherein the variant a further decreased loss of resilience after storage to a baked product, said baked product comprising at least 5 wt % sugar compared with the reference polypeptide as set out in SEQ ID NO: 2. In an further aspect of this embodiment the baked product comprises at least 8 wt % sugar, in an aspect at least 12 wt % sugar, in an aspect at least 15 wt % sugar based on flour. In a further aspect of this embodiment the baked product comprises at least 18 wt % sugar, in an aspect at least 20 wt % sugar, in an aspect at least 25 wt % sugar, in an aspect at least 30 wt % sugar based on flour.

Improved mouth feel includes sense of softness on an initial bite or after chewing, preferably without a sticky feeling in the mouth and/or without the baked product sticking to the teeth. Improved mouth feel includes the baked product feeling less dry in the mouth on an initial bite or after chewing. Improved mouth feel includes the baked product feeling less dry in the mouth on an initial bite or after chewing after it has been kept outside its packaging or container. The improved property may include that after a slice of bread was taken from its packaging or container and exposed to ambient conditions for 5 minutes, in an aspect for 10 minutes, in an aspect for 20 minutes it has improved mouthfeel.

The improved property may include that after a the cookie was taken from its packaging or container and exposed to ambient conditions for 10 minutes, in an aspect for 20 minutes, in an aspect for 30 minutes, in an aspect an hour it has improved mouthfeel.

In an aspect ambient conditions herein and herein after include a temperature of 20 degrees C. and a moisture level of 40% humidity.

Reduced breaking during transport includes the baked product, including without limitation cookies, bread such as gluten free bread, does not break in additional pieces as a consequence of transport.

Improved softness on squeeze includes the tactile experience that if a bun is held between the fingers and the thumb of a hand and the thumb and fingers are moved towards each other it takes less force.

Improved foldability of a baked product may be determined as follows.

The baked product is laid on a flat surface. The baked product is folded by picking up one edge of the product and placing it on the opposite edge of the product. This way a folded baked product is obtained having a bend curve in an area located at or close to the center. The surface of the outside of the bend of folded baked product is visually inspected. The foldability is improved if fewer cracks are observed at or close to the bend. This may be a particularly useful property if the baked product is a tortilla and/or a slice of bread.

Improved stackability may be determined as follows.

10 baked products are stacked on top of each other and sealed in a polymer package, such as polyethylene foil. This yields a pack of baked products. 10 packs of baked product are stacked on top of each other and kept under ambient conditions for 3 days, in an aspect for 5 days in an aspect for 1 week, in an aspect for 2 weeks. Ambient conditions are conditions as defined herein. After this period the bottom pack of baked products is opened, the baked products are separated from each other and the surfaces of the products are visually inspected. The stackability is improved if less surface damage is observed. Surface damage may be caused e.g. by rupture of the surface during separation of two baked products that were stacked on top of each other. This may be a particularly useful property if the baked product is a tortilla.

Faster dough development time may be determined as follows

Dough development time is the time the dough need to reach maximum consistency, maximum viscosity before gluten strands begin to break down. It may be determined by measuring peak time, using a Farinograph® from Brabender®, Germany. If a faronigraph is used to determine dough development time, dough development time is the time between the moment water is added and the moment the curve reaches its highest point. Peak time is preferably expressed in minutes.

Reduced dough stickiness may be determined as follows.

Dough stickiness is preferably determined on two separate batches of at least 8 dough pieces, with the Texture Analyser TAXT2i (Stable Micro Systems Ltd., Surrey, UK) equipped with a 5 kg load cell in the measure force in compression mode with a cylindrical probe (25 mm diameter). Using pre- and post-test speeds of 2.0 mm/s, while the test speed is 1.0 mm/s. Dough pieces are centered and compressed 50% and the probe is held for 10 s at maximum compression. A negative peak value indicates dough stickiness. A less negative peak value indicates reduced dough stickiness.

Increased flexibility may be determined as follows.

The baked product is laid on a flat surface. The baked product is rolled to a shape similar to a pipe, this way a rolled baked product is obtained. The flexiblity is improved if the rolled baked product remains its rolled up shape and does not roll open. This may be a particularly useful property if the baked product is a tortilla or a pancake.

The improved property may be determined by comparison of a dough and/or a baked product prepared with and without addition of the (isolated) polypeptide of the present invention in accordance with the methods of present invention which are described below in the Examples. Organoleptic qualities may be evaluated using procedures well established in the baking industry, and may include, for example, the use of a panel of trained taste-testers.

The term "increased strength of the dough" is defined herein as the property of a dough that has generally more elastic properties and/or requires more work input to mould and shape.

The term "increased elasticity of the dough" is defined herein as the property of a dough which has a higher tendency to regain its original shape after being subjected to a certain physical strain.

The term "increased stability of the dough" is defined herein as the property of a dough that is less susceptible to forming faults as a consequence of mechanical abuse thus better maintaining its shape and volume and is evaluated by the ratio of height:width of a cross section of a loaf after normal and/or extended proof.

The term "reduced stickiness of the dough" is defined herein as the property of a dough that has less tendency to adhere to surfaces, e.g., in the dough production machinery, and is either evaluated empirically by the skilled test baker or measured by the use of a texture analyser (e.g. a TAXT Plus) as known in the art.

The term "improved extensibility of the dough" is defined herein as the property of a dough that can be subjected to increased strain or stretching without rupture.

The term "improved machineability of the dough" is defined herein as the property of a dough that is generally less sticky and/or more firm and/or more elastic. Consequently there is less fouling of plant equipment and a reduced need for cleaning.

The term "increased volume of the baked product" is preferably measured as the volume of a given loaf of bread determined by an automated bread volume analyser (eg. BVM-3, TexVol Instruments AB, Viken, Sweden), using ultrasound or laser detection as known in the art. In case the volume is increased, the property is improved. Alternatively the height of the baked product after baking in the same size tin is an indication of the baked product volume. In case the height of the baked product has increased, the volume of the baked product has increased.

The term "reduced blistering of the baked product" is defined herein as a visually determined reduction of blistering on the crust of the baked bread.

The term "improved crumb structure of the baked product" is defined herein as the property of a baked product with finer cells and/or thinner cell walls in the crumb and/or more uniform/homogenous distribution of cells in the crumb and is usually evaluated visually by the baker or by digital image analysis as known in the art (eg. C-cell, Calibre Control International Ltd, Appleton, Warrington, UK).

The term "improved softness of the baked product" is the opposite of "hardness" and is defined herein as the property of a baked product that is more easily compressed and is evaluated either empirically by the skilled test baker or measured by the use of a texture analyzer (e.g. TAXT Plus) as known in the art. "hardness" may suitably be evaluated either empirically by the skilled test baker or measured by the use of a texture analyzer (e.g. TAXT Plus) as known in the art.

"Resilience" of a baked product may be measured by the use of a texture analyzer (e.g. TAXT Plus) as known in the art.

"Improved cohesiveness of the baked" product may be demonstrated by measurement via the use of a texture analyser (e.g. TAXT Plus) as known in the art. If a texture analyser is used, cohesiveness is how well the product withstands a second deformation relative to how it behaved under the first deformation. It is measured as the area of work during the second compression divided by the area of work during the first compression. Cohesiveness may be used to evaluate eating/chewing behavior of the baked product.

The term "improved flavor of the baked product" is evaluated by a trained test panel.

The term "improved anti-staling of the baked product" is defined herein as the properties of a baked product that have a reduced rate of deterioration of quality parameters, e.g. reduced hardness after storage and/or decreased loss of resilience after storage.

Anti-staling properties may be demonstrated by a reduced hardness after storage of the baked product. The enzyme composition according to the invention or the pre-mix according to the invention may result in reduced hardness, e.g. in a baked product that is more easily compressed. The hardness of the baked product may be evaluated either empirically by the skilled test baker or measured by the use of a texture analyzer (e.g. TAXT Plus) as known in the art. The hardness measured within 24 hours after baking is called initial hardness. The hardness measured 24 hours or more after baking is called hardness after storage, and is also a measure for determining shelf life. In case the initial hardness has reduced, it has improved. In case the hardness after storage has reduced, it has improved. Preferably hardness is measured as described in example 9 herein.

Resilience of the baked product is preferably measured by the use of a texture analyzer (e.g. TAXTPlus) as known in the art.

The resilience measured within 24 hours after baking is called initial resilience. The resilience measured 24 hours or more after baking is called resilience after storage, and is also a measure for determining shelf life. Freshly baked product typically gives crumb of high initial resilience but resilience is lost over shelf-life. Improved anti-staling properties may be demonstrated by a reduced loss of resilience over storage. Preferably resilience is measured as described in example 9 herein.

The term "improved crispiness" is defined herein as the property of a baked product to give a crispier sensation than a reference product as known in the art, as well as to maintain this crispier perception for a longer time than a reference product. This property can be quantified by measuring a force versus distance curve at a fixed speed in a compression experiment using e.g. a texture analyzer TA-XT Plus (Stable Micro Systems Ltd, Surrey, UK), and obtaining physical parameters from this compression curve, viz. (i) force of the first peak, (ii) distance of the first peak, (iii) the initial slope, (iv) the force of the highest peak, (v) the area under the graph and (vi) the amount of fracture events (force drops larger than a certain preset value). Indications of improved crispness are a higher force of the first peak, a shorter distance of the first peak, a higher initial slope, a higher force of the highest peak, higher area under the graph and a larger number of fracture events. A crispier product should score statistically significantly better on at least two of these parameters as compared to a reference product. In the art, "crispiness" is also referred to as crispness, crunchiness or crustiness, meaning a material with a crispy, crunchy or crusty fracture behaviour.

The present invention may provide a dough having at least one of the improved properties selected from the group consisting of increased strength, increased elasticity, increased stability, reduced stickiness, and/or improved extensibility of the dough.

The invention also may provide a baked product having increased loaf volume. The invention may provide as well a baked product having at least one improved property selected from the group consisting of increased volume, improved flavour, improved crumb structure, improved crumb softness, improved crispiness, reduced blistering and/or improved anti-staling.

The enzyme composition according to the invention or the pre-mix according to the invention may be used for retarding staling of a baked product such as bread and/or cake. Retarding of staling may be indicated by a reduced hardness, in particular a reduced hardness after storage compared to a baked product, including bread and cake, that is produced with the alpha-amylase variant in comparison with a parent polypeptide.

In an aspect according to the invention, there is provided a variant polypeptide having alpha-amylase activity, wherein the variant has an amino acid sequence which, when aligned with the alpha-amylase comprising the sequence set out in SEQ ID NO: 2, comprises at least one substitution of an amino acid residue corresponding to any of amino acids 1, 2, 3, 4, 5, 6, 7, 8, 9, 10, 11, 12, 13, 14, 15, 6, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200,
201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 251, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 351, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 451, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 551, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 651, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686,
said positions being defined with reference to SEQ ID NO: 2 and wherein the variant has one or more altered properties as compared with a reference polypeptide having alpha-amylase activity.

In an embodiment according to the invention there is provided a variant polypeptide having alpha-amylase activity, wherein the variant has an amino acid sequence which, when aligned with the alpha-amylase comprising the sequence set out in SEQ ID NO: 2, comprises at least one substitution of an amino acid residue corresponding to any of amino acids
4, 6, 13, 14, 15, 16, 20, 45, 47, 51, 54, 61, 68, 69, 70, 71, 72, 73, 74, 75, 77, 78, 80, 82, 87, 88, 94, 95, 100, 103, 104, 117, 124, 125, 126, 128, 130, 133, 134, 136, 143, 144, 146, 168, 174, 177, 178, 183, 186, 188, 189, 190, 194, 195, 199, 200, 201, 204, 207, 210, 214, 217, 219, 222, 225, 227, 233, 234, 235, 236, 240, 251, 252, 254, 258, 259, 260, 261, 262, 263, 264, 266, 267, 269, 271, 273, 281, 282, 283, 284, 286, 288, 299, 322, 323, 325, 327, 328, 331, 334, 350, 356, 358, 367, 370, 371, 374, 377, 378, 388, 391, 414, 421, 422, 445, 450, 467, 488, 505, 536, 548, 554, 583, 588, 603, 637, 648, 651, 652, 660, 676, 677, said positions being defined with reference to SEQ ID NO: 2 and wherein the variant has one or more altered properties as compared with a reference polypeptide having alpha-amylase activity.

Table 1 sets out positions that may influence specific properties of the variant alpha-amylases of the invention.

Accordingly, in an embodiment of the alpha-amylase variant according to the invention comprises an amino acid sequence which, when aligned with the sequence set out in SEQ ID NO: 2, comprises at least one substitution of an amino acid residue corresponding to any of amino acids 1, 2, 3, 4, 5, 6, 7, 8, 9, 10, 11, 12, 13, 14, 15, 6, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 251, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 351, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 451, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 551, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 651, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, said positions being defined with reference to SEQ ID NO: 2 and wherein the variant demonstrates any one of
  a) increased (thermo)stability; or
  b) increased specific activity; or
  c) increased sucrose tolerance; or
  d) increased stability/activity at different pH range; or
  e) change in product spectrum (defined as ratio of one product over another); or
  f) increased activity on raw starch; or
  g) altered temperature optimum; or
  h) alter substrate specificity; or
  i) increased productivity in the production of the alpha-amylase variant;
as compared with a reference polypeptide having alpha-amylase activity.

In an embodiment according to the invention there is provided a variant polypeptide having alpha-amylase activity, wherein the variant has an amino acid sequence which, when aligned with the alpha-amylase comprising the sequence set out in SEQ ID NO: 2, comprises at least one substitution of an amino acid residue corresponding to any of amino acids 4, 6, 13, 14, 15, 16, 20, 45, 47, 51, 54, 61, 68, 69, 70, 71, 72, 73, 74, 75, 77, 78, 80, 82, 87, 88, 94, 95, 100, 103, 104, 117, 124, 125, 126, 128, 130, 133, 134, 136, 143, 144, 146, 168, 174, 177, 178, 183, 186, 188, 189, 190, 194, 195, 199, 200, 201, 204, 207, 210, 214, 217, 219, 222, 225, 227, 233, 234, 235, 236, 240, 251, 252, 254, 258, 259, 260, 261, 262, 263, 264, 266, 267, 269, 271, 273, 281, 282, 283, 284, 286, 288, 299, 322, 323, 325, 327, 328, 331, 334, 350, 356, 358, 367, 370, 371, 374, 377, 378, 388, 391, 414, 421, 422, 445, 450, 467, 488, 505, 536, 548, 554, 583, 588, 603, 637, 648, 651, 652, 660, 676, 677, said positions being defined with reference to SEQ ID NO: 2 and wherein the variant demonstrates any one of
  a) increased (thermo)stability; or
  b) increased specific activity; or
  c) increased sucrose tolerance; or
  d) increased stability/activity at different pH range; or
  e) change in product spectrum (defined as ratio of one product over another); or
  f) increased activity on raw starch; or
  g) altered temperature optimum; or
  h) alter substrate specificity; or
  i) increased productivity in the production of the alpha-amylase variant;
as compared with a reference polypeptide having alpha-amylase activity.

In an aspect the alpha-amylase variant according to the invention, is an alpha-amylase variant having at least 80% identity, in an aspect at least 85% identity, in an aspect at least 90% identity, in an aspect at least 95% identity, in an aspect at least 98% identity, in an aspect at least 99% identity, in an aspect at least 99.5% identity, with the polypeptide sequence as set out in SEQ ID NO: 2, wherein at least one amino acid residue of the variant is substituted at a position selected from the group consisting of 4, 6, 13, 14, 15, 16, 20, 45, 47, 51, 54, 61, 68, 69, 70, 71, 72, 73, 74, 75, 77, 78, 80, 82, 87, 88, 94, 95, 100, 103, 104, 117, 124, 125, 126, 128, 130, 133, 134, 136, 143, 144, 146, 168, 174, 177, 178, 183, 186, 188, 189, 190, 194, 195, 199, 200, 201, 204, 207, 210, 214, 217, 219, 222, 225, 227, 233, 234, 235, 236, 240, 251, 252, 254, 258, 259, 260, 261, 262, 263, 264, 266, 267, 269, 271, 273, 281, 282, 283, 284, 286, 288, 299, 322, 323, 325, 327, 328, 331, 334, 350, 356, 358, 367, 370, 371, 374, 377, 378, 388, 391, 414, 421, 422, 445, 450, 467, 488, 505, 536, 548, 554, 583, 588, 603, 637, 648, 651, 652, 660, 676, 677, said positions being defined with reference to SEQ ID NO: 2;

and wherein the variant has a specific activity which is higher at at least one pH, preferably a pH between 4 and 8, than that of the polypeptide as set out in SEQ ID NO: 2 measured at the same pH and/or wherein the variant has a pH optimum which is higher than that of the polypeptide as set out in SEQ ID NO: 2.

In one embodiment an alpha-amylase variant according to the invention may have a pH optimum which is altered compared to the parent polypeptide In one embodiment an alpha-amylase variant according to the invention may have a pH optimum which is higher than that of the parent polypeptide having alpha-amylase activity or lower than such parent polypeptide. In an aspect the pH optimum of the alpha-amylase variant protein is higher than that of the parent polypeptide. Preferably the parent polypeptide is that according to SEQ ID NO: 2. For example, the wild-type alpha-amylase from *Alicyclobacillus pohliae* (as disclosed in SEQ ID NO: 2) has a pH optimum of from pH 4 to pH 5. In an aspect an alpha-amylase variant of the invention may be more alkaliphilic than such a wild-type enzyme, i.e. may, for example, have a pH optimum of from pH 5 to pH 8, preferably from pH 6 to pH 7. Optionally a variant protein of the invention may be more acidophilic than the wild type alpha-amylase.

In an aspect an alpha-amylase variant according to the invention may have a pH, which is higher than the pH optimum and at which 50% of the alpha-amylase activity is still present, (hereafter indicated as alkaline pH), which is higher than that of the parent alpha-amylase. When the parent polypeptide having alpha-amylase activity is that according to SEQ ID NO: 2 the variant protein may have an alkaline pH at which 50% of the activity is observed which is at least 6.9, preferably, at least 7.0, at least 7.5, preferably at least 8.

A variant which exhibits a property which is improved in relation to the parent polypeptide having alpha-amylase activity is one which demonstrates a measurable reduction or increase in the relevant property, typically such that the variant is more suited to use as set out below, for example in a method for the production of a foodstuff.

In an aspect an alpha-amylase variant according to the invention may have a specific activity which is higher than that of the parent polypeptide measured at the same pH. With specific activity of a variant protein it is herewith intended the alpha amylase activity of the alpha-amylase variant measured in units/mg of pure protein. Preferably the specific activity of the alpha-amylase variant according to the invention is higher at at least one pH, preferably a pH between 4 and 8, than that of the parent polypeptide measured at the same pH.

In an embodiment the alpa-amylase variant according to the invention has a Cys amino acid at any one of both of 4 and 505, 77 and 88, 78 and 134, 82 and 144, 207 and 676, 207 and 676, 207 and 677, 240 and 583, 488 and 467, 536 and 548, 583 and 236, 588 and 651 or 677 and 204, said positions being defined with reference to SEQ ID NO: 2 and wherein the variant has one or more altered properties as compared with a reference polypeptide having alpha-amylase activity.

In an embodiment the alpha-amylase variant according to the invention the reference polypeptide is the alpha-amylase of SEQ ID NO: 2

In an embodiment the alpha-amylase variant according to the invention comprises an amino acid sequence which, when aligned with the sequence set out in SEQ ID NO: 2, comprises at least one substitution of an amino acid residue corresponding to any of amino acids 4, 6, 13, 14, 15, 16, 20, 45, 47, 51, 54, 61, 68, 69, 70, 71, 72, 73, 74, 75, 77, 78, 80, 82, 87, 88, 94, 95, 100, 103, 104, 117, 124, 125, 126, 128, 130, 133, 134, 136, 143, 144, 146, 168, 174, 177, 178, 183, 186, 188, 189, 190, 194, 195, 199, 200, 201, 204, 207, 210, 214, 217, 219, 222, 225, 227, 233, 234, 235, 236, 240, 251, 252, 254, 258, 259, 260, 261, 262, 263, 264, 266, 267, 269, 271, 273, 281, 282, 283, 284, 286, 288, 299, 322, 323, 325, 327, 328, 331, 334, 350, 356, 358, 367, 370, 371, 374, 377, 378, 388, 391, 414, 421, 422, 445, 450, 467, 488, 505, 536, 548, 554, 583, 588, 603, 637, 648, 651, 652, 660, 676, 677, said positions being defined with reference to SEQ ID NO: 2 and wherein the variant demonstrates any one of a) increased (thermo)stability; or
b) increased specific activity; or
c) increased sucrose tolerance; or
d) increased stability/activity at different pH range; or
e) change in product spectrum (defined as ratio of one product over another); or
f) increased activity on raw starch; or
g) altered temperature optimum; or
h) alter substrate specificity; or
i) increased productivity in the production of the alpha-amylase variant;

as compared with a reference polypeptide having alpha-amylase activity.

A preferred reference polypeptide suitable for use in the invention is the polypeptide having the sequence set out in SEQ ID NO: 2 or having at least 80% homology with SEQ ID NO: 2, for example at least 85% homology with SEQ ID NO: 2, such a least 85% homology with SEQ ID NO: 2, such as at least 90% homology with SEQ ID NO: 2, for example at least 95%, at least 98%, at least 99% or at least 99.5% homology with SEQ ID NO: 2.

The amino acid residues in a variant alpha-amylase of the invention that may be substituted with comparison with the sequence set out in SEQ ID NO: 2 are those which correspond to positions 1, 2, 3, 4, 5, 6, 7, 8, 9, 10, 11, 12, 13, 14, 15, 6, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 251, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 351, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 451, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 551, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 651, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, as defined in relation to the sequence of SEQ ID NO: 2.

In an embodiment the amino acid residues in a variant alpha-amylase of the invention that may be substituted with comparison with the sequence set out in SEQ ID NO: 2 are those which correspond to positions 4, 6, 13, 14, 15, 16, 20, 45, 47, 51, 54, 61, 68, 69, 70, 71, 72, 73, 74, 75, 77, 78, 80, 82, 87, 88, 94, 95, 100, 103, 104, 117, 124, 125, 126, 128, 130, 133, 134, 136, 143, 144, 146, 168, 174, 177, 178, 183, 186, 188, 189, 190, 194, 195, 199, 200, 201, 204, 207, 210, 214, 217, 219, 222, 225, 227, 233, 234, 235, 236, 240, 251, 252, 254, 258, 259, 260, 261, 262, 263, 264, 266, 267, 269, 271, 273, 281, 282, 283, 284, 286, 288, 299, 322, 323, 325, 327, 328, 331, 334, 350, 356, 358, 367, 370, 371, 374, 377, 378, 388, 391, 414, 421, 422, 445, 450, 467, 488, 505, 536, 548, 554, 583, 588, 603, 637, 648, 651, 652, 660, 676, 677, as defined in relation to the sequence of SEQ ID NO: 2.

A variant alpha-amylase of the invention may comprises a substitution at one or more of the said positions, for example at two, three, four, at least 5, at least 10, at least 15, at least 20, at least 25, at least 30, at least 35, at least 40, at least 45 or at least 50 or at all of the said positions.

A variant alpha-amylase of the invention may comprise one or more substitutions as defined above. A "substitution" in this context indicates that a position in the variant which corresponds to one of the positions set out above in SEQ ID NO: 2 comprises an amino acid residue which does not appear at that position in the reference polypeptide (the reference polypeptide may be SEQ ID NO: 2).

Preferred substitutions are set out in the following Table 1 and Table 2 (with the positions being defined in relation to the sequence set out in SEQ ID NO: 2).

A variant of the invention may be generated using any combination of substitutions set out in Table 1 and/or Table 2.

TABLE 1

Preferred substitutions defined in relation to SEQ ID NO: 2
Amino acids are depicted according to the single letter annotation

| # | Substitution*) |
|---|---|
| 01 | V6F |
| 2 | I14V |
| 3 | I15F |
| 4 | I15V |
| 5 | I16T |
| 6 | M45L |
| 7 | W47F |
| 8 | L51W |
| 9 | V54L |
| 10 | V54I |
| 11 | L61F |
| 12 | I69L |
| 13 | L71I |
| 14 | P73Q |
| 15 | V74P |
| 16 | L75V |
| 17 | L75F |
| 18 | L78I |
| 19 | L78V |
| 20 | T80A |
| 21 | T87V |
| 22 | G88A |
| 23 | G88S |
| 24 | T94A |
| 25 | T94P |
| 26 | R95K |
| 27 | I100T |
| 28 | H103Y |
| 29 | F104Y |
| 30 | V124I |
| 31 | I125V |
| 32 | V126I |
| 33 | V129A |
| 34 | V129T |
| 35 | P130V |
| 36 | S133T |
| 37 | T134S |
| 38 | F136A |
| 39 | F143Y |
| 40 | G146N |
| 41 | F168Y |
| 42 | I174L |
| 43 | I174V |
| 44 | W177F |
| 45 | D178N |
| 46 | A183S |
| 47 | K186R |
| 48 | K186Q |
| 49 | F188I |
| 50 | T189Y |
| 51 | D190N |
| 52 | F194Y |
| 53 | S195T |
| 54 | S195A |
| 55 | S195N |
| 56 | L199F |
| 57 | S200N |
| 58 | Q201H |
| 59 | L210F |
| 60 | A214I |
| 61 | L217Y |
| 62 | L217W |
| 63 | A219D |
| 64 | A222V |
| 65 | A222I |
| 66 | I227V |

TABLE 1-continued

Preferred substitutions defined in relation to SEQ ID NO: 2
Amino acids are depicted according to the single letter annotation

| # | Substitution*) |
|---|---|
| 67 | F233Y |
| 68 | F233M |
| 69 | N234P |
| 70 | S235L |
| 71 | I251V |
| 72 | V254F |
| 73 | Y258F |
| 74 | G259L |
| 75 | D260G |
| 76 | P262S |
| 77 | G263A |
| 78 | A264S |
| 79 | N266S |
| 80 | H267N |
| 81 | E269D |
| 82 | V271T |
| 83 | V271I |
| 84 | Y273F |
| 85 | V279M |
| 86 | V281L |
| 87 | L286F |
| 88 | T288S |
| 89 | T288N |
| 90 | T288Q |
| 91 | T323N |
| 92 | I325F |
| 93 | N327S |
| 94 | H328Q |
| 95 | S331D |
| 96 | I350T |
| 97 | T356V |
| 98 | S358A |
| 99 | M367L |
| 100 | G370N |
| 101 | N371G |
| 102 | Y374D |
| 103 | G377A |
| 104 | M378K |
| 105 | W414Y |
| 106 | I421V |
| 107 | Y422F |
| 108 | I445V |
| 109 | T603S |
| 110 | T603V |
| 111 | Y637F |
| 112 | Y637I |
| 113 | Q648E |
| 114 | T450S |
| 115 | F652I |
| 116 | I660V |
| 117 | Q13E |
| 118 | Y20L |
| 119 | Y20V |
| 120 | T68A |
| 121 | T68S |
| 122 | T68G |
| 123 | W70Y |
| 124 | S72T |
| 125 | A117V |
| 126 | A117C |
| 127 | F128Y |
| 128 | F128I |
| 129 | F128L |
| 130 | L225I |
| 131 | L225F |
| 132 | L225W |
| 133 | F252Y |
| 134 | F252L |
| 135 | L282W |
| 136 | L282F |
| 137 | L282I |
| 138 | L282M |
| 139 | L282T |
| 140 | Q299S |
| 141 | L334K |
| 142 | L334Y |
| 143 | L334Q |
| 144 | L334H |
| 145 | L282M |
| 146 | D283N |
| 147 | D283S |
| 148 | F284Y |
| 149 | F284I |
| 150 | F284M |
| 151 | F284W |
| 152 | F284L |
| 153 | I322V |
| 154 | I322F |
| 155 | I322P |
| 156 | A388L |
| 157 | A388S |
| 158 | E391V |
| 159 | D261G |
| 160 | A4C-A505C |
| 161 | N77C-G88C |
| 162 | L78C-T134C |
| 163 | A82C-A144C |
| 164 | A207C-A676C |
| 165 | A207C-T677C |
| 166 | S240C-S583C |
| 167 | S488C-G467C |
| 168 | A536C-V548C |
| 169 | S583C-G236C |
| 170 | V588C-F651C |
| 171 | T677C-G204C |
| 172 | S133L |
| 173 | A554G |

*)meaning of -: A4C-A505C means 2 substitutions: both the amino acid at position 4 and the amino acid at position 505 are changed to a C, i.e. A4 is changed to 4C and A505 changed to 505C, and as a result the variant has a Cys amino acid at both of 4 and 505; N77C-G88C means that both N77 and G88 are changed to a C amino acid, as a result the variant has a Cys amino acid at both of 77 and 88, etc.
In other words A4C-A505C means both the amino acid at position 4 and the amino acid at position 505 are changed to a C, i.e. Alanine at position 4 is changed to Cysteine at position 4 and Alanine at position 505 is changed to Cysteine at position 505, etc.

TABLE 2 possible substitutions, position in reference to SEQ ID NO: 2
Amino acids are depicted according to the single letter annotation

| position | Change to amino acid (multiple options from which a selection may be made are separated by /) |
|---|---|
| 13 | S/T/A/V/L/I/F/M |
| 15 | T/S/V/L/D |
| 17 | Q/E |
| 18 | K |
| 26 | S/T/A/V/L/I |
| 30 | D/M/L/A/V/I/E/Q |
| 32 | D/E/N/Q |
| 35 | Q |
| 40 | R |
| 44 | R/S/T/Q/N |
| 45 | K |
| 51 | W |
| 73 | Q |
| 74 | P |
| 75 | F/Y |
| 76 | E |
| 77 | S/T/A/V/L/I |
| 78 | I |
| 79 | E/Y |
| 86 | S/T/A/V/L/I/Q/G/K |
| 87 | N/Q/S |
| 88 | A/S/T |
| 89 | W/F/H |
| 90 | W/F/Y/R/K/N/Q/M |
| 91 | T/S/V/N |

TABLE 2-continued possible substitutions, position in reference to SEQ ID NO: 2
Amino acids are depicted according to the single letter annotation

| position | Change to amino acid (multiple options from which a selection may be made are separated by /) |
|---|---|
| 93 | S/G/V/T/M/E/Y/F |
| 94 | V/I/L |
| 95 | L/A/N/I/E/Q |
| 99 | T/S/V/L |
| 100 | T/S/D/N/E/Q |
| 103 | Y/V/I/L/F/Y/N/Q/D/E |
| 114 | V/I/L |
| 119 | T/S |
| 120

TABLE 2-continued possible substitutions, position in reference to SEQ ID NO: 2
Amino acids are depicted according to the single letter annotation

| position | Change to amino acid (multiple options from which a selection may be made are separatedb y /) |
|---|---|
| 628 | M/I/F/Y/W |
| 629 | N/D/E/Q |
| 636 | Y |
| 642 | Q |
| 645 | T |
| 664 | D/S/T/A/V/L/I |
| 670 | V/I/L/M/F/Y/W |
| 681 | D/N/E/Q/S |

In an embodiment of the variant polypeptide according to the invention having alpha-amylase activity, the variant has an amino acid sequence which, when aligned with the alpha-amylase comprising the sequence set out in SEQ ID NO: 2, comprises a substitution of the amino acid residue 133, said position being defined with reference to SEQ ID NO: 2.

In an embodiment of the variant polypeptide according to the invention having alpha-amylase activity, the variant has an amino acid sequence which, when aligned with the alpha-amylase comprising the sequence set out in SEQ ID NO: 2, comprises a substitution of the amino acid residue 133, said position being defined with reference to SEQ ID NO: 2, wherein the substitution is S133L.

In an embodiment of the variant polypeptide according to the invention having alpha-amylase activity, the variant has an amino acid sequence which, when aligned with the alpha-amylase comprising the sequence set out in SEQ ID NO: 2, comprises a substitution of the amino acid residue 554, said position being defined with reference to SEQ ID NO: 2.

In an embodiment of the variant polypeptide according to the invention having alpha-amylase activity, the variant has an amino acid sequence which, when aligned with the alpha-amylase comprising the sequence set out in SEQ ID NO: 2, comprises a substitution of the amino acid residue 554, said position being defined with reference to SEQ ID NO: 2, wherein the substitution is A554G.

A variant alpha-amylase of the invention may also comprise additional modifications in comparison to the parent at positions other than those specified above, for example, one or more additional substitutions, additions or deletions. A variant of the invention may comprise a combination of different types of modification of this sort. A variant may comprise one, two, three, four, least 5, at least 10, at least 15, at least 20, at least 25, at least 30 or more such modifications (which may all be of the same type or may be different types of modification). Typically, the additional modifications may be substitutions.

A variant according to the invention may have at least 80% homology with the reference alpha-amylase polypeptide, such as the alpha-amylase of SEQ ID NO: 2, for example at least 85% homology with the parent polypeptide, such as 90% homology with the parent polypeptide, at least 95% homology with the parent polypeptide, at least 98% homology with the parent polypeptide, at least 99% homology with the parent polypeptide or at least 99.5% homology with the parent polypeptide.

A variant of the invention will typically retain alpha-amylase activity. That is to say, a variant of the invention will typically be capable of alpha amylase activity. Alpha-amylase activity can suitably be determined using the Cer-alpha® procedure, which is recommended by the American Association of Cereal Chemists (AACC). All variants listed in Table 1 herein showed alpha-amylase activity in the CERALPHA assay. The reference polypeptide as set out in SEQ ID NO: 2 showed alpha-amylase activity in the CER-ALPHA assay.

A variant of the invention will typically be a starch degrading enzyme.

In an embodiment of the variant polypeptide according to the invention, the variant polypeptide has at least 70% identity with the polypeptide sequence as set out in SEQ ID NO: 2, and, when aligned with the sequence as set out in SEQ ID NO: 2, comprises at least one substitution of an amino acid residue corresponding to any of amino acids 13, 15, 16, 20, 45, 61, 68, 70, 72, 75, 77, 78, 88, 94, 124, 126, 128, 129, 129, 133, 134, 136, 168, 174, 177, 178, 186, 188, 194, 195, 199, 200, 210, 219, 222, 225, 234, 254, 261, 264, 267, 269, 271, 281, 282, 283, 284, 288, 323, 325, 327, 331, 334, 358, 370, 371, 377, 388, 421, 450, 652, said positions being defined with reference to SEQ ID NO: 2;

and wherein the variant demonstrates any one of
a) increased thermostability;
b) increased sucrose tolerance;
c) increased Activity at pH4:Activity at pH 5 ratio; or
d) increased thermostability in the presence of sucrose
as compared with a reference polypeptide as set out in SEQ ID NO: 2.

In an aspect of the alpha-amylase polypeptide variant according to the invention, said variant polypeptide, when aligned with the sequence as set out in SEQ ID NO: 2, comprises at least one substitution of an amino acid residue corresponding to any of amino acids 13, 15, 16, 20, 45, 61, 68, 70, 72, 75, 77, 78, 88, 94, 124, 126, 128, 129, 129, 133, 134, 136, 168, 174, 177, 178, 186, 188, 194, 195, 199, 200, 210, 219, 222, 225, 234, 254, 261, 264, 267, 269, 271, 281, 282, 283, 284, 288, 323, 325, 327, 331, 334, 358, 370, 371, 377, 388, 421, 450, 652, said positions being defined with reference to SEQ ID NO: 2; and the variant demonstrates any one of
a) increased thermostability;
b) increased sucrose tolerance;
c) increased Activity at pH4:Activity at pH 5 ratio; or
d) increased thermostability in the presence of sucrose
as compared with a polypeptide as set out in SEQ ID NO: 2;

and the variant has at least 75%, in an aspect at least 80%, in an aspect at least 85%, in an aspect at least 90%, in an aspect at least 95%, in an aspect at least 96%, in an aspect at least 97% in an aspect at least 98%, in an aspect at least 99%, in an aspect at least 99.5% identity with the polypeptide sequence as set out in SEQ ID NO: 2.

In an embodiment of the variant polypeptide according to the invention, the variant polypeptide has at least 70% identity with the polypeptide sequence as set out in SEQ ID NO: 2, and, when aligned with the sequence as set out in SEQ ID NO: 2, comprises at least one substitution of an amino acid residue corresponding to any of amino acids 45, 68, 70, 72, 88, 94, 133, 134, 168, 186, 188, 200, 222, 254, 261, 264, 281, 282, said positions being defined with reference to SEQ ID NO: 2;

and wherein the variant demonstrates any one of
a) increased thermostability;
b) increased sucrose tolerance;
c) increased Activity at pH4:Activity at pH 5 ratio; or
d) increased thermostability in the presence of sucrose
as compared with a reference polypeptide as set out in SEQ ID NO: 2.

In an embodiment of the variant polypeptide according to the invention, the variant polypeptide has at least 70% identity with the polypeptide sequence as set out in SEQ ID NO: 2,
and, when aligned with the sequence as set out in SEQ ID NO: 2, comprises at least one substitution of an amino acid residue corresponding to any of amino acids
68, 72, 88, 133, 168, 188, 200, 222, 254, 261, 281, 282,
said positions being defined with reference to SEQ ID NO: 2;
and wherein the variant demonstrates any one of
a) increased thermostability;
b) increased sucrose tolerance;
c) increased Activity at pH4:Activity at pH 5 ratio; or
d) increased thermostability in the presence of sucrose
as compared with a reference polypeptide as set out in SEQ ID NO: 2.

In an embodiment of the variant polypeptide according to the invention, the variant polypeptide has at least 70% identity with the polypeptide sequence as set out in SEQ ID NO: 2,
and, when aligned with the sequence as set out in SEQ ID NO: 2, comprises at least one substitution of an amino acid residue corresponding to any of amino acids
68, 282,
said positions being defined with reference to SEQ ID NO: 2;
and wherein the variant demonstrates any one of
a) increased thermostability;
b) increased sucrose tolerance;
c) increased Activity at pH4:Activity at pH 5 ratio; or
d) increased thermostability in the presence of sucrose
as compared with a reference polypeptide as set out in SEQ ID NO: 2.

In an embodiment of the variant polypeptide according to the invention, the variant polypeptide has at least 70% identity with the polypeptide sequence as set out in SEQ ID NO: 2,
and, when aligned with the sequence as set out in SEQ ID NO: 2, comprises at least one substitution of an amino acid residue corresponding to any of amino acids
13, 15, 16, 20, 45, 61, 68, 70, 72, 75, 77, 78, 88, 94, 124, 126, 128, 129, 129, 133, 134, 136, 168, 174, 177, 178, 186, 188, 194, 195, 199, 200, 210, 219, 222, 225, 234, 254, 261, 264, 267, 269, 271, 281, 282, 283, 284, 288, 323, 325, 327, 331, 334, 358, 370, 371, 377, 388, 421, 450, 652,
said positions being defined with reference to SEQ ID NO: 2;
and wherein the variant demonstrates any one of
e) increased thermostability;
f) increased sucrose tolerance;
g) increased Activity at pH4:Activity at pH 5 ratio; or
h) increased thermostability in the presence of sucrose
as compared with a reference polypeptide as set out in SEQ ID NO: 2, while the specific activity of the variant has reduced by at most 10% as compared with the reference polypeptide.

In an aspect of this embodiment the specific activity of the variant has reduced by at most 20%, in an aspect by at most 30%, in an aspect by at most 40%, in an aspect by at most 50% as compared to the reference polypeptide. In a further aspect of this embodiment the specific activity of the variant is at least the same or has increased compared to the reference polypeptide. In a further aspect of this embodiment the specific activity is determined using maltotriose as a substrate.

Preferably, a variant of the invention will typically exhibit improved properties in comparison with the reference alpha-amylase polypeptide from which it is derived. Such an improved property will typically be one which is relevant if the variant were to be used as set out herein, for example in a method for preparing a baked product.

A variant which exhibits a property which is improved in relation to the reference alpha-amylase is one which demonstrates a measurable reduction or increase in the relevant property, typically such that the variant is more suited to use as set out herein, for example in a method for the production of a baked product.

The property may thus be decreased by at least 10%, at least 20%, at least 30%, at least 40% at least 50%, at least 60%, at least 70%, at least 80%, at least 90%, at least 95% or at least 99%. Alternatively, the property may be increased by at least 10%, at least 25%, at least 50%, at least 100%, at least, 200%, at least 500% or at least 1000%. The percentage decrease or increase in this context represents the percentage decrease or increase in comparison to the reference alpha-amylase polypeptide. It is well known to the skilled person how such percentage changes may be measured—it is a comparison of the activity of the reference alpha-amylase and the variant alpha-amylase.

The variants described herein are collectively comprised in the terms "a polypeptide according to the invention" or "a variant according to the invention".

The terms "peptide" and "oligopeptide" are considered synonymous (as is commonly recognized) and each term can be used interchangeably as the context requires to indicate a chain of at least two amino acids coupled by peptidyl linkages. The word "polypeptide" is used herein for chains containing more than about seven amino acid residues. All oligopeptide and polypeptide formulas or sequences herein are written from left to right and in the direction from amino terminus to carboxy terminus. The one-letter code of amino acids used herein is commonly known in the art and can be found in Sambrook, et al. (Molecular Cloning: A Laboratory Manual, 2nd, ed. Cold Spring Harbor Laboratory, Cold Spring Harbor Laboratory Press, Cold Spring Harbor, N. Y., 1989).

A polypeptide of the invention may be in isolated form, such as substantially isolated form. By "isolated" polypeptide or protein is intended a polypeptide or protein removed from its native environment. For example, recombinantly produced polypeptides and proteins expressed in host cells are considered isolated for the purpose of the invention as are recombinant polypeptides which have been substantially purified by any suitable technique. A polypeptide variant according to the invention can be recovered and purified from recombinant cell cultures by methods known in the art.

Polypeptides of the present invention include products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

The invention also features biologically active fragments of the polypeptide variants according to the invention. Such fragments are considered to be encompassed within the term "a variant of the invention".

Biologically active fragments of a polypeptide variant of the invention include polypeptides comprising amino acid sequences sufficiently identical to or derived from the amino acid sequence of a variant protein of the invention which include fewer amino acids than the full length protein but which exhibit at least one biological activity of the corresponding full-length protein. Typically, biologically active fragments comprise a domain or motif with at least one activity of a variant protein of the invention. A biologically active fragment of a protein of the invention can be a polypeptide which is, for example, 10, 25, 50, 100 or more amino acids in length. Moreover, other biologically active portions, in which other regions of the protein are deleted, can be prepared by recombinant techniques and evaluated for one or more of the biological activities of the native form of a polypeptide of the invention.

Typically, a protein fragment of the invention will comprise one or more of the substitutions defined herein.

The invention also features nucleic acid fragments which encode the above biologically active fragments (which biologically active fragments are themselves variants of the invention).

As set out above, the present invention provides polynucleotides encoding the variant polypeptides of the invention. The invention also relates to an isolated polynucleotide encoding at least one functional domain of a polypeptide variant of the invention. Typically, such a domain will comprise one or more of the substitutions described herein.

In one embodiment of the invention, the nucleic acid sequence according to the invention encodes a polypeptide, wherein the polypeptide is a variant comprising an amino acid sequence that has one or more truncation(s), and/or at least one substitution, deletion and/or insertion of an amino acid as compared to the parent alpha-amylase. Such a polypeptide will, however, typically comprise one or more of the substitutions described herein.

As used herein, the terms "gene" and "recombinant gene" refer to nucleic acid molecules which include an open reading frame encoding a variant as described herein. A gene may include coding sequences, non-coding sequences, introns and regulatory sequences. That is to say, a "gene", as used herein, may refer to an isolated nucleic acid molecule as defined herein. Accordingly, the term "gene", in the context of the present application, does not refer only to naturally-occurring sequences.

A nucleic acid molecule of the present invention can be generated using standard molecular biology techniques well known to those skilled in the art taken in combination with the sequence information provided herein.

A nucleic acid molecule of the present invention can be adapted according to the method described in patent application U.S. Ser. No. 09/028,6280.

For example, using standard synthetic techniques, the required nucleic acid molecule may be synthesized de novo. Such a synthetic process will typically be an automated process.

Alternatively, a nucleic acid molecule of the invention may be generated by use of site-directed mutagenesis of an existing nucleic acid molecule, for example a wild-type nucleic acid molecule. Site-directed mutagenesis may be carried out using a number of techniques well known to those skilled in the art.

In one such method, mentioned here merely by way of example, PCR is carried out on a plasmid template using oligonucleotide "primers" encoding the desired substitution. As the primers are the ends of newly-synthesized strands, should there be a mis-match during the first cycle in binding the template DNA strand, after that first round, the primer-based strand (containing the mutation) would be at equal concentration to the original template. After successive cycles, it would exponentially grow, and after 25, would outnumber the original, unmutated strand in the region of 8 million: 1, resulting in a nearly homogeneous solution of mutated amplified fragments. The template DNA may then be eliminated by enzymatic digestion with, for example using a restriction enzyme which cleaves only methylated DNA, such as Dpn1. The template, which is derived from an alkaline lysis plasmid preparation and therefore is methylated, is destroyed in this step, but the mutated plasmid is preserved because it was generated in vitro and is unmethylated as a result.

In such a method more than one mutation (encoding a substitution as described herein) may be introduced into a nucleic acid molecule in a single PCR reaction, for example by using one or more oligonucleotides, each comprising one or more mis-matches. Alternatively, more than one mutation may be introduced into a nucleic acid molecule by carrying out more than one PCR reaction, each reaction introducing one or more mutations, so that altered nucleic acids are introduced into the nucleic acid in a sequential, iterative fashion.

A nucleic acid of the invention can be generated using cDNA, mRNA or alternatively, genomic DNA, as a template and appropriate mis-matched oligonucleotide primers according to the site-directed mutagenesis technique described above. A nucleic acid molecule derived in this way can be cloned into an appropriate vector and characterized by DNA sequence analysis.

A nucleic acid sequence of the invention may comprise one or more deletions, i.e. gaps, in comparison to the parent alpha-amylase. Such deletions/gaps may also be generated using site-directed mutagenesis using appropriate oligonucleotides. Techniques for generating such deletions are well known to those skilled in the art.

Furthermore, oligonucleotides corresponding to or hybridizable to nucleotide sequences according to the invention can be prepared by standard synthetic techniques, e.g. using an automated DNA synthesizer.

Also, complementary nucleic acid molecules are included in the present invention. A nucleic acid molecule which is complementary to another nucleotide sequence is one which is sufficiently complementary to the other nucleotide sequence such that it can hybridize to the other nucleotide sequence thereby forming a stable duplex.

One aspect of the invention pertains to isolated nucleic acid molecules that encode a variant of the invention, or a biologically active fragment or domain thereof, as well as nucleic acid molecules sufficient for use as hybridization probes to identify nucleic acid molecules encoding a polypeptide of the invention and fragments of such nucleic acid molecules suitable for use as PCR primers for the amplification or mutation of nucleic acid molecules, such as for the preparation of nucleic acid molecules of the invention.

An "isolated polynucleotide" or "isolated nucleic acid" is a DNA or RNA that is not immediately contiguous with both of the coding sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promotor) sequences that are immediately contiguous to the coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide that is substantially free of cellular material, viral material, or culture medium (when produced by recombinant DNA techniques), or chemical precursors or other chemicals (when chemically synthesized). Moreover, an "isolated nucleic acid fragment" is a nucleic acid fragment that is not naturally occurring as a fragment and would not be found in the natural state.

As used herein, the terms "polynucleotide" or "nucleic acid molecule" are intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. The nucleic acid may be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

Another embodiment of the invention provides an isolated nucleic acid molecule which is antisense to a nucleic acid molecule of the invention.

The terms "homology" or "percent identity" are used interchangeably herein. For the purpose of this invention, it is defined here that in order to determine the percent identity of two amino acid sequences or two nucleic acid sequences, the sequences are aligned for optimal comparison purposes (e.g., gaps can be introduced in the sequence of a first amino acid or nucleic acid for optimal alignment with a second amino or nucleic acid sequence). The amino acid or nucleotide residues at corresponding amino acid or nucleotide positions are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are the same length.

A sequence comparison may be carried out over the entire lengths of the two sequences being compared or over fragment of the two sequences. Typically, the comparison will be carried out over the full length of the two sequences being compared. However, sequence identity may be carried out over a region of, for example, twenty, fifty, one hundred or more contiguous amino acid residues.

The skilled person will be aware of the fact that several different computer programs are available to determine the homology between two sequences. For instance, a comparison of sequences and determination of percent identity between two sequences can be accomplished using a mathematical algorithm. In a preferred embodiment, the percent identity between two amino acid or nucleic acid sequences is determined using the Needleman and Wunsch (J. Mol. Biol. (48): 444-453 (1970)) algorithm which has been incorporated into the GAP program in the Accelrys GCG software package (available at http://www.accelrys.com/products/gcg/), using either a Blosum 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

The protein sequences or nucleic acid sequences of the present invention can further be used as a "query sequence" to perform a search against public databases to, for example, identify other family members or related sequences. Such searches can be performed using the BLASTN and BLASTP programs (version 2.0) of Altschul, et al. (1990) J. Mol. Biol. 215:403-10. BLAST protein searches can be performed with the BLASTP program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., BLASTP and BLASTN) can be used. See the homepage of the National Center for Biotechnology Information at http://www.ncbi.nlm.nih.gov/.

Another aspect of the invention pertains to vectors, preferably expression vectors, containing a nucleic acid encoding a variant alpha-amylase polypeptide of the invention.

As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. The terms "plasmid" and "vector" can be used interchangeably herein as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vector includes one or more regulatory sequences, selected on the basis of the host cells to be used for expression, which is operatively linked to the nucleic acid sequence to be expressed. Within a recombinant expression vector, "operatively linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signal). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cells and those which direct expression of the nucleotide sequence only in a certain host cell (e.g. tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, encoded by nucleic acids as described herein (e.g. an alpha-amylase variant of SEQ ID NO: 2, for example a functional equivalent or fragment, or a fusion protein comprising one or more of such variants).

The recombinant expression vectors of the invention can be designed for expression of variant proteins of the invention in prokaryotic or eukaryotic cells. For example, a variant protein of the invention can be expressed in bacterial cells such as E. coli, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression vectors useful in the present invention include chromosomal-, episomal- and virus-derived vectors e.g., vectors derived from bacterial plasmids, bacteriophage, yeast episome, yeast chromosomal elements, viruses such as baculoviruses, papova viruses, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids.

The DNA insert should be operatively linked to an appropriate promoter, such as the phage lambda PL promoter, the E. coli lac, trp and tac promoters, the SV40 early and late promoters and promoters of retroviral LTRs, to name a few. Other suitable promoters will be known to the skilled person. In a specific embodiment, promoters are preferred that are capable of directing a high expression level of alpha-amylase in filamentous fungi. Such promoters are known in the art. The expression constructs may contain sites for transcription initiation, termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-percipitation, DEAE-dextran-mediated transfection, transduction, infection, lipofection, cationic lipidmediated transfection or electroporation. Suitable methods for transforming or transfecting host cells can be found in Sambrook, et al. (Molecular Cloning: A Laboratory Manual, 2nd, ed. Cold Spring Harbor Laboratory, Cold Spring Harbor Laboratory Press, Cold Spring Harbor, N. Y., 1989), Davis et al., Basic Methods in Molecular Biology (1986) and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methatrexate. Nucleic acid encoding a selectable marker can be introduced into a host cell on the same vector as that encoding a variant protein of the invention or can be introduced on a separate vector. Cells stably transfected with the introduced nucleic acid can be identified by drug selection (e.g. cells that have incorporated the selectable marker gene will survive, while the other cells die).

Expression of proteins in prokaryotes is often carried out in E. coli with vectors containing constitutive or inducible promoters directing the expression of either fusion or non-fusion proteins.

The nucleic acid sequences according to the invention can be cloned in a suitable vector and after introduction in a suitable host, the sequence can be expressed to produce the corresponding alpha-amylase variants according to standard cloning and expression techniques, which are known to the person skilled in the art (e.g., as described in (Sambrook & Russell, Molecular Cloning: A Laboratory Manual, 3rd Ed., CSHL Press, Cold Spring Harbor, N. Y., 2001). The invention also relates to such vectors comprising a nucleic acid sequence according to the invention.

Suitable vectors are the vectors normally used for cloning and expression and are known to the person skilled in the art. Examples of suitable vectors for expression in E. coli are given e.g. in table 1 in Makrides, S. C., Microbiological Reviews, Vol. 60, No. 3, (1996), 512-538. Preferably, the vector contains a promoter upstream of the cloning site containing the nucleic acid sequence encoding the polypeptide with alpha-amylase activity, which can be switched on after the host has been grown to express the corresponding polypeptide having alpha-amylase activity. Promoters, which can be switched on and off are known to the person skilled in the art and are for example the lac promoter, the aroH promoter, the araBAD promoter, the T7 promoter, the trc promoter, the tac promoter and the trp promoter. Particularly useful in the framework of the invention are for example the vectors as described in WO 00/66751, e.g. pKAFssECtrp or pKAFssECaro without the insert, the penicillin G acylase gene. Suitable hosts are the hosts normally used for cloning and expression and are known to the person skilled in the art. Examples of suitable host strains are for example Echerichia coli strains, e.g. E. coli TOP10F', TOP10, DH10B, DH5a, HB101, W3110, BL21(DE3) and BL21 (DE3)pLysS. Particularly useful in the framework of the invention are Escherichia coli K-12 strains, e.g. DH1, HB101, RV308, RR1, W3110, C600 and/or derivatives of these strains. The choice of the vector can sometimes depend on the choice of the host and vice versa. If e.g. a vector with the araBAD promoter is being used, an E. coli host strain that is unable to break down the arabinose inducer (ara-), is strongly preferred.

Fusion vectors add a number of amino acids to a protein encoded therein, e.g. to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein.

As indicated, the expression vectors will preferably contain selectable markers. Such markers include dihydrofolate reductase or neomycin resistance for eukaryotic cell culture and tetracyline or ampicillin resistance for culturing in *E. coli* and other bacteria. Representative examples of appropriate host include bacterial cells, such as *E. coli, Streptomyces Salmonella typhimurium* and certain *Bacillus* species; fungal cells such as *Aspergillus* species, for example *A. niger, A. oryzae* and *A. nidulans*, such as yeast such as *Kluyveromyces*, for example *K. lactis* and/or *Puchia*, for example *P. pastoris*; insect cells such as Drosophila S2 and Spodoptera Sf9; animal cells such as CHO, COS and Bowes melanoma; and plant cells. Appropriate culture mediums and conditions for the above-described host cells are known in the art.

Vectors preferred for use in bacteria are for example disclosed in WO-A1-2004/074468, which are hereby enclosed by reference. Other suitable vectors will be readily apparent to the skilled artisan.

Known bacterial promotors suitable for use in the present invention include the promoters disclosed in WO-A1-2004/074468, which are hereby incorporated by reference.

Transcription of the DNA encoding a variant of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at by 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretation signal may be incorporated into the expressed polypeptide. The signals may be endogenous to the polypeptide or they may be heterologous signals.

A variant of the invention may be expressed in form such that it may include additional heterologous functional regions, for example secretion signals. A variant of the invention may also comprise, for example, a region of additional amino acids, particularly charged amino acids, added to the N-terminus of the polypeptide for instance to improve stability and persistence in the host cell, during purification or during subsequent handling and storage. Also, peptide moieties may be added to a variant of the invention to facilitate purification, for example by the addition of histidine residues or a T7 tag.

The variants of the invention, such as proteins of the present invention or functional equivalents thereof, e.g., biologically active portions and fragments thereof, can be operatively linked to a non-variant polypeptide (e.g., heterologous amino acid sequences) to form fusion proteins. A "non-variant polypeptide" in this context refers to a polypeptide having an amino acid sequence corresponding to a protein which is not substantially homologous to a variant alpha-amylase of the invention.

Within a fusion protein, the variant of the invention can correspond to a full length sequence or a biologically active fragment of a polypeptide of the invention. In a preferred embodiment, a fusion protein of the invention comprises at least two biologically active portions. Within the fusion protein, the term "operatively linked" is intended to indicate that the variant polypeptide and the non-variant polypeptide are fused in-frame to each other. The non-variant polypeptide can be fused to the N-terminus or C-terminus of the variant polypeptide.

Expression and secretion of a variant alpha-amylase may be enhanced by expressing the variant in the form of a fusion protein. In this context, a nucleic acid sequence may encode for a fusion protein comprising pre-alpha-amylase or alpha-amylase. More specifically, the fusion partner may be glucoamylase or a fragment thereof. In one embodiment the pre-alpha-amylase or alpha-amylase, or a fusion protein thereof, is secreted over the host cell membrane.

For example, in one embodiment, the fusion protein is a fusion protein in which the variant sequence/s is/are fused to the C-terminus of the GST sequences. Such fusion proteins can facilitate the purification of a recombinant variant according to the invention. In another embodiment, the fusion protein is a variant of the invention containing a heterologous signal sequence at its N-terminus. In certain host cells (e.g., mammalian and yeast host cells), expression and/or secretion of a variant of the invention can be increased through use of a hetereologous signal sequence.

In another example, the gp67 secretory sequence of the baculovirus envelope protein can be used as a heterologous signal sequence (Current Protocols in Molecular Biology, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokarytic heterologous signal sequences include the phoA secretory signal (Sambrook et al., supra) and the protein A secretory signal (Pharmacia Biotech; Piscataway, N.J.).

A signal sequence can be used to facilitate secretion and isolation of a variant of the invention. Signal sequences are typically characterized by a core of hydrophobic amino acids, which are generally cleaved from the mature protein during secretion in one or more cleavage events. Such signal peptides contain processing sites that allow cleavage of the signal sequence from the mature proteins as they pass through the secretory pathway. The signal sequence may direct secretion of the variant, such as from a eukaryotic host into which the expression vector is transformed, and the signal sequence may then be subsequently or concurrently cleaved. The variant of the invention may then be readily purified from the extracellular medium by known methods. Alternatively, the signal sequence can be linked to the variant of interest using a sequence, which facilitates purification, such as with a GST domain. Thus, for instance, the sequence encoding the variant of the invention may be fused to a marker sequence, such as a sequence encoding a peptide, which facilitates purification of the fused variant of the invention. In certain preferred embodiments of this aspect of the invention, the marker sequence is a hexa-histidine peptide, such as the tag provided in a pQE vector (Qiagen, Inc.), among others, many of which are commercially available. As described in Gentz et al, Proc. Natl. Acad. Sci. USA 86:821-824 (1989), for instance, hexa-histidine provides for convenient purification of the fusion protein. The HA tag is another peptide useful for purification which corresponds to an epitope derived of influenza hemaglutinin protein, which has been described by Wilson et al., Cell 37:767 (1984), for instance.

A fusion protein of the invention may be produced by standard recombinant DNA techniques. For example, DNA fragments coding for the different polypeptide sequences are ligated together in frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers, which give rise to complementary overhangs between two consecutive gene fragments which can subsequently be annealed and reamplified to generate a chimeric gene sequence (see, for example, Current Protocols in Molecular Biology, eds. Ausubel et al. John Wiley & Sons: 1992). Moreover, many expression vectors are commercially available that already encode a fusion moiety (e.g, a GST polypeptide). A variant-encoding nucleic acid can be cloned into such an expression vector such that the fusion moiety is linked in-frame to the said variant.

The terms "functional equivalents" and "functional variants" are used interchangeably herein. Functional equivalents according to the invention are isolated DNA fragments that encode a polypeptide that exhibits a particular function of a variant as defined herein. Functional equivalents therefore also encompass biologically active fragments and are themselves encompassed within the term "a variant" of the invention.

Preferably, a functional equivalent of the invention comprises one or more of the substitutions described herein. However, a functional equivalent may comprise one or more modifications in addition to the substitutions described above.

Functional nucleic acid equivalents may typically contain silent mutations or mutations that do not alter the biological function of encoded polypeptide. Accordingly, the invention provides nucleic acid molecules encoding a variant alpha-amylase protein that contains changes in amino acid residues that are not essential for a particular biological activity. Such variant proteins differ in amino acid sequence from the parent alpha-amylase sequence from which they are derived yet retain at least one biological activity thereof, preferably they retain at least alpha-amylase activity. In one embodiment the isolated nucleic acid molecule comprises a nucleotide sequence encoding a protein, wherein the protein comprises a substantially homologous amino acid sequence of at least about 60%, 65%, 70%, 75%, 80%, 85%, 90%, 95%, 96%, 97%, 98%, 99% or more homologous to the reference amino acid sequence (for example that shown in SEQ ID NO: 2).

As defined herein, the term "substantially homologous" refers to a first amino acid or nucleotide sequence which contains a sufficient or minimum number of identical or equivalent (e.g., with similar side chain) amino acids or nucleotides to a second amino acid or nucleotide sequence such that the first and the second amino acid or nucleotide sequences have a common domain. For example, amino acid or nucleotide sequences which contain a common domain having about 60%, preferably 65%, more preferably 70%, even more preferably 75%, 80%, 85%, 90%, 95%, 96%, 97%, 98% or 99% identity or more are defined herein as sufficiently identical.

The skilled person will recognise that changes can be introduced by mutation into the nucleotide sequences according to the invention thereby leading to changes in the amino acid sequence of the resulting protein without substantially altering the function of such a protein.

Accordingly, an alpha-amylase variant of the invention is preferably a protein which comprises an amino acid sequence at least about 60%, 65%, 70%, 75%, 80%, 85%, 90%, 95%, 96%, 97%, 98%, 99% or more homologous to the reference amino acid sequence, for example that shown in SEQ ID NO: 2, and typically also retains at least one functional activity of the reference polypeptide. Variants of the invention, for example functional equivalents of a protein according to the invention, can also be identified e.g. by screening combinatorial libraries of mutants, e.g. truncation mutants, of the protein of the invention for alpha-amylase activity. In one embodiment, a variegated library of variants is generated by combinatorial mutagenesis at the nucleic acid level. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g. for phage display). There are a variety of methods that can be used to produce libraries of potential variants of the polypeptides of the invention from a degenerate oligonucleotide sequence. Methods for synthesizing degenerate oligonucleotides are known in the art (see, e.g., Narang (1983) Tetrahedron 39:3; Itakura et al. (1984) Annu. Rev. Biochem. 53:323; Itakura et al. (1984) Science 198: 1056; Ike et al. (1983) Nucleic Acid Res. 11:477).

In addition, libraries of fragments of the sequence encoding a polypeptide of the invention can be used to generate a variegated population of polypeptides for screening a subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the protein of interest.

Several techniques are known in the art for screening gene products of combinatorial libraries made by point mutations of truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan (1992) Proc. Natl. Acad. Sci. USA 89:7811-7815; Delgrave et al. (1993) Protein Engineering 6(3): 327-331).

Fragments of a polynucleotide according to the invention may also comprise polynucleotides not encoding functional polypeptides. Such polynucleotides may function as probes or primers for a PCR reaction.

Nucleic acids according to the invention irrespective of whether they encode functional or non-functional polypeptides can be used as hybridization probes or polymerase chain reaction (PCR) primers. Uses of the nucleic acid molecules of the present invention that do not encode a polypeptide having alpha-amylase activity include, inter alia, (1) in situ hybridization (e.g. FISH) to metaphase chromosomal spreads to provide precise chromosomal location of an alpha-amylase-encoding gene as described in Verma et al., Human Chromosomes: a Manual of Basic Techniques, Pergamon Press, New York (1988); (2) Northern blot analysis for detecting expression of alpha-amylase mRNA in specific tissues and/or cells; and (3) probes and primers that can be used as a diagnostic tool to analyse the presence of a nucleic acid hybridizable to such a probe or primer in a given biological (e.g. tissue) sample.

Variants of a given reference alpha-amylase enzyme can be obtained by the following standard procedure:

Mutagenesis (error-prone, doped oligo, spiked oligo) or synthesis of variants

Transformation in, for example *B. subtilis*

Cultivation of transformants, selection of transformants

Expression

Optional purification and concentration

Primary Screening

Identification of an improved variant (for example in relation to specific activity)

A method of the invention for identifying a variant alpha-amylase comprises comprises:

a) selecting a reference alpha-amylase polypeptide;

b) substituting at least one amino acid residue corresponding to any of 1, 2, 3, 4, 5, 6, 7, 8, 9, 10, 11, 12, 13, 14, 15, 6, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 251, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 351, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 551, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 651, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, said positions being defined with reference to SEQ ID NO: 2;

c) optionally substituting one or more further amino acids as defined in b);

d) preparing the variant resulting from steps a)-c);

e) determining a property of the variant, for example as set out in the description; and f) selecting a variant an altered property in comparison to the reference alpha-amylase polypeptide.

In an embodiment of the invention for identifying a variant alpha-amylase comprises said method comprises:

a) selecting a reference alpha-amylase polypeptide;

b) substituting at least one amino acid residue corresponding to any of 4, 6, 13, 14, 15, 16, 20, 45, 47, 51, 54, 61, 68, 69, 70, 71, 72, 73, 74, 75, 77, 78, 80, 82, 87, 88, 94, 95, 100, 103, 104, 117, 124, 125, 126, 128, 130, 133, 134, 136, 143, 144, 146, 168, 174, 177, 178, 183, 186, 188, 189, 190, 194, 195, 199, 200, 201, 204, 207, 210, 214, 217, 219, 222, 225, 227, 233, 234, 235, 236, 240, 251, 252, 254, 258, 259, 260, 261, 262, 263, 264, 266, 267, 269, 271, 273, 281, 282, 283, 284, 286, 288, 299, 322, 323, 325, 327, 328, 331, 334, 350, 356, 358, 367, 370, 371, 374, 377, 378, 388, 391, 414, 421, 422, 445, 450, 467, 488, 505, 536, 548, 554, 583, 588, 603, 637, 648, 651, 652, 660, 676, 677, said positions being defined with reference to SEQ ID NO: 2;

c) optionally substituting one or more further amino acids as defined in b);

d) preparing the variant resulting from steps a)-c);

e) determining a property of the variant, for example as set out in the description; and f) selecting a variant an altered property in comparison to the reference alpha-amylase polypeptide.

In an embodiment the invention relates to a method of producing an alpha-amylase polypeptide variant according to the invention, which method comprises:

a) selecting a reference alpha-amylase polypeptide;

b) substituting at least one amino acid residue corresponding to any of 1, 2, 3, 4, 5, 6, 7, 8, 9, 10, 11, 12, 13, 14, 15, 6, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200,
201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 251, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 351, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 451, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 551, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619,
620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 651, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, said positions being defined with reference to SEQ ID NO: 2;

c) optionally substituting one or more further amino acids as defined in b);

d) preparing the variant resulting from steps a)-c);

e) determining a property of the variant, for example as set out in the description; and f) selecting a variant an altered property in comparison to the reference alpha-amylase polypeptide.

In an embodiment in the method of producing an alpha-amylase polypeptide variant according to the invention, the reference alpha-amylase polypeptide has the sequence set out in SEQ ID NO: 2.

Preferably in step b) of the method according to the invention at least one amino acid residue corresponding to any of 4, 6, 13, 14, 15, 16, 20, 45, 47, 51, 54, 61, 68, 69, 70, 71, 72, 73, 74, 75, 77, 78, 80, 82, 87, 88, 94, 95, 100, 103, 104, 117, 124, 125, 126, 128, 130, 133, 134, 136, 143, 144, 146, 168, 174, 177, 178, 183, 186, 188, 189, 190, 194, 195, 199, 200, 201, 204, 207, 210, 214, 217, 219, 222, 225, 227, 233, 234, 235, 236, 240, 251, 252, 254, 258, 259, 260, 261, 262, 263, 264, 266, 267, 269, 271, 273, 281, 282, 283, 284, 286, 288, 299, 322, 323, 325, 327, 328, 331, 334, 350, 356, 358, 367, 370, 371, 374, 377, 378, 388, 391, 414, 421, 422, 445, 450, 467, 488, 505, 536, 548, 554, 583, 588, 603, 637, 648, 651, 652, 660, 676, 677, is substituted, said positions being defined with reference to SEQ ID NO: 2. The reference polypeptide may have at least about 80% homology with SEQ ID NO: 2.

In another embodiment, the invention features cells, e.g., transformed host cells or recombinant host cells that contain a nucleic acid encompassed by the invention. A "transformed cell" or "recombinant cell" is a cell into which (or into an ancestor of which) has been introduced, by means of recombinant DNA techniques, a nucleic acid according to the invention. Both prokaryotic and eukaryotic cells are included, e.g., bacteria, fungi, yeast, and the like, especially preferred are cells from yeasts, for example, *K. lactis*. Host cells also include, but are not limited to, mammalian cell lines such as CHO, VERO, BHK, HeLa, COS, MDCK, 293, 3T3, WI38, and choroid plexus cell lines.

Examples of suitable bacterial host organisms are gram positive bacterial species such as Bacillaceae including *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium* and *Bacillus thuringiensis, Streptomyces* species such as *Streptomyces murinus*, lactic acid bacterial species including *Lactococcus* spp. such as *Lactococcus lactis, Lactobacillus* spp. including *Lactobacillus reuteri, Leuconostoc* spp. and *Streptococcus* spp. Alternatively, strains of a gram negative bacterial species such as a species belonging to Enterobacteriaceae, including *E. coli* or to Pseudomonadaceae may be selected as the host organism.

A suitable yeast host organism may advantageously be selected from a species of *Saccharomyces* including *Saccharomyces cerevisiae* or a species belonging to *Schizosaccharomyces*. Further useful yeast host organisms include *Pichia* spp. such as methylotrophic species hereof, including *Pichia pastoris*, and *Klyuveromyces* spp. including *Klyuveromyces lactis*.

Suitable host organisms among filamentous fungi include species of *Acremonium, Aspergillus, Fusarium, Humicola, Mucor, Myceliophtora, Neurospora, Penicillium, Thielavia, Tolypocladium* or *Trichoderma*, such as e.g. *Aspergillus aculeatus, Aspergillus awamori, Aspergillus foetidus, Aspergillus japonicus, Aspergillus oryzae, Aspergillus nidulans* or *Aspergillus niger*, including *Aspergillus nigervar. awamori, Fusarium bactridioides, Fusarium cereals, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichiodes, Fusarium sulphureum, Fusarium torulosum, Fusarium trichothecioides, Fusarium venenatum, Humicola insolens, Humicola languinosa, Mucor miehei, Myceliophtora thermophila, Neurospora crassa, Penicillium chrysogenum, Penicillium camenbertii, Penicil-*

*lium purpurogenum, Rhizomucor miehei, Thielavia terestris, Trichoderma harzianum, Trichoderma koningii, Trichoderma longibrachiatum, Trichoderma reesii* or *Trochoderma viride.*

A host cell can be chosen that modulates the expression of the inserted sequences, or modifies and processes the product encoded by the incorporated nucleic acid sequence in a specific, desired fashion. Such modifications (e.g., glycosylation) and processing (e.g., cleavage) of protein products may facilitate optimal functioning of the encoded protein.

Various host cells have characteristic and specific mechanisms for post-translational processing and modification of proteins and gene products. Appropriate cell lines or host systems familiar to those of skill in the art of molecular biology and/or microbiology can be chosen to ensure the desired and correct modification and processing of the foreign protein expressed. To this end, eukaryotic host cells that possess the cellular machinery for proper processing of the primary transcript, glycosylation, and phosphorylation of the gene product can be used. Such host cells are well known in the art.

If desired, a stably transfected cell line can produce a variant according to the invention. A number of vectors suitable for stable transfection of mammalian cells are available to the public, methods for constructing such cell lines are also publicly known, e.g., in Ausubel et al. (supra).

In an embodiment the enzyme composition according to the invention is provided in a dry form, to allow easy addition to the dough, the dough ingredients, but liquid forms are also possible. A liquid form includes without limitation an emulsion, a suspension and a solution. Irrespective of the formulation of the enzyme composition, any additive or additives known to be useful in the art to improve and/or maintain the enzyme's activity, the quality of the dough and/or the baked product may be applied.

The present invention further discloses a composition comprising the alpha-amylase variants according to the invention and one or more components selected from the group consisting of milk powder, gluten, granulated fat, an additional enzyme, an amino acid, a salt, oxidants (including ascorbic acid, bromate and Azodicarbonamide (ADA)), reducing agents (including L-cysteine), emulsifiers (including mono/di glycerides, monoglycerides such as glycerol monostearate (GMS), sodium stearoyl lactylate (SSL), calcium stearoyl lactylate (CSL), polyglycerol esters of fatty acids (PGE) and diacetyl tartaric acid esters of mono- and diglycerides (DATEM), gums (including guargum and xanthangum), flavours, acids (including citric acid, propionic acid), starch, modified starch, gluten, humectants (including glycerol) and preservatives.

In an aspect of the composition according to the invention the additional enzyme may include including a further alpha-amylase, such as a fungal alpha-amylase (which may be useful for providing sugars fermentable by yeast and retarding staling), beta-amylase, a cyclodextrin glucanotransferase, a protease, a peptidase, in particular, an exopeptidase (which may be useful in flavour enhancement), transglutaminase, triacyl glycerol lipase (which may be useful for the modification of lipids present in the dough or dough constituents so as to soften the dough), galactolipase, phospholipase, cellulase, hemicellulase, in particular a pentosanase such as xylanase (which may be useful for the partial hydrolysis of pentosans, more specifically arabinoxylan, which increases the extensibility of the dough), protease (which may be useful for gluten weakening in particular when using hard wheat flour), protein disulfide isomerase, e.g., a protein disulfide isomerase as disclosed in WO 95/00636, glycosyltransferase, peroxidase (which may be useful for improving the dough consistency), laccase, or oxidase, hexose oxidase, e.g., a glucose oxidase, aldose oxidase, pyranose oxidase, lipoxygenase or L-amino acid oxidase (which may be useful in improving dough consistency) or a protease.

In an embodiment of the composition according to the invention the additional enzyme is a lipolytic enzyme, preferably a phospholipase, a galactolipase or an enzyme having both phospholipase and galactolipase activity.

In an embodiment of the composition according to the invention the additional enzyme is a phospholipase.

In an embodiment of the composition according to the invention the additional enzyme is a galactolipase.

In an embodiment of the enzyme composition according to the invention the additional enzyme is an enzyme having both phospholipase and galactolipase activity.

Lipolytic Enzyme

A lipolytic enzyme, also referred to herein as lipase, is an enzyme that hydrolyses triacylglycerol and/or galactolipid and or phospholipids.

Lipase activity may be determined spectrophotometrically by using the chromogenic substrate p-nitrophenyl palmitate (pNPP, Sigma N-2752). In this assay the pNPP is dissolved in 2-propanol (40 mg pNPP per 10 ml 2-propanol (Merck 1.09634)) and suspended in 100 mM Acetate buffer pH=5.0 containing 1.0% Triton X-100 (Merck 1.12298) (5 ml substrate in 45 ml buffer). The final substrate concentration is 1.1 mM. The lipase is incubated with this substrate solution at 37° C. for 10 minutes. The reaction is stopped by addition of stop buffer 2% TRIS (Merck 1.08387)+1% Triton X-100 in a 1:1 ratio with respect to the reaction mixture and subsequently the formed p-nitrophenol (pNP) is measured at 405 nm. This assay can also be applied at different pH values in order to determine pH dependence of a lipase. It should be understood that at different pH values different buffers might be required or that different detergents might be necessary to emulsify the substrate. One lipase unit is defined as the amount of enzyme that liberates 1 micromole of p-nitrophenol per minute at the reaction conditions stated. It should be understood that it is not uncommon practice in routine analysis to use standard calibration enzyme solutions with known activity determined in a different assay to correlate activity a given assay with units as would be determined in the calibration assay.

Alternatively, lipase activity may be determined by using 2, 3-mercapto-1-propanol-tributyrate (TBDMP) as a substrate. Lipase hydrolyses the thioester bond(s) of TBDMP thereby liberating butanoic acid and 2, 3-mercapto-1-propanol-dibutyrate, 2, 3-mercapto-1-propanol-monobutyrate or 2, 3-mercapto-1-propanol. The liberated thiol groups are titrated in a subsequent reaction with 4, 4, -dithiodipyridine (DTDP) forming 4-thiopyridone. The latter is in a tautomeric equilibrium with 4-mercapthopyridine which absorbs at 334 nm. The reaction is carried out in 0.1 M acetate buffer pH 5.0 containing 0.2% Triton-X100, 0.65 mM TBDMP and 0.2 mM DTDP at 37° C. One lipase unit is defined as the amount of enzyme that liberates 1 micromole of 4-thiopyridone per minute at the reaction conditions stated.

In addition to spectrophotometric measurement lipase activity may also be determined using titrimetric measurement. For example the esterase activity of a lipolytic enzyme may be measured on tributyrin as a substrate according to Food Chemical Codex, Forth Edition, National Academy Press, 1996, p 803.

A phospholipase is an enzyme that catalyzes the release of fatty acyl groups from a phospholipid. It may be a phospholipase A2 (PLA2, EC 3.1.1.4) or a phospholipase A1 (EC 3.1.1.32). It may or may not have other activities such as triacylglycerol lipase (EC 3.1.1.3) and/or galactolipase (EC 3.1.1.26) activity.

The phospholipase may be a native enzyme from mammalian or microbial sources.

An example of a mammalian phospholipase is pancreatic PLA2, e.g. bovine or porcine PLA2 such as the commercial product Lecitase 10L (porcine PLA2, product of Novozymes A/S).

Microbial phospholipases may be from *Fusarium*, e.g. *F. oxysporum* phospholipase A1 (WO 1998/026057), *F. venenatum* phospholipase A1 (described in WO 2004/097012 as a phospholipase A2 called FvPLA2), from Tuber, e.g. *T. borchii* phospholipase A2 (called TbPLA2, WO 2004/097012).

The phospholipase may also be a lipolytic enzyme variant with phospholipase activity, e.g. as described in WO 2000/032758 or WO 2003/060112.

The phospholipase may also catalyze the release of fatty acyl groups from other lipids present in the dough, particularly wheat lipids. Thus, the phospholipase may have triacylglycerol lipase activity (EC 3.1.1.3) and/or galactolipase activity (EC 3.1.1.26). The phospholipase may be a lipolytic enzyme as described in WO2009/106575, such as the commercial product Panamore®, product of DSM.

In an embodiment the additional enzyme is a lipolytic enzyme, including a triacyl glycerol lipase, a phospholipase, a galactolipase and an enzyme having both galactolipase and phospholipase activity.

The triacyl glycerol lipase may be a fungal lipase, preferably from *Rhizopus, Aspergillus, Candida, Penicillum, Thermomyces,* or *Rhizomucor*. In an embodiment the triacyl glycerol lipase is from *Rhizopus*, in a further embodiment a triacyl glycerol lipase from *Rhizopus oryzae* is used. Optionally a combination of two or more triacyl glycerol lipases may be used In a further embodiment the lipolytic enzyme is a phospholipase or an enzyme having both galactolipase and phospholipase activity. Such lipases are known to be active on the endogenous lipids of wheat and on extraneous lipid sources, for example as provided by added shortening fat or from lecithin. Preferentially the lipase cleaves polar lipids and has phospholipase activity, galactolipase activity or a combination of phospholipase and galactolipase activity to create lysophospholipids, such as lysophoshotidyl choline, and lysogalactolipids such as digalactosylmonoglyceride. The specificity of the lipase can be shown through in vitro assay making use of appropriate substrate, for example triacylglycerol lipid, phosphotidylcholine and diglactosyl-diglyceride, or preferably through analysis of the reactions products that are generated in the dough during mixing and fermentation.

Panamore®, Lipopan® F, Lipopan® 50 and Lipopan® S are commercialised to standardised lipolytic activity, using a measurement of DLU for Panamore® from DSM and a measurement of LU for the Lipopan® family from Novozymes. DLU is defined as the amount of enzyme needed to produce 1 micromol/min of p-nitrophenol from p-nitrophenyl palmitate at pH 8.5 at 37° C., while LU is defined as the amount of enzyme needed to produce 1 micromol/min of butyric acid from tributyrin at pH 7 at 30° C. Lipases are optimally used with the alpha-amylase of the invention at 2-850 DLU/kg flour or at 50-23500 LU/kg flour.

In an embodiment of the enzyme composition according to the invention the additional enzyme is Panamore® as described in WO2009/106575.

In an embodiment of the enzyme composition of the invention the additional enzyme is an enzyme as described in WO9826057.

In an aspect of the enzyme composition according to the invention the additional enzyme is an enzyme as described in U.S. RE38,507.

In an aspect of the enzyme composition according to the invention the additional enzyme is an enzyme as described in WO 9943794, in particular in EP1058724B1.

If one or more additional enzyme activities are to be added in accordance with the methods of the present invention, these activities may be added separately or together with the polypeptide according to the invention, for example as the enzyme composition according to the invention, which includes a bread-improving composition and/or a dough-improving composition. The other enzyme activities may be any of the enzymes described above and may be dosed in accordance with established baking practices.

The triacyl glycerol lipase may be a fungal lipase, preferably from *Rhizopus, Aspergillus, Candida, Penicillum, Thermomyces,* or *Rhizomucor*. In an embodiment the triacyl glycerol lipase is from *Rhizopus*, in a further embodiment a triacyl glycerol lipase from *Rhizopus oryzae* is used. Optionally a combination of two or more triacyl glycerol lipases may be used Cellulase A cellulase may be from *A. niger* or from *Trichoderma reesei*.

Amyloglucosidase

The amyloglucosidase, may be an amyloglucosidase from *Aspergillus* such as from *A. oryzae* or *A. niger*, preferably from *A. niger*.

Additional Enzyme

The additional enzyme may include without limitation an enzyme as disclosed in any of of WO2006/032281, WO2008/148845, WO2006/012902, WO2006/012899, WO2004/081171, WO99/43793 or WO2005/066338.

The additional enzyme may include a G4-forming amylase.

A G4-forming amylase is an enzyme that is inter alia capable of catalysing the degradation of starch. In particular it is capable of cleaving α-D-(⊢>4) O-glycosidic linkages in starch. It may be referred to as a glucan 1, 4-alpha-maltotetraohydrolase (EC 3.2.1.60). It may also be referred as a maltotetraohydrolase.

*Pseudomonas saccharophila* (GenBank Acc. No. X16732) expresses a G4-forming amylase.

The G4-forming amylase may be a G-4 forming amylase as expressed by *Pseudomonas saccharophila*, the polypeptide as set out in SEQ ID NO:4 or a variant thereof. The G-4 forming amylase is capable of producing maltotetraose from either liquefied starch or other source of maltodextrins at a high temperature e.g. about 60° C. to about 75° C.

As used herein the term starch refers to any material comprised of the complex polysaccharide carbohydrates of plants such as corn, comprised of amylose and amylopectin.

The amylase with G4-forming activity was dosed at a level to achieve the appropriate effect in baking. The assay to determine the activity used is known in the art such as Betamyl assay (Megazyme); Phadebas assay (Pharmacia & Upjohn Diagnostics AB); NBAU (Ceralpha, Megazyme as described herein)

Suitable G4-forming amylases may be G4-forming amylases described in any one of WO9950399, WO2005007818, WO2004111217, WO2005003339, WO2005007818, WO2005007867, WO2006003461, WO2007007053, WO2007148224, WO2009083592, WO2009088465.

A composition according to the invention comprises the variant polypeptide of the invention or one obtainable by a method of the invention for identifying a variant alpha-amylase.

A pre-mix according to the invention comprises flour and the variant polypeptide of the invention or one obtainable by a method of the invention for identifying a variant alpha-amylase.

The invention further relates to use of a variant polypeptide according to the invention or of a composition according to the invention or of a pre-mix according to the invention in the preparation of a dough and/or a baked product.

The invention further relates to dough comprising a variant polypeptide according to the invention or a composition according to the invention or a pre-mix according to the invention.

Preparing a dough according to the invention may comprise the step of combining the alpha-amylase variant according to the invention or the composition according to the invention and at least one dough ingredient. 'Combining' includes without limitation, adding the polypeptide or the enzyme composition according to the invention to the at least one dough ingredient, adding the at least one dough ingredient to the polypeptide or the enzyme composition according to the invention, mixing the polypeptide according to the invention and the at least one dough ingredient.

A dough ingredient includes any component selected from flour, egg, water, salt, sugar, flavours, fat (including butter, margarine, oil and shortening), baker's yeast, a chemical leavening system, milk, oxidants (including ascorbic acid, bromate and Azodicarbonamide (ADA)), reducing agents (including L-cysteine), emulsifiers (including mono/di glycerides, mono glycerides such as glycerol monostearate (GMS), sodium stearoyl lactylate (SSL), calcium stearoyl lactylate (CSL), polyglycerol esters of fatty acids (PGE) and diacetyl tartaric acid esters of mono- and diglycerides (DATEM), gums (including guargum and xanthangum), acids (including citric acid, propionic acid), starch, modified starch, gluten, humectants (including glycerol) and preservatives.

In an aspect to prepare a dough according to the invention, such method may comprise the steps of combining the alpha-amylase variant according to the invention and at least one component selected from flour, egg, water, salt, sugar, flavours, fat (including butter, margarine, oil and shortening), baker's yeast, a chemical leavening systems, milk, oxidants (including ascorbic acid, bromate and Azodicarbonamide (ADA)), reducing agents (including L-cysteine), emulsifiers (including mono/di glycerides, monoglycerides such as glycerol monostearate (GMS), sodium stearoyl lactylate (SSL), calcium stearoyl lactylate (CSL), polyglycerol esters of fatty acids (PGE) and diacetyl tartaric acid esters of mono- and diglycerides (DATEM), gums (including guargum and xanthangum), acids (including citric acid, propionic acid), starch, modified starch, gluten, humectants (including glycerol) and preservatives.

In an aspect to prepare a dough according to the invention, such method may comprise the steps of combining the composition according to the invention and at least one component selected from flour, egg, water, salt, sugar, flavours, fat (including butter, margarine, oil and shortening), baker's yeast, a chemical leavening systems, milk, oxidants (including ascorbic acid, bromate and Azodicarbonamide (ADA)), reducing agents (including L-cysteine), emulsifiers (including mono/di glycerides, monoglycerides such as glycerol monostearate (GMS), sodium stearoyl lactylate (SSL), calcium stearoyl lactylate (CSL), polyglycerol esters of fatty acids (PGE) and diacetyl tartaric acid esters of mono- and diglycerides (DATEM), gums (including guargum and xanthangum), acids (including citric acid, propionic acid), starch, modified starch, gluten, humectants (including glycerol) and preservatives.

'Combining' includes without limitation, adding the alpha-amylase variant according to the invention or the composition according to the invention to the at least one component indicated above, adding the at least one component indicated above to the alpha-amylase variant according to the invention or the composition according to the invention, mixing the alpha-amylase variant according to the invention or the composition according to the invention and the at least one component indicated above.

The invention also relates to the use of the alpha-amylase variant according to the invention in a number of industrial processes. Despite the long-term experience obtained with these processes, the alpha-amylase according to the invention may feature advantages over the enzymes currently used. Depending on the specific application, these advantages may include aspects like lower production costs, higher specificity towards the substrate, less antigenic, less undesirable side activities, higher yields when produced in a suitable microorganism, more suitable pH and temperature ranges, better tastes of the final product as well as food grade and kosher aspects.

In an embodiment the alpha-amylase variant according to the invention may be used in the food industry, including in food manufacturing.

An example of an industrial application of the alpha-amylase variant according to the invention in food is its use in baking applications. The alpha-amylase according to the invention may for example be used in baked products such as bread or cake. For example to improve quality of the dough and/or the baked product.

Yeast, enzymes and optionally additives are generally added separately to the dough.

Enzymes may be added in a dry, e.g. granulated form, in a liquid form or in the form of a paste. Additives are in most cases added in powder form. Suitable additives include oxidants (including ascorbic acid, bromate and Azodicarbonamide (ADA)), reducing agents (including L-cysteine), emulsifiers (including mono/di glycerides, monoglycerides such as glycerol monostearate (GMS), sodium stearoyl lactylate (SSL), calcium stearoyl lactylate (CSL), polyglycerol esters of fatty acids (PGE) and diacetyl tartaric acid esters of mono- and diglycerides (DATEM), gums (including guargum and xanthangum), flavours, acids (including citric acid, propionic acid), starch, modified starch, gluten, humectants (including glycerol) and preservatives.

The preparation of a dough from the dough ingredients is well known in the art and includes mixing of said ingredients and optionally one or more moulding and fermentation steps.

The invention further relates to a process for the production of a baked product, which method comprises baking the dough according to the invention. In an embodiment of the process for the production of baked product the baked product is bread or cake.

In an aspect, the alpha-amylase variant according to the invention, the composition according to the invention or the pre-mix according to the invention may be used in the production of cake and in the production of a batter from which a cake can be made.

The alpha-amylase variant, enzyme composition according to the invention or the premix according to the invention may be used in the preparation of a wide range of cakes, including shortened cakes, such as for example pound cake and butter cake, and including foam cakes, such as for example meringues, sponge cake, biscuit cake, roulade, genoise and chiffon cake. Sponge cake is a type of soft cake based on wheat flour, sugar, baking powder and eggs (and optionally baking powder). The only fat present is from the egg yolk, which is sometimes added separately from the white. It is often used as a base for other types of cakes and desserts. A pound cake is traditionally prepared from one pound each of flour, butter, eggs, and sugar, optionally complemented with baking powder. In chiffon cake the butter/margarine has been replaced by oil. Sugar and egg yolk is decreased compared to pound or sponge cake and egg white content is increased.

A method to prepare a batter preferably comprises the steps of:
  a. preparing the batter of the cake by adding at least:
    i. sugar;
    ii. flour;
    iii. the alpha-amylase variant according to the invention;
    iv. at least one egg; and
    v. optionally a phospholipase.

A method to prepare a cake according to the invention further comprises the step of
  b. baking the batter to yield a cake.

The person skilled in the art knows how to prepare a batter or a cake starting from dough ingredients. Optionally one or more other ingredients can be present in the composition e.g. to allow reduction of eggs and/or fat in the cake, such as hydrocolloids, yeast extract, emulsifiers, calcium.

The invention further relates to a baked product obtainable by the process for the production of a baked product according to the invention or by the use according to the invention.

The above-mentioned industrial applications of the alpha-amylase enzyme according to the invention comprise only a few examples and this listing is not meant to be restrictive.

Other uses of the alpha-amylase variant according to the invention may include:
  the production of glucose, fructose and maltose syrups;
  production of starch hydrolysates such as maltodextrins;
  production of modified starches;
  modification of starch components in animal feed;
  replacement of malt in brewing;
  use in a glue including wall paper paste;
  use in plastic objects made using starch, including plastic bags made from polymerized starch films; and/or
  use in waste bread reprocessing.

In an aspect the invention relates to the use of a polypeptide having an amino acid sequence as set out in SEQ NO:7 and/or SEQ ID NO: 8 in the preparation of a dough and/or a baked product.

In an aspect the invention relates to a dough comprising a polypeptide having an amino acid sequence as set out in SEQ NO:7 and/or SEQ ID NO: 8.

In an aspect the invention relates to a pre-mix comprising a polypeptide having an amino acid sequence as set out in SEQ NO:7 and/or SEQ ID NO: 8.

In an aspect the invention relates a composition comprising a polypeptide having an amino acid sequence as set out in SEQ NO:7 and/or SEQ ID NO: 8 and one or more components selected from the group consisting of milk powder, gluten, granulated fat, an additional enzyme, an amino acid, a salt, oxidants, reducing agents, emulsifiers, sodium stearoyl lactylate, calcium stearoyl lactylate, polyglycerol esters of fatty acids and diacetyl tartaric acid esters of mono- and diglycerides, gums, flavours, acids, starch, modified starch, gluten, humectants and preservatives.

A reference herein to a patent document or other matter which is given as prior art is not to be taken as an admission that that document or matter was known or that the information it contains was part of the common general knowledge as at the priority date of any of the claims.

The disclosure of each reference set forth herein is incorporated herein by reference in its entirety.

The present invention is further illustrated by the following Examples:

EXAMPLES

The parent polypeptide may be produced as described in non-prepublished U.S. patent application Ser. No. 13/532, 072. The parent polypeptide may be produced as described in U.S. Pat. No. 8,426,182 B1.

Materials & Methods
NBAU Assay

Enzymatic activity of the alpha-amylase variant and of the parent polypeptide may be expressed as NBAU. One NBAU is defined as the amount of enzyme resulting in the release of 1 µmole of pNP (para-nitrophenol) per minute using the end blocked pNP-G7 Ceralpha substrate at pH=5.2 and T=37° C.

The principle of the NBAU activity test originates from a (manual) Megazyme α-amylase kit test (Ceralpha). The assay was made suitable for analyzer application. The assay is executed at pH 5.20 taking into account the pH optima for α-glucosidase and amyloglucosidase (pH range 5-6). The test is performed with a Konelab Arena 30 analyzer (Thermo Scientific, Vantaa, Finland).

The enzymatic activity is determined at 37° C. and pH 5.20 using a non-reducing-end blocked p-nitrophenyl malto-heptaoside substrate (=BPNPG7, Ceralpha) combined with excess levels of thermostable α-glucosidase and amyloglucosidase (both from Ceralpha: α-Amylase Reagent R-CAAR4, Megazyme, Ireland). Hydrolysis of the BPNPG7 substrate by an alpha-amylase results in p-nitrophenyl maltosaccharide fragments. The reaction is terminated (and colour developed) by the addition of an alkaline solution. The absorbance at a wavelength of 405 nm is determined and is a measure for enzymatic activity. Activity is calculated from a molar extinction coefficient determination, through a calibration with a para-nitrophenol solution of known concentration.

1) AACC Method 22-02.01
Measurement of Alpha-Amylase in Plant and Microbial Materials Using the Ceralpha® Method The alpha-amylase activity was analysed by measuring activity using a Megazyme CERALPHA alpha-amylase assay kit (Megazyme International Ireland Ltd., Co. Wicklow, Ireland) according to the manufacturer's instruction. All variants described in the examples showed alpha amylase activity in the CERALPHA assay. The reference polypeptide as set out in SEQ ID NO: 2 showed alpha amylase activity in the CERALPHA assay.

2)
Assay 2A Maltotriose Assay

This assay may be used to determine Activity on maltotriose substrate.

One Maltotriose Unit (MU) is defined as the amount of enzyme that liberates 1 µmole glucose per minute using maltotriose substrate under the following assay conditions.

Enzymatic activity was determined in a 30 minutes incubation at 37° C. and pH 5.0 using maltotriose as substrate. Enzymatic hydrolysis of maltotriose results in quantitative release of glucose, which is a measure for enzymatic activity.

Samples of approximately 0.4-4 mg/ml protein were diluted to a range between 0.0125 and 0.125 MU/ml in 100 mM citric acid buffer containing 1 g/L BSA, adjusted to pH 5.0 using 4 N NaOH. 10 mg/ml maltotriose substrate was prepared in 2.5 mM NaCl in MQ water. 160 microliter substrate was preheated for approximately 30 minutes in a PCR thermocycler set at 37° C. in a 96 wells PCR plate. 40 microliter of diluted sample was added to the preheated substrate in the thermocycler and mixed well by pipetting up and down several times. 30 minutes after sample addition, 20 microliter of 0.33 N NaOH was added and mixed well to terminate the reaction, and the PCR plate was taken out of the thermocycler. Released glucose was measured by incubation of 55 microliter of the terminated reaction mixture with 195 microliter of hexokinase monoreagent (Ecoline Glucose Hexokinase FS, DiaSys Diagnostic systems GmbH, Holzheim, Germany) for 15 minutes at room temperature in a flat bottom 96 wells plate. Air bubbles were removed from the surface by centrifugation, after which the absorbance at 340 nm was read using a microtiter plate reader. The amount of glucose released was determined relative to a glucose calibration line.

Assay 2B Sucrose Tolerance

As under Assay 2A), except that the substrate consisted of 10 mg/ml maltotriose to which 6.25 mg/ml sucrose was added.

Assay 2C Thermostability at pH 5

Samples of approximately 0.4-4 mg/ml protein were diluted 75 fold in 100 mM citric acid buffer containing 1 g/L BSA, adjusted to pH 5.0 using 4 N NaOH. 100 microliter of these diluted samples was transferred to a 96 wells PCR plate and was exposed to a 30 minutes incubation at 79.3° C., followed by immediate cooling to 4° C. in a PCR thermocycler. Temperature treated samples were then further diluted 100 fold in 100 mM citric acid buffer containing 1 g/L BSA, adjusted to pH 5.0 using 4 N NaOH. Residual activity was determined as under Assay 2A.

Assay 2D Activity at pH4:Activity to pH5 Ratio

As under Assay 2A, except that the samples were diluted in 100 mM citric acid buffer containing 1 g/L BSA, adjusted to pH 4.0 using 4 N NaOH.

Assay 2E Thermostability at pH 4

Samples of approximately 0.4-4 mg/ml protein were diluted 75 fold in 100 mM citric acid buffer citric acid buffer containing 1 g/L BSA, adjusted to pH 4.0 using 4 N NaOH. 100 microliter of these diluted samples was transferred to a 96 wells PCR plate and was exposed to a 30 minutes incubation at 57.8° C., followed by immediate cooling to 4° C. in a PCR thermocycler. Temperature treated samples were then further diluted 100 fold in 100 mM citric acid buffer containing 1 g/L BSA, adjusted to pH 5.0 using 4 N NaOH. Residual activity was determined as under Assay 2A.

Assay 2F Thermostability in the Presence of Sucrose

Samples of approximately 0.4-4 mg/ml protein were diluted 75 fold in 100 mM citric acid buffer containing 1 g/L BSA, adjusted to pH 5.0 using 4 N NaOH, with 2.5% sucrose added. 100 microliter of these diluted samples was transferred to a 96 wells PCR plate and is exposed to a 30 minutes incubation at 79.3° C., followed by immediate cooling to 4° C. in a PCR thermocycler. Temperature treated samples were then further diluted 100 fold in 100 mM citric acid buffer containing 1 g/L BSA, adjusted to pH 5.0 using 4 N NaOH. Residual activity was determined as under A).

Determination of Altered Properties.

Altered properties of alpha-amylase variants according to the invention as compared with a reference polypeptide having an amino acid sequence as set out in SEQ ID NO: 2 were obtained as follows.

Firstly, the properties of the variants and the reference polypeptide were measured as described under Assay 2A to Assay 2F above.

Secondly, from these measurements the percentages (%) listed in tables 4-8 below were obtained. The way to obtain the percentages listed in the tables below is explained via an exemplary determination and calculation of sucrose tolerance of variant #. The % for the properties Thermostability at pH 5 (Assay 2C), Activity at pH4:Activity to PH5 ratio (Assay 2D), Thermostability at pH 4 (Assay 2E) and Thermostability in the presence of sucrose (Assay 2F) were obtained analogously.

The values listed in the tables 4-8 below are an average of 2 measurements on the same sample.

Exemplary Determination and Calculation of Sucrose Tolerance of Variant #

The activity of variant # was determined in the presence of sucrose (measured as described under Assay 2B) and expressed as a ratio to the activity measured for the same variant in the absence of sucrose (measured as described under Assay 2A above).

The reference polypeptide (the alpha amylase having an amino acid sequence as set out in SEQ ID NO: 2) was subjected to the same experimental conditions.

If the activity of variant # would be 850 units/ml in presence of sucrose (Assay 2B), and 1000 units/ml in absence of sucrose (Assay 2A), the ratio of the activity in presence of sucrose to the activity in absence of sucrose for variant # would be 0.85.

If the activity of the reference polypeptide would be 600 units/ml in presence of sucrose (Assay 2B), and 1000 units/ml in absence of sucrose (Assay 2A), then the ratio of the activity in presence of sucrose to the activity in absence of sucrose for the reference polypeptide would be 0.60.

This value of the reference polypeptide is then normalized to 100%.

In this exemplary calculation the sucrose tolerance of variant # compared with the reference polypeptide would then be (0.85/0.60)×100%=142%. 142% (for variant #) is an increase compared with 100% (for the reference polypeptide), as a result variant # is said to have an increased sucrose tolerance compared with the reference polypeptide.

In short table 4 lists: the ratio of

[Activity of variant # in Assay 2B]:[Activity of variant # in Assay 2A], expressed as a percentage of the ratio of

[Activity of reference polypeptide in Assay 2B]:[Activity of reference polypeptide in Assay 2A].

The percentage thus obtained is the sucrose tolerance as listed in table 4.

Strains and Plasmids

*Bacillus subtilis* strain BS154 (CBS 363.94) (ΔaprE, ΔnprE, amyE-, spo-) is described in Quax and Broekhuizen 1994 Appl Microbiol Biotechnol. 41: 425-431.

The *E. coli/B. subtilis* shuttle vector pBHA12 is described in (WO2008/000632). *Alicyclobacillus pohliae* NCIMB14276 is described by Imperio et al (Int. J. Syst. Evol. Microbiol 58:221-225, 2008).

Molecular Biology Techniques

Molecular biology techniques known to the skilled person are performed according to (Sambrook & Russell, Molecular Cloning: A Laboratory Manual, 3rd Ed., CSHL Press, Cold Spring Harbor, N. Y., 2001). Polymerase chain reaction (PCR) is performed on a thermocycler with Phusion High-Fidelity DNA polymerase (Finnzymes OY, Aspoo, Finland) according to the instructions of the manufacturer.

Example 1

DNA Constructs and Transformation

The *E. coli/B. subtilis* shuttle vector pBHA12 is described in (WO2008/000632). This vector is modified by introducing a PmeI restriction site and the amyQ terminator from *Bacillus amyloliquefaciens*. The pBHA12 vector is digested with SphI and HindIII and a synthetic DNA fragment (SEQ ID NO: 3) containing the PmeI restriction site, the amyQ terminator and the SphI and HindIII restriction sites is inserted. This modification results in vector pGBB09 and this vector is used for the expression of the alpha-amylase variants (FIG. 1).

```
                                            (SEQ ID NO: 3)
5'-GCATGCGTTTAAACAAAAACACCTCCAAGCTGAGTGCGGGTATCAGC

CTTGGAGGTGCGTTTATTTTTTCAGCCGTATGACAAGGTCGGCATCAGAA

GCTT-3'
```

Amino acid changes that are introduced in the 173 alpha-amylase variants are depicted in Table 3. Positions of the amino acid change are indicated in comparison with SEQ ID NO: 2 (an example of a reference polypeptide having alpha-amylase activity).

TABLE 3

Amino acid changes to be introduced in the parent polypeptide, wherein the parent polypeptide has an amino acid sequence as set out in SEQ ID NO: 2. Amino acids are depicted according to the single letter annotation

| Variant# | Amino acid change*) |
|---|---|
| 01 | V6F |
| 2 | I14V |
| 3 | I15F |
| 4 | I15V |
| 5 | I16T |
| 6 | M45L |
| 7 | W47F |
| 8 | L51W |
| 9 | V54L |
| 10 | V54I |
| 11 | L61F |
| 12 | I69L |
| 13 | L71I |
| 14 | P73Q |
| 15 | V74P |
| 16 | L75V |
| 17 | L75F |
| 18 | L78I |
| 19 | L78V |
| 20 | T80A |
| 21 | T87V |
| 22 | G88A |
| 23 | G88S |
| 24 | T94A |
| 25 | T94P |
| 26 | R95K |
| 27 | I100T |
| 28 | H103Y |
| 29 | F104Y |
| 30 | V124I |

TABLE 3-continued

Amino acid changes to be introduced in the parent polypeptide, wherein the parent polypeptide has an amino acid sequence as set out in SEQ ID NO: 2. Amino acids are depicted according to the single letter annotation

| Variant# | Amino acid change*) |
|---|---|
| 31 | I125V |
| 32 | V126I |
| 33 | V129A |
| 34 | V129T |
| 35 | P130V |
| 36 | S133T |
| 37 | T134S |
| 38 | F136A |
| 39 | F143Y |
| 40 | G146N |
| 41 | F168Y |
| 42 | I174L |
| 43 | I174V |
| 44 | W177F |
| 45 | D178N |
| 46 | A183S |
| 47 | K186R |
| 48 | K186Q |
| 49 | F188I |
| 50 | T189Y |
| 51 | D190N |
| 52 | F194Y |
| 53 | S195T |
| 54 | S195A |
| 55 | S195N |
| 56 | L199F |
| 57 | S200N |
| 58 | Q201H |
| 59 | L210F |
| 60 | A214I |
| 61 | L217Y |
| 62 | L217W |
| 63 | A219D |
| 64 | A222V |
| 65 | A222I |
| 66 | I227V |
| 67 | F233Y |
| 68 | F233M |
| 69 | N234P |
| 70 | S235L |
| 71 | I251V |
| 72 | V254F |
| 73 | Y258F |
| 74 | G259L |
| 75 | D260G |
| 76 | P262S |
| 77 | G263A |
| 78 | A264S |
| 79 | N266S |
| 80 | H267N |
| 81 | E269D |
| 82 | V271T |
| 83 | V271I |
| 84 | Y273F |
| 85 | V279M |
| 86 | V281L |
| 87 | L286F |
| 88 | T288S |
| 89 | T288N |
| 90 | T288Q |
| 91 | T323N |
| 92 | I325F |
| 93 | N327S |
| 94 | H328Q |
| 95 | S331D |
| 96 | I350T |
| 97 | T356V |
| 98 | S358A |
| 99 | M367L |
| 100 | G370N |
| 101 | N371G |
| 102 | Y374 D |
| 103 | G377A |
| 104 | M378K |

TABLE 3-continued

Amino acid changes to be introduced in the parent polypeptide, wherein the parent polypeptide has an amino acid sequence as set out in SEQ ID NO: 2. Amino acids are depicted according to the single letter annotation

| Variant# | Amino acid change*) |
|---|---|
| 105 | W414Y |
| 106 | I421V |
| 107 | Y422 F |
| 108 | I445V |
| 109 | T603S |
| 110 | T603V |
| 111 | Y637F |
| 112 | Y6371 |
| 113 | Q648E |
| 114 | T450S |
| 115 | F652I |
| 116 | I660V |
| 117 | Q13E |
| 118 | Y20L |
| 119 | Y20V |
| 120 | T68A |
| 121 | T68S |
| 122 | T68G |
| 123 | W70Y |
| 124 | S72T |
| 125 | A117V |
| 126 | A117C |
| 127 | F128Y |
| 128 | F128I |
| 129 | F128L |
| 130 | L225I |
| 131 | L225 F |
| 132 | L225W |
| 133 | F252Y |
| 134 | F252L |
| 135 | L282W |
| 136 | L282F |
| 137 | L282I |
| 138 | L282M |
| 139 | L282T |
| 140 | Q299S |
| 141 | L334K |
| 142 | L334Y |
| 143 | L334Q |
| 144 | L334H |
| 145 | L282M |
| 146 | D283N |
| 147 | D283S |
| 148 | F284Y |
| 149 | F284I |
| 150 | F284M |
| 151 | F284W |
| 152 | F284L |
| 153 | I322V |
| 154 | I322F |
| 155 | I322P |
| 156 | A388L |
| 157 | A388S |
| 158 | E391V |
| 159 | D261G |
| 160 | A4C-A505C |
| 161 | N77C-G88C |
| 162 | L78C-T134C |
| 163 | A82C-A144C |
| 164 | A207C-A676C |
| 165 | A207C-T677C |
| 166 | S240C-S583C |
| 167 | S488C-G467C |
| 168 | A536C-V548C |
| 169 | S583C-G236C |
| 170 | V588C-F651C |
| 171 | T677C-G204C |
| 172 | S133L |
| 173 | A554G |

*)meaning of -: A4C-A505C means 2 changes: both the amino acid at position 4 and the amino acid at position 505 are changed to a C, i.e. A4 is changed to 4C and A505 changed to 505C; N77C-G88C means that both N77 and G88 are changed to a C amino acid, etc. In other words A4C-A505C means both the amino acid at position 4 and the amino acid at position 505 are changed to a C, i.e. Alanine at position 4 is changed to Cysteine and Alanine at 505 changed to Cysteine at 505, etc.

Synthetic DNA constructs containing the nucleic acid sequence encoding the alpha-amylase variants also contain a ribosome binding site and PacI restriction site at the 5' end, as shown in SEQ ID NO: 4.

```
                                    (SEQ ID NO: 4)
5'-TTAATTAAAAAAGGAGCGATTTACAT-3'
``` and a double stop codon and PmeI restriction site at the 3'end as shown in SEQ ID NO: 5

```
                                    (SEQ ID NO: 5)
5'-TAATAAGTTTAAAC-3'.
```

Figure 2:
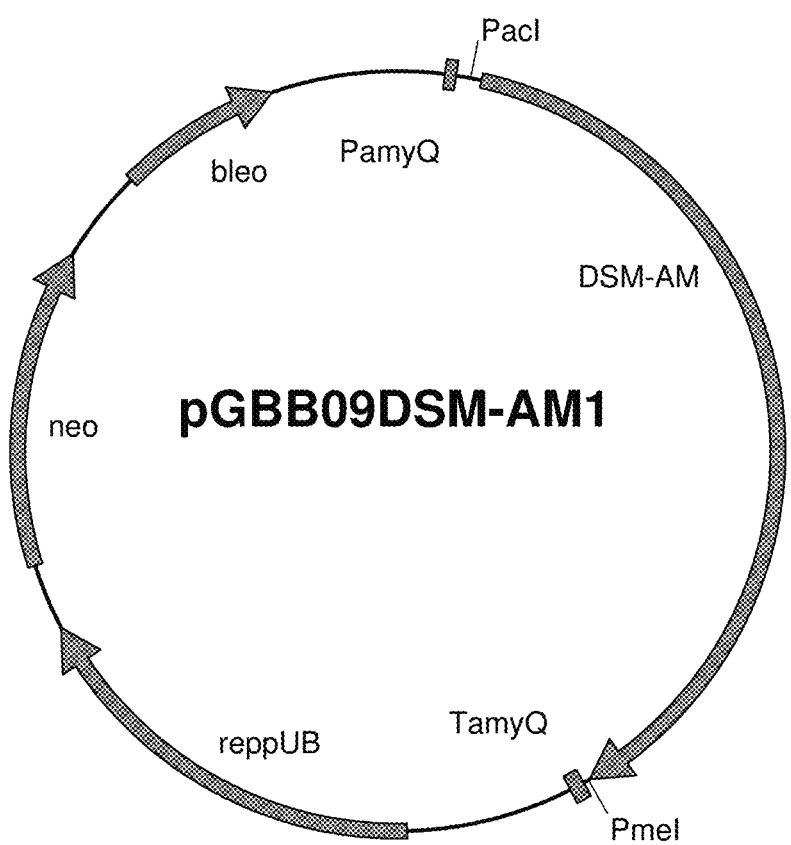
FIG. 2. Sets out the plasmid map of pGBB09DSM-AM1 containing the DSM-AM gene that is used for the production of a reference alpha-amylase.

As an example, a synthetic DNA construct existing of a PacI site, ribosome binding site, wild type DSM-AM sequence as set out in SEQ ID NO: 1, double stop codon and PmeI restriction site is listed as SEQ ID NO: 6. All nucleic acid sequence encoding the alpha-amylase variants are designed in a similar fashion and cloned as PacI, PmeI fragments in vector pGBB09. For instance the pGBB09 vector containing the wild type DSM-AM sequence as set out in SEQ ID NO: 1 was named pGB09DSM-AM1 (FIG. 2). These vectors are transformed to B. subtilis strain BS154. The sequence of the plasmid is confirmed by DNA sequencing. The B. subtilis BS154 strains containing these vectors and the strain producing the reference polypeptide is named DSM-AMB154-1 and the strains expressing the DSM-AM variants are named DSM-AMB154-01 until DSM-AMB154-170.

Example 2

Expression of Alpha-Amylase Variants, Also Referred to as DSM-AM Variants in Shake Flasks The *Bacillus subtilis* strains harboring the DSM-AM gene variants are placed on 2*TY agar plates and grown for 24 hours at 37° C. A pre-culture of 20 ml 2*TY medium composed of 1.6% (w/v) Bacto tryptone, 1% (w/v) Yeast extract and 0.5% (w/v) NaCl in 100 ml Erlenmeyer flasks are inoculated with the *B. subtilis* cells taken from the plates. The cultures are shaken vigorously at 3TC and 250 rpm for 16 hours and 0.2 ml culture medium is used to inoculate 20 ml SMM medium. SMM pre-medium contains 1.25% (w/w) yeast extract, 0.05% (w/w) $CaCl_2$, 0.075% (w/w) $MgCl_2.6H_2O$, 15 µg/l $MnSO_4$ $0.4H_2O$, 10 µg/l $CoCl_2.6H_2O$, 0.05% (w/w) citric acid, 0.025% (w/w) antifoam 86/013 (Basildon Chemicals, Abingdon, UK). To complete SMM medium, 20 ml of 5% (w/v) maltose and 20 ml of a 200 mM Na-phosphate buffer stock solution (pH 6.8), both prepared and sterilized separately, are added to 60 ml SMM pre-medium. These cultures are incubated for 48 hours at 37° C. and 250 rpm. The supernatants are harvested and analysed for enzyme productivity. The alpha-amylase activity of the alpha-amylase variants is measured according to the NBAU Assay as described in above.

SEQ ID NO 6: sets out the polynucleotide sequence of a synthetic DNA construct exciting of a PacI site, ribosome binding site, wild type DSM-AM sequence as set out in SEQ ID NO: 1, double stop codon and PmeI restriction site.

```
5'-TTAATTAAAAAAGGAGCGATTTACATATGAAAAAGAAAACGCTTTCA
TTATTTGTGGGACTGATGCTGCTCCTCGGTCTTCTGTTCAGCGGTTCTCT
TCCGTACAATCCAAACGCCGCTGAAGCCAGCAGTTCCGCAAGCGTCAAAG
GGGACGTGATTTACCAGATTATCATTGACCGGTTTTACGATGGGGACACG
ACGAACAACAATCCTGCCAAAAGTTATGGACTTTACGATCCCACCAAATC
GAAGTGGAAAATGTATTGGGCGGGGATCTGGAGGGGGTTCGTCAAAAAC
TTCCTTATCTTAAACAGCTGGGCGTAACGACGATCTGGTTGTCCCCGGTT
TTGGACAATCTGGATACACTTGCAGGTACCGATAACACTGGCTATCACGG
ATACTGGACGCGCGATTTTAAACAGATTGAGGAACATTTCGGGAATTGGA
CCACATTTGACACGTTGGTCAATGATGCTCACCAAAACGAATCAAGGTG
ATTGTCGACTTTGTGCCCAATCATTCAACTCCTTTTAAGGCAAACGATTC
CACCTTTGCGGAAGGCGGCGCCCTCTACGACAACGGAACCTATATGGGCA
ATTATTTTGATGACGCAACAAAAGGGTACTTTCACCATAATGGGGACATC
AGCAACTGGGACGACCGGTACGAGGCGCAATGGAAAAACTTCACGGATCC
AGCCGGTTTCTCGCTTGCCGATTTGTCGCAGGAAAATGGCACGATTGCTC
AATACCTGACCGATGCGGCGGTTCAATTAGTAGCACATGGAGCGGATGGT
TTGCGGATTGATGCGGTGAAGCATTTTAATTCTGGGTTCTCCAAATCGTT
GGCTGATAAACTGTACCAAAAGAAAGACATTTTCCTAGTGGGGAATGGT
ACGGAGATGACCCCGGAGCAGCCAATCATTTGGAAAAGGTCCGGTACGCC
AACAACAGCGGTGTCAATGTGCTGGATTTTGATCTCAACACGGTGATTCG
AAATGTGTTCGGTACATTTACGCAAACGATGTACGATCTTAACAATATGG
TGAACCAAACGGGGAACGAGTACAAATACAAAGAAAATCTAATCACATTT
ATCGATAACCATGATATGTCGAGATTTCTTACGGTAAATTCGAACAAGGC
GAATTTGCACCAGGCGCTTGCTTTCATTCTCACTTCGCGGGGAACGCCCT
CCATCTATTACGGAACCGAACAATACATGGCAGGCGGCAATGACCCGTAC
AACAGGGGGATGATGCCGGCGTTTGATACGACAACCACCGCCTTTAAAGA
GGTGTCAACTCTGGCGGGGTTGCGCAGGAACAATGCAGCGATCCAGTACG
GCACCACCACCCAACGTTGGATCAACAATGATGTTTACATTTATGAGCGG
AAATTTTTCAACGATGTCGTATTGGTGGCCATCAATCGAAACACGCAATC
CTCCTACTCGATTTCCGGTTTGCAGACTGCCTTGCCAAATGGCAACTATG
CGGATTATCTGTCAGGGCTGTTGGGGGGGAACGGGATTTCCGTTTCCAAT
GGAAGTGTCGCTTCGTTCACGCTTGCGCCTGGAGCCGTGTCTGTTTGGCA
GTACAGCACATCCGCTTCAGCGCCGCAAATCGGATCGGTTGCTCCGAATA
TGGGAATTCCGGGTAATGTGGTCACGATCGACGGGAAAGGTTTTGGAACG
ACGCAGGGAACCGTGACATTTGGCGGAGTGACAGCGACTGTAAAATCCTG
GACATCAAACCGGATTGAAGTGTACGTGCCCAACATGGCCGCCGGTCTGA
```

CCGATGTAAAAGTCACCGCGGGTGGAGTTTCCAGCAATCTGTATTCTTAC

AATATTTTGAGTGGAACGCAGACATCGGTTGTGTTTACTGTGAAAAGTGC

TCCTCCGACCAACCTGGGGGATAAGATTTACCTGACGGGCAACATACCGG

AATTGGGAAATTGGAGCACGGATACGAGCGGAGCCGTTAACAATGCGCAA

GGGCCCCTGCTCGCGCCCAATTATCCGGATTGGTTTTATGTATTCAGCGT

TCCGGCAGGAAAGACGATTCAATTCAAGTTTTTCATCAAGCGTGCGGATG

GAACGATTCAATGGGAGAATGGTTCGAACCACGTGGCCACAACTCCCACG

GGTGCAACCGGTAACATCACTGTCACGTGGCAAAACTAATAAGTTTAAA

C-3'

SEQ ID NO: 2 sets out the amino acid sequence of the mature *Alicyclobacillus pohliae* NCIMB14276 wild type alpha-amylase polypeptide without the first 33 amino acids encoding the signal peptide.

```
SSSASVKGDVIYQIIIDRFYDGDTTNNNPAKSYGLYDPTKSKWKMYWGGD
LEGVRQKLPYLKQLGVTTIWLSPVLDNLDTLAGTDNTGYHGYWTRDFKQI
EEHFGNWTTFDTLVNDAHQNGIKVIVDFVPNHSTPFKANDSTFAEGGALY
DNGTYMGNYFDDATKGYFHHNGDISNWDDRYEAQWKNFTDPAGFSLADLS
QENGTIAQYLTDAAVQLVAHGADGLRIDAVKHFNSGFSKSLADKLYQKKD
IFLVGEWYGDDPGAANHLEKVRYANNSGVNVLDFDLNTVIRNVFGTFTQT
MYDLNNMVNQTGNEYKYKENLITFIDNHDMSRFLTVNSNKANLHQALAFI
LTSRGTPSIYYGTEQYMAGGNDPYNRGMMPAFDTTTTAFKEVSTLAGLRR
NNAAIQYGTTTQRWINNDVYIYERKFFNDVVLVAINRNTQSSYSISGLQT
ALPNGNYADYLSGLLGGNGISVSNGSVASFTLAPGAVSVWQYSTSASAPQ
IGSVAPNMGIPGNVVTIDGKGFGTTQGTVTFGGVTATVKSWTSNRIEVYV
PNMAAGLTDVKVTAGGVSSNLYSYNILSGTQTSVVFTVKSAPPTNLGDKI
YLTGNIPELGNWSTDTSGAVNNAQGPLLAPNYPDWFYVFSVPAGKTIQFK
FFIKRADGTIQWENGSNHVATTPTGATGNITVTANQN
```

Example 3 Sucrose Tolerance of Variants According to the Invention

Sucrose tolerance of variants according to the invention having an amino acid sequence according to SEQ ID NO: 2 including an amino acid change as indicated in table 4 below and of the reference alpha amylase polypeptide having an amino acid sequence as set out in SEQ ID NO: 2 was determined as described herein under Materials and Methods above (Assay 2A, Assay 2B and "Exemplary determination and calculation of sucrose tolerance of variant #").

TABLE 4

Sucrose tolerance of variants according to the invention compared to the reference polypeptide. The sucrose tolerance of the reference polypeptide (polypeptide having an amino acid sequence as set out in SEQ ID NO: 2), was set at 100%. A sucrose tolerance of more than 100% shows that the variant has an increased sucrose tolerance compared to the reference polypeptide.

| Variant # | Amino Acid Change*) | Sucrose tolerance of variant compared with sucrose tolerance of reference polypeptide (set at 100%) (average of 2 measurements) |
|---|---|---|
| 4 | I15V | 118% |
| 5 | I16T | 111% |
| 6 | M45L | 118% |
| 16 | L75V | 113% |
| 24 | T94A | 131% |
| 25 | T94P | 136% |
| 33 | V129A | 166% |
| 37 | T134S | 110% |
| 42 | I174L | 113% |
| 44 | W177F | 128% |
| 45 | D178N | 115% |
| 48 | K186Q | 113% |
| 52 | F194Y | 154% |
| 59 | L210F | 110% |
| 69 | N234P | 121% |
| 72 | V254F | 131% |
| 86 | V281L | 124% |
| 91 | T323N | 107% |
| 92 | I325F | 120% |
| 98 | S358A | 112% |
| 101 | N371G | 120% |
| 115 | F652I | 114% |
| 117 | Q13E | 113% |
| 123 | W70Y | 118% |
| 124 | S72T | 137% |
| 136 | L282F | 127% |
| 138 | L282M | 113% |
| 139 | L282T | 115% |
| 146 | D283N | 119% |
| 147 | D283S | 116% |
| 151 | F284W | 116% |
| 159 | D261G | 116% |
| 161 | N77C-G88C | 123% |
| 162 | L78C-T134C | 109% |
| 172 | S133L | 109% |

*)meaning of -: A4C-A505C means 2 changes: both the amino acid at position 4 and the amino acid at position 505 are changed to a C, i.e. Alanine at position 4 is changed to Cysteine at position 4 and Alanine at position 505 changed to Cysteine at position 505; N77C-G88C means that both N77 and G88 are changed to a Cysteine amino acid, etc.

Example 4 Thermostability at pH 5 of Variants According to the Invention

Thermostability at pH 5 of variants according to the invention having an amino acid sequence according to SEQ ID NO: 2 including an amino acid change as indicated in table 5 below and of the reference polypeptide having an amino acid sequence as set out in SEQ ID NO: 2 was determined as described herein under Materials and Methods above. This done using Assay 2A, Assay 2C and "Exemplary determination and calculation of sucrose tolerance of variant #" as described above, applied analogously to the ratio of

[Residual Activity of variant # in Assay 2C]:[Activity of variant # in Assay 2A], expressed as a percentage of the ratio of

[Residual Activity of reference polypeptide in Assay 2C]:[Activity of reference polypeptide in Assay 2A].

The percentage thus obtained is the themostability at pH 5 as listed in table 5.

TABLE 5

Thermostability at pH 5 of variants according to the invention compared to the reference polypeptide. The Thermostability at pH 5 of the reference polypeptide (polypeptide having an amino acid sequence as set out in SEQ ID NO: 2), was set at 100%. An Thermostability at pH 5 of more than 100% shows that the variant has an increased Thermostability at pH 5 compared to the reference polypeptide.

| Variant # | Amino Acid Change | Thermostability at pH 5 of variant compared with reference polypeptide (set at 100%) (average of 2 measurements) |
|---|---|---|
| 11 | L61F | 161% |
| 17 | L75F | 138% |
| 22 | G88A | 138% |
| 36 | S133T | 157% |
| 41 | F168Y | 129% |
| 49 | F188I | 318% |
| 57 | S200N | 233% |
| 64 | A222V | 125% |
| 72 | V254F | 162% |
| 78 | A264S | 136% |
| 86 | V281L | 165% |
| 93 | N327S | 139% |
| 117 | Q13E | 138% |
| 123 | W70Y | 169% |
| 128 | F128I | 122% |
| 136 | L282F | 164% |
| 138 | L282M | 134% |
| 156 | A388L | 121% |
| 159 | D261G | 130% |

Example 5 Activity at pH4:Activity at pH5 Ratio of Variants According to the Invention Activity at pH4:Activity at pH5 ratio of variants according to the invention having an amino acid sequence according to SEQ ID NO: 2 including an amino acid change as indicated in table 4 below and of the reference polypeptide having an amino acid sequence as set out in SEQ ID NO: 2 was determined as described herein under Materials and Methods above. This was done using Assay 2A, Assay 2D and "Exemplary determination and calculation of sucrose tolerance of variant #" as described above, applied analogously to the ratio of

[Activity of variant # in Assay 2D]:[Activity of variant # in Assay 2A], expressed as a percentage of the ratio of

[Activity of reference polypeptide in Assay 2D]:[Activity of reference polypeptide in Assay 2A].

The percentage thus obtained is the Activity at pH4:Activity at pH5 ratio as listed in table 6.

TABLE 6

Activity at pH 4:Activity at pH 5 ratio of variants according to the invention compared to the reference polypeptide. The Activity at pH 4:Activity at pH 5 ratio of the reference polypeptide (polypeptide having an amino acid sequence as set out in SEQ ID NO: 2), was set at 100%. An Activity at pH 4:Activity at pH 5 ratio of more than 100% shows that the variant has an increased Activity at pH 4:Activity at pH 5 ratio compared to the reference polypeptide.

| Variant # | Amino Acid Change | Activity at pH 4:Activity at pH 5 ratio of variant compared with reference polypeptide (set at 100%) (average of 2 measurements) |
|---|---|---|
| 30 | V124I | 118% |
| 32 | V126I | 128% |
| 33 | V129A | 144% |

TABLE 6-continued

Activity at pH 4:Activity at pH 5 ratio of variants according to the invention compared to the reference polypeptide. The Activity at pH 4: Activity at pH 5 ratio of the reference polypeptide (polypeptide having an amino acid sequence as set out in SEQ ID NO: 2), was set at 100%. An Activity at pH 4:Activity at pH 5 ratio of more than 100% shows that the variant has an increased Activity at pH 4:Activity at pH 5 ratio compared to the reference polypeptide.

| Variant # | Amino Acid Change | Activity at pH 4:Activity at pH 5 ratio of variant compared with reference polypeptide (set at 100%) (average of 2 measurements) |
|---|---|---|
| 38 | F136A | 119% |
| 41 | F168Y | 112% |
| 48 | K186Q | 110% |
| 54 | S195A | 115% |
| 56 | L199F | 126% |
| 63 | A219D | 114% |
| 64 | A222V | 119% |
| 65 | A222I | 126% |
| 80 | H267N | 110% |
| 81 | E269D | 109% |
| 82 | V271T | 118% |
| 88 | T288S | 110% |
| 89 | T288N | 115% |
| 92 | I325F | 120% |
| 95 | S331D | 116% |
| 100 | G370N | 120% |
| 103 | G377A | 107% |
| 106 | I421V | 111% |
| 114 | T450S | 107% |
| 115 | F652I | 107% |
| 118 | Y2OL | 110% |
| 119 | Y20V | 110% |
| 120 | T68A | 113% |
| 122 | T68G | 111% |
| 124 | S72T | 121% |
| 131 | L225F | 148% |
| 137 | L282I | 117% |
| 138 | L282M | 117% |
| 144 | L334H | 106% |

Example 6 Thermostability at pH 4 of Variants According to the Invention

Thermostability at pH 4 of variants according to the invention having an amino acid sequence according to SEQ ID NO: 2 including an amino acid change as indicated in table 7 below and of the parent polypeptide having an amino acid sequence as set out in SEQ ID NO: 2 was determined as described herein under Materials and Methods above. This was done using Assay 2A, Assay 2E and "Exemplary determination and calculation of sucrose tolerance of variant #" as described above, applied analogously to the ratio of

[Residual Activity of variant # in Assay 2E]:[Activity of variant # in Assay 2A], expressed as a percentage of the ratio of

[Residual Activity of reference polypeptide in Assay 2E]:[Activity of reference polypeptide in Assay 2A].

The percentage thus obtained is the Thermostability at pH 4 as listed in table 7.

TABLE 7

Thermostability at pH 4 of variants according to the invention compared to the reference polypeptide. The thermostability at pH 4 of the reference polypeptide (polypeptide having an amino acid sequence as set out in SEQ ID NO: 2), was set at 100%. A thermostability at pH 4 of more than 100% shows that the variant has an increased thermostability at pH 4 compared to the reference polypeptide.

| Variant # | Amino Acid Change | Thermostability at pH 4 of variant compared with reference polypeptide (set at 100%) (average of 2 measurements) |
|---|---|---|
| 22 | G88A | 134% |
| 49 | F188I | 254% |
| 57 | S200N | 137% |
| 64 | A222V | 120% |
| 123 | W70Y | 147% |
| 136 | L282F | 150% |
| 137 | L282I | 123% |
| 138 | L282M | 121% |
| 139 | L282T | 128% |

Example 7 Thermostability in the Presence of Sucrose of Variants According to the Invention Thermostability in the presence of sucrose of variants according to the invention having an amino acid sequence according to SEQ ID NO: 2 including an amino acid change as indicated in table 8 below and of the parent polypeptide having an amino acid sequence as set out in SEQ ID NO: 2 was determined as described herein under Materials and Methods above. This was done using Assay 2A, Assay 2F and "Exemplary determination and calculation of sucrose tolerance of variant #" as described above, applied analogously to the ratio of

[Residual Activity of variant # in Assay 2F]:[Activity of variant # in Assay 2A], expressed as a percentage of the ratio of

[Residual Activity of reference polypeptide in Assay 2F]:[Activity of reference polypeptide in Assay 2A].

The percentage thus obtained is the Thermostability in the presence of sucrose as listed in table 8.

TABLE 8

Thermostability in the presence of sucrose of variants according to the invention compared to the reference polypeptide. The thermostability in the presence of sucrose of the reference polypeptide (polypeptide having an amino acid sequence as set out in SEQ ID NO: 2), was set at 100%. A thermostability in the presence of sucrose of more than 100% shows that the variant has an increased thermostability in the presence of sucrose compared to the reference polypeptide.

| Variant # | Amino Acid Change | Thermostability in the presence of sucrose of variant compared with reference polypeptide (set at 100%) (average of 2 measurements) |
|---|---|---|
| 11 | L61F | 118% |
| 17 | L75F | 131% |
| 36 | S133T | 122% |
| 41 | F168Y | 120% |
| 49 | F188I | 212% |
| 57 | S200N | 157% |
| 72 | V254F | 149% |
| 78 | A264S | 131% |
| 86 | V281L | 142% |
| 93 | N327S | 136% |
| 101 | N371G | 110% |
| 120 | T68A | 116% |
| 123 | W70Y | 161% |
| 136 | L282 F | 143% |

TABLE 8-continued

Thermostability in the presence of sucrose of variants according to the invention compared to the reference polypeptide. The thermostability in the presence of sucrose of the reference polypeptide (polypeptide having an amino acid sequence as set out in SEQ ID NO: 2), was set at 100%. A thermostability in the presence of sucrose of more than 100% shows that the variant has an increased thermostability in the presence of sucrose compared to the reference polypeptide.

| Variant # | Amino Acid Change | Thermostability in the presence of sucrose of variant compared with reference polypeptide (set at 100%) (average of 2 measurements) |
|---|---|---|
| 137 | L282I | 131% |
| 138 | L282M | 149% |
| 139 | L282T | 137% |
| 156 | A388L | 120% |
| 159 | D261G | 123% |

The invention claimed is:

1. A variant polypeptide having alpha-amylase activity, wherein the variant has an amino acid sequence which, when aligned with the alpha-amylase comprising the sequence set out in SEQ ID NO: 2, comprises at least one substitution of an amino acid residue corresponding to any of amino acids 16, 45, 72, 77, 94, 134, 174, 177, 178, 186, 210, 234, 283, 284, 323, 325, 652, said positions being defined with reference to SEQ ID NO: 2 wherein the alpha-amylase polypeptide variant is at least 90% identical to SEQ ID NO: 2, and wherein the variant has one or more altered properties as compared with a reference polypeptide having alpha-amylase activity, wherein the at least one altered property is an increased sucrose tolerance.

2. A variant polypeptide according to claim 1, wherein the reference polypeptide is the alpha-amylase of SEQ ID NO: 2.

3. A variant polypeptide according to claim 1, wherein the variant demonstrates any one of
   a) increased (thermo)stability; or
   b) increased specific activity; or
   c) increased stability/activity at different pH range; or
   d) change in product spectrum (defined as ratio of one product over another); or
   e) increased activity on raw starch; or
   f) altered temperature optimum; or
   g) alter substrate specificity; or
   h) increased productivity in the production of the alpha-amylase variant;
as compared with a reference polypeptide having alpha-amylase activity; or
wherein the variant demonstrates any one of
   i) a pH optimum in a range of from 5 to 8; or
   j) an alkaline pH at which 50% of the activity is observed as compared to the alpha-amylase at the pH optimum which is set at 100%, which is at least 6.9.

4. A nucleic acid sequence encoding a variant polypeptide according to claim 1.

5. A nucleic acid construct comprising the nucleic acid sequence of claim 4 operably linked to one or more control sequences capable of directing the expression of an alpha-amylase in a suitable expression host.

6. A recombinant expression vector comprising the nucleic acid construct of claim 5.

7. A recombinant host cell comprising the expression vector of claim 6.

8. A method for producing an alpha-amylase comprising cultivating the host cell of claim 7 under conditions conducive to production of the alpha-amylase and recovering the alpha-amylase.

9. A method of producing an alpha-amylase polypeptide variant, which method comprises:
   a) selecting a polypeptide having alpha-amylase activity;
   b) substituting at least one amino acid residue corresponding to any of
      16, 45, 72, 77, 94, 134, 174, 177, 178, 186, 210, 234, 283, 284, 323, 325, 652,
      said positions being defined with reference to SEQ ID NO: 2;
   c) optionally substituting one or more further amino acids as defined in b);
   d) preparing the variant resulting from steps a)-c);
   e) determining a property of the variant; and
   f) selecting a variant having an altered property in comparison a reference polypeptide having alpha-amylase activity, wherein the altered property is increased sucrose tolerance, thereby to produce an alpha-amylase polypeptide variant, wherein the alpha-amylase polypeptide variant is at least 90% identical to SEQ ID NO: 2.

10. A composition comprising the variant polypeptide according to claim 1 and one or more components selected from the group consisting of milk powder, gluten, granulated fat, an additional enzyme, an amino acid, a salt, oxidants, reducing agents, emulsifiers, sodium stearoyl lactylate, calcium stearoyl lactylate, polyglycerol esters of fatty acids and diacetyl tartaric acid esters of mono- and diglycerides, gums, flavours, acids, starch, modified starch, gluten, humectants and preservatives.

11. A pre-mix comprising flour and the variant polypeptide according to claim 1 and at least one additional enzyme.

12. A variant polypeptide according to claim 1 capable of being used in the preparation of a dough and/or a baked product.

13. A dough comprising a variant polypeptide according to claim 1.

14. A process for the production of a baked product, which method comprises baking the dough according to claim 13.

15. A baked product obtainable by the process according to claim 14.

16. A baked product prepared using a variant polypeptide of claim 1.

17. A variant polypeptide according to claim 1, wherein the variant is at least 95% identical to SEQ ID NO: 2, and wherein the variant comprises at least one substitution of an amino acid residue corresponding to any of amino acid positions 16, 45, 72, 77, 94, 134, 174, 177, 178, 186, 210, 234, 283, 284, 323, 325, and 652.

18. A variant polypeptide according to claim 1, wherein the variant consists of SEQ ID NO: 2 with at least one substitution of an amino acid residue selected from amino acid positions 16, 45, 72, 77, 94, 134, 174, 177, 178, 186, 210, 234, 283, 284, 323, 325 and 652.

* * * * *

SEQUENCE LISTING

```
<160> NUMBER OF SEQ ID NOS: 8

<210> SEQ ID NO 1
<211> LENGTH: 2160
<212> TYPE: DNA
<213> ORGANISM: Alicyclobacillus pohliae

<400> SEQUENCE: 1
atgaaaaaga aaacgctttc attatttgtg ggactgatgc tgctcctcgg tcttctgttc      60
agcggttctc ttccgtacaa tccaaacgcc gctgaagcca gcagttccgc aagcgtcaaa     120
ggggacgtga tttaccagat tatcattgac cggttttacg atggggacac gacgaacaac     180
aatcctgcca aaagttatgg actttacgat cccaccaaat cgaagtggaa aatgtattgg     240
ggcggggatc tggagggggt tcgtcaaaaa cttccttatc ttaaacagct gggcgtaacg     300
acgatctggt tgtccccggt tttggacaat ctggatacac ttgcaggtac cgataacact     360
ggctatcacg gatactggac gcgcgatttt aaacagattg aggaacattt cgggaattgg     420
accacatttg acacgttggt caatgatgct caccaaaacg gaatcaaggt gattgtcgac     480
tttgtgccca atcattcaac tccttttaag gcaaacgatt ccacctttgc ggaaggcggc     540
gccctctacg acaacggaac ctatatgggc aattattttg atgacgcaac aaaagggtac     600
tttcaccata tggggacat cagcaactgg gacgaccggt acgaggcgca atggaaaaac      660
ttcacggatc cagccggttt ctcgcttgcc gatttgtcgc aggaaaatgg cacgattgct     720
caatacctga ccgatgcggc ggttcaatta gtagcacatg gagcggatgg tttgcggatt     780
gatgcggtga agcattttaa ttctgggttc tccaaatcgt tggctgataa actgtaccaa     840
aagaaagaca ttttcctagt gggggaatgg tacggagatg accccggagc agccaatcat     900
ttggaaaagg tccggtacgc caacaacagc ggtgtcaatg tgctggattt tgatctcaac     960
acggtgattc gaaatgtgtt cggtacattt acgcaaacga tgtacgatct taacaatatg    1020
gtgaaccaaa cggggaacga gtacaaatac aaagaaaatc taatcacatt tatcgataac    1080
catgatatgt cgagatttct tacggtaaat tcgaacaagg cgaatttgca ccaggcgctt    1140
gctttcattc tcacttcgcg gggaacgccc tccatctatt acggaaccga acaatacatg    1200
gcaggcggca atgacccgta caacaggggg atgatgccgc gtttgatac gacaaccacc     1260 gcctttaaag aggtgtcaac tctgcgggg ttgcgcagga caatgcagc gatccagtac      1320 ggcaccacca cccaacgttg gatcaacaat gatgtttaca tttatgagcg gaaattttc     1380 aacgatgtcg tattggtggc catcaatcga aacacgcaat cctcctactc gatttccggt    1440
```

```
ttgcagactg ccttgccaaa tggcaactat gcggattatc tgtcagggct gttgggggggg    1500 aacgggatttt ccgttttccaa tggaagtgtc gcttcgttca cgcttgcgcc tggagccgtg    1560
tctgtttggc agtacagcac atccgcttca gcgccgcaaa tcggatcggt tgctccgaat    1620
atgggaattc cgggtaatgt ggtcacgatc gacgggaaag gttttggaac gacgcaggga    1680
accgtgacat ttggcggagt gacagcgact gtaaaatcct ggacatcaaa ccggattgaa    1740
gtgtacgtgc ccaacatggc cgccggtctg accgatgtaa aagtcaccgc gggtggagtt    1800
tccagcaatc tgtattctta caatattttg agtggaacgc agacatcggt tgtgtttact    1860
gtgaaaagtg ctcctccgac caacctgggg gataagattt acctgacggg caacataccg    1920
gaattgggaa attggagcac ggatacgagc ggagccgtta acaatgcgca agggcccctg    1980
ctcgcgccca attatccgga ttggttttat gtattcagcg ttccggcagg aaagacgatt    2040
caattcaagt ttttcatcaa gcgtgcggat ggaacgattc aatgggagaa tggttcgaac    2100
cacgtggcca aactcccac gggtgcaacc ggtaacatca ctgtcacgtg caaaactag    2160
```

<210> SEQ ID NO 2
<211> LENGTH: 686
<212> TYPE: PRT
<213> ORGANISM: Alicyclobacillus pohliae

<400> SEQUENCE: 2

```
Ser Ser Ser Ala Ser Val Lys Gly Asp Val Ile Tyr Gln Ile Ile
1               5                   10                  15

Asp Arg Phe Tyr Asp Gly Asp Thr Thr Asn Asn Pro Ala Lys Ser
                20                  25                  30

Tyr Gly Leu Tyr Asp Pro Thr Lys Ser Lys Trp Lys Met Tyr Trp Gly
            35                  40                  45

Gly Asp Leu Glu Gly Val Arg Gln Lys Leu Pro Tyr Leu Lys Gln Leu
50                  55                  60

Gly Val Thr Thr Ile Trp Leu Ser Pro Val Leu Asp Asn Leu Asp Thr
65                  70                  75                  80

Leu Ala Gly Thr Asp Asn Thr Gly Tyr His Gly Tyr Trp Thr Arg Asp
                85                  90                  95

Phe Lys Gln Ile Glu Glu His Phe Gly Asn Trp Thr Thr Phe Asp Thr
                100                 105                 110

Leu Val Asn Asp Ala His Gln Asn Gly Ile Lys Val Ile Val Asp Phe
            115                 120                 125

Val Pro Asn His Ser Thr Pro Phe Lys Ala Asn Asp Ser Thr Phe Ala
130                 135                 140

Glu Gly Gly Ala Leu Tyr Asp Asn Gly Thr Tyr Met Gly Asn Tyr Phe
145                 150                 155                 160

Asp Asp Ala Thr Lys Gly Tyr Phe His His Asn Gly Asp Ile Ser Asn
                165                 170                 175

Trp Asp Asp Arg Tyr Glu Ala Gln Trp Lys Asn Phe Thr Asp Pro Ala
            180                 185                 190

Gly Phe Ser Leu Ala Asp Leu Ser Gln Glu Asn Gly Thr Ile Ala Gln
        195                 200                 205

Tyr Leu Thr Asp Ala Ala Val Gln Leu Val Ala His Gly Ala Asp Gly
210                 215                 220

Leu Arg Ile Asp Ala Val Lys His Phe Asn Ser Gly Phe Ser Lys Ser
225                 230                 235                 240

Leu Ala Asp Lys Leu Tyr Gln Lys Lys Asp Ile Phe Leu Val Gly Glu
                245                 250                 255
```

```
Trp Tyr Gly Asp Asp Pro Gly Ala Ala Asn His Leu Glu Lys Val Arg
            260                 265                 270

Tyr Ala Asn Asn Ser Gly Val Asn Val Leu Asp Phe Asp Leu Asn Thr
        275                 280                 285

Val Ile Arg Asn Val Phe Gly Thr Phe Thr Gln Thr Met Tyr Asp Leu
    290                 295                 300

Asn Asn Met Val Asn Gln Thr Gly Asn Glu Tyr Lys Tyr Lys Glu Asn
305                 310                 315                 320

Leu Ile Thr Phe Ile Asp Asn His Asp Met Ser Arg Phe Leu Thr Val
                325                 330                 335

Asn Ser Asn Lys Ala Asn Leu His Gln Ala Leu Ala Phe Ile Leu Thr
            340                 345                 350

Ser Arg Gly Thr Pro Ser Ile Tyr Tyr Gly Thr Glu Gln Tyr Met Ala
        355                 360                 365

Gly Gly Asn Asp Pro Tyr Asn Arg Gly Met Met Pro Ala Phe Asp Thr
    370                 375                 380

Thr Thr Thr Ala Phe Lys Glu Val Ser Thr Leu Ala Gly Leu Arg Arg
385                 390                 395                 400

Asn Asn Ala Ala Ile Gln Tyr Gly Thr Thr Thr Gln Arg Trp Ile Asn
                405                 410                 415

Asn Asp Val Tyr Ile Tyr Glu Arg Lys Phe Phe Asn Asp Val Val Leu
            420                 425                 430

Val Ala Ile Asn Arg Asn Thr Gln Ser Ser Tyr Ser Ile Ser Gly Leu
        435                 440                 445

Gln Thr Ala Leu Pro Asn Gly Asn Tyr Ala Asp Tyr Leu Ser Gly Leu
    450                 455                 460

Leu Gly Gly Asn Gly Ile Ser Val Ser Asn Gly Ser Val Ala Ser Phe
465                 470                 475                 480

Thr Leu Ala Pro Gly Ala Val Ser Val Trp Gln Tyr Ser Thr Ser Ala
                485                 490                 495

Ser Ala Pro Gln Ile Gly Ser Val Ala Pro Asn Met Gly Ile Pro Gly
            500                 505                 510

Asn Val Val Thr Ile Asp Gly Lys Gly Phe Gly Thr Thr Gln Gly Thr
        515                 520                 525

Val Thr Phe Gly Gly Val Thr Ala Thr Val Lys Ser Trp Thr Ser Asn
    530                 535                 540

Arg Ile Glu Val Tyr Val Pro Asn Met Ala Ala Gly Leu Thr Asp Val
545                 550                 555                 560

Lys Val Thr Ala Gly Gly Val Ser Ser Asn Leu Tyr Ser Tyr Asn Ile
                565                 570                 575

Leu Ser Gly Thr Gln Thr Ser Val Val Phe Thr Val Lys Ser Ala Pro
            580                 585                 590

Pro Thr Asn Leu Gly Asp Lys Ile Tyr Leu Thr Gly Asn Ile Pro Glu
        595                 600                 605

Leu Gly Asn Trp Ser Thr Asp Thr Ser Gly Ala Val Asn Asn Ala Gln
    610                 615                 620

Gly Pro Leu Leu Ala Pro Asn Tyr Pro Asp Trp Phe Tyr Val Phe Ser
625                 630                 635                 640

Val Pro Ala Gly Lys Thr Ile Gln Phe Lys Phe Ile Lys Arg Ala
                645                 650                 655

Asp Gly Thr Ile Gln Trp Glu Asn Gly Ser Asn His Val Ala Thr Thr
            660                 665                 670
```

Pro Thr Gly Ala Thr Gly Asn Ile Thr Val Thr Trp Gln Asn
        675                 680                 685

<210> SEQ ID NO 3
<211> LENGTH: 100
<212> TYPE: DNA
<213> ORGANISM: Artificial Sequence
<220> FEATURE:
<223> OTHER INFORMATION: Synthetic DNA fragment containing PmeI
      restriction site, amyQ terminator, and SphI and HindIII
      restriction sites

<400> SEQUENCE: 3
gcatgcgttt aaacaaaaac acctccaagc tgagtgcggg tatcagcttg gaggtgcgtt      60 tatttttca gccgtatgac aaggtcggca tcagaagctt                            100

<210> SEQ ID NO 4
<211> LENGTH: 26
<212> TYPE: DNA
<213> ORGANISM: Artificial Sequence
<220> FEATURE:
<223> OTHER INFORMATION: Sets out the 5 sequence containing a ribosome
      binding site and PacI restriction site

<400> SEQUENCE: 4
ttaattaaaa aaggagcgat ttacat                                          26

<210> SEQ ID NO 5
<211> LENGTH: 14
<212> TYPE: DNA
<213> ORGANISM: Artificial Sequence
<220> FEATURE:
<223> OTHER INFORMATION: Sets out the 3 sequence containing a double
      stop codon and PmeI restriction site

<400> SEQUENCE: 5
taataagttt aaac                                                       14

<210> SEQ ID NO 6
<211> LENGTH: 2197
<212> TYPE: DNA
<213> ORGANISM: Artificial Sequence
<220> FEATURE:
<223> OTHER INFORMATION: Sets out the polynucleotide sequence from a
      synthetic DNA construct containing a PacI site, ribosome binding
      site, wild type DSM-AM sequence, double stop codon and PmeI
      restriction site

<400> SEQUENCE: 6
ttaattaaaa aaggagcgat ttacatatga aaaagaaaac gctttcatta tttgtgggac      60
tgatgctgct cctcggtctt ctgttcagcg gttctcttcc gtacaatcca acgccgctg     120 aagccagcag ttccgcaagc gtcaaagggg acgtgattta ccagattatc attgaccggt   180
tttacgatgg ggacacgacg aacaacaatc ctgccaaaag ttatggactt tacgatccca   240
ccaaatcgaa gtggaaaatg tattgggcg gggatctgga ggggttcgt caaaaacttc     300 cttatcttaa acagctgggc gtaacgacga tctggttgtc cccggttttg acaatctgg   360 atacacttgc aggtaccgat aacactggct atcacggata ctggacgcgc gatttttaaac 420 agattgagga acatttcggg aattggacca catttgacac gttggtcaat gatgctcacc   480
aaaacggaat caaggtgatt gtcgactttg tgcccaatca ttcaactcct tttaaggcaa   540
acgattccac ctttgcggaa ggcggcgccc tctacgacaa cggaacctat atgggcaatt   600 atttgatga cgcaacaaaa gggtactttc accataatgg ggacatcagc aactgggacg   660

-continued

```
accggtacga ggcgcaatgg aaaaacttca cggatccagc cggtttctcg cttgccgatt      720
tgtcgcagga aaatggcacg attgctcaat acctgaccga tgcggcggtt caattagtag      780
cacatggagc ggatggtttg cggattgatg cggtgaagca ttttaattct gggttctcca      840
aatcgttggc tgataaactg taccaaaaga aagacatttt cctagtgggg aatggtacg       900
gagatgaccc cggagcagcc aatcatttgg aaaaggtccg gtacgccaac aacagcggtg      960
tcaatgtgct ggattttgat ctcaacacgg tgattcgaaa tgtgttcggt acatttacgc     1020
aaacgatgta cgatcttaac aatatggtga accaaacggg gaacgagtac aaatacaaag     1080
aaaatctaat cacatttatc gataaccatg atatgtcgag atttcttacg gtaaattcga     1140
acaaggcgaa tttgcaccag gcgcttgctt tcattctcac ttcgcgggga acgccctcca     1200
tctattacgg aaccgaacaa tacatggcag gcggcaatga cccgtacaac aggggggatga    1260
tgccggcgtt tgatacgaca accaccgcct ttaaagaggt gtcaactctg gcggggttgc     1320
gcaggaacaa tgcagcgatc cagtacggca ccaccaccca acgttggatc aacaatgatg     1380
tttacattta tgagcggaaa tttttcaacg atgtcgtatt ggtggccatc aatcgaaaca     1440
cgcaatcctc ctactcgatt tccggtttgc agactgcctt gccaaatggc aactatgcgg     1500
attatctgtc agggctgttg gggggaacg ggatttccgt ttccaatgga agtgtcgctt      1560
cgttcacgct tgcgcctgga gccgtgtctg tttggcagta cagcacatcc gcttcagcgc     1620
cgcaaatcgg atcggttgct ccgaatatgg gaattccggg taatgtggtc acgatcgacg     1680
ggaaaggttt tggaacgacg cagggaaccg tgacatttgg cggagtgaca gcgactgtaa     1740
aatcctggac atcaaaccgg attgaagtgt acgtgcccaa catggccgcc ggtctgaccg     1800
atgtaaaagt caccgcgggt ggagtttcca gcaatctgta ttcttacaat attttgagtg     1860
gaacgcagac atcggttgtg tttactgtga aaagtgctcc tccgaccaac ctgggggata     1920
agatttacct gacgggcaac ataccggaat tgggaaattg gagcacggat acgagcggag     1980
ccgttaacaa tgcgcaaggg cccctgctcg cgcccaatta tccggattgg ttttatgtat     2040
tcagcgttcc ggcaggaaag acgattcaat tcaagttttt catcaagcgt gcggatggaa     2100
cgattcaatg ggagaatggt tcgaaccacg tggccacaac tcccacgggt gcaaccggta     2160
acatcactgt cacgtggcaa aactaataag tttaaac                              2197
```

<210> SEQ ID NO 7
<211> LENGTH: 686
<212> TYPE: PRT
<213> ORGANISM: Artificial Sequence
<220> FEATURE:
<223> OTHER INFORMATION: amino acid sequence of a variant of the
      Alicyclobacillus pohliae NCIMB14276 wild type alpha-amylase
      polypeptide

<400> SEQUENCE: 7

```
Ser Ser Ser Ala Ser Val Lys Gly Asp Val Ile Tyr Gln Ile Ile Ile
1               5                   10                  15

Asp Arg Phe Tyr Asp Gly Asp Thr Thr Asn Asn Asn Pro Ala Lys Ser
            20                  25                  30

Tyr Gly Leu Tyr Asp Pro Thr Lys Ser Lys Trp Lys Met Tyr Trp Gly
        35                  40                  45

Gly Asp Leu Glu Gly Val Arg Gln Lys Leu Pro Tyr Leu Lys Gln Leu
    50                  55                  60

Gly Val Thr Thr Ile Trp Leu Ser Pro Val Leu Asp Asn Leu Asp Thr
65                  70                  75                  80
```

```
Leu Ala Gly Thr Asp Asn Thr Gly Tyr His Gly Tyr Trp Thr Arg Asp
                85                  90                  95

Phe Lys Gln Ile Glu Glu His Phe Gly Asn Trp Thr Thr Phe Asp Thr
                100                 105                 110

Leu Val Asn Asp Ala His Gln Asn Gly Ile Lys Val Ile Val Asp Phe
                115                 120                 125

Val Pro Asn His Leu Thr Pro Phe Lys Ala Asn Asp Ser Thr Phe Ala
            130                 135                 140

Glu Gly Gly Ala Leu Tyr Asp Asn Gly Thr Tyr Met Gly Asn Tyr Phe
145                 150                 155                 160

Asp Asp Ala Thr Lys Gly Tyr Phe His His Asn Gly Asp Ile Ser Asn
                165                 170                 175

Trp Asp Asp Arg Tyr Glu Ala Gln Trp Lys Asn Phe Thr Asp Pro Ala
                180                 185                 190

Gly Phe Ser Leu Ala Asp Leu Ser Gln Glu Asn Gly Thr Ile Ala Gln
                195                 200                 205

Tyr Leu Thr Asp Ala Ala Val Gln Leu Val Ala His Gly Ala Asp Gly
            210                 215                 220

Leu Arg Ile Asp Ala Val Lys His Phe Asn Ser Gly Phe Ser Lys Ser
225                 230                 235                 240

Leu Ala Asp Lys Leu Tyr Gln Lys Lys Asp Ile Phe Leu Val Gly Glu
                245                 250                 255

Trp Tyr Gly Asp Asp Pro Gly Ala Ala Asn His Leu Glu Lys Val Arg
                260                 265                 270

Tyr Ala Asn Asn Ser Gly Val Asn Val Leu Asp Phe Asp Leu Asn Thr
                275                 280                 285

Val Ile Arg Asn Val Phe Gly Thr Phe Thr Gln Thr Met Tyr Asp Leu
            290                 295                 300

Asn Asn Met Val Asn Gln Thr Gly Asn Glu Tyr Lys Tyr Lys Glu Asn
305                 310                 315                 320

Leu Ile Thr Phe Ile Asp Asn His Asp Met Ser Arg Phe Leu Thr Val
                325                 330                 335

Asn Ser Asn Lys Ala Asn Leu His Gln Ala Leu Ala Phe Ile Leu Thr
                340                 345                 350

Ser Arg Gly Thr Pro Ser Ile Tyr Tyr Gly Thr Glu Gln Tyr Met Ala
            355                 360                 365

Gly Gly Asn Asp Pro Tyr Asn Arg Gly Met Met Pro Ala Phe Asp Thr
370                 375                 380

Thr Thr Thr Ala Phe Lys Glu Val Ser Thr Leu Ala Gly Leu Arg Arg
385                 390                 395                 400

Asn Asn Ala Ala Ile Gln Tyr Gly Thr Thr Gln Arg Trp Ile Asn
                405                 410                 415

Asn Asp Val Tyr Ile Tyr Glu Arg Lys Phe Phe Asn Asp Val Val Leu
                420                 425                 430

Val Ala Ile Asn Arg Asn Thr Gln Ser Ser Tyr Ser Ile Ser Gly Leu
            435                 440                 445

Gln Thr Ala Leu Pro Asn Gly Asn Tyr Ala Asp Tyr Leu Ser Gly Leu
450                 455                 460

Leu Gly Gly Asn Gly Ile Ser Val Ser Asn Gly Ser Val Ala Ser Phe
465                 470                 475                 480

Thr Leu Ala Pro Gly Ala Val Ser Val Trp Gln Tyr Ser Thr Ser Ala
                485                 490                 495
```

```
Ser Ala Pro Gln Ile Gly Ser Val Ala Pro Asn Met Gly Ile Pro Gly
            500                 505                 510

Asn Val Val Thr Ile Asp Gly Lys Gly Phe Gly Thr Thr Gln Gly Thr
            515                 520                 525

Val Thr Phe Gly Gly Val Thr Ala Thr Val Lys Ser Trp Thr Ser Asn
        530                 535                 540

Arg Ile Glu Val Tyr Val Pro Asn Met Ala Ala Gly Leu Thr Asp Val
545                 550                 555                 560

Lys Val Thr Ala Gly Gly Val Ser Ser Asn Leu Tyr Ser Tyr Asn Ile
                565                 570                 575

Leu Ser Gly Thr Gln Thr Ser Val Val Phe Thr Val Lys Ser Ala Pro
            580                 585                 590

Pro Thr Asn Leu Gly Asp Lys Ile Tyr Leu Thr Gly Asn Ile Pro Glu
            595                 600                 605

Leu Gly Asn Trp Ser Thr Asp Thr Ser Gly Ala Val Asn Asn Ala Gln
        610                 615                 620

Gly Pro Leu Leu Ala Pro Asn Tyr Pro Asp Trp Phe Tyr Val Phe Ser
625                 630                 635                 640

Val Pro Ala Gly Lys Thr Ile Gln Phe Lys Phe Ile Lys Arg Ala
                645                 650                 655

Asp Gly Thr Ile Gln Trp Glu Asn Gly Ser Asn His Val Ala Thr Thr
            660                 665                 670

Pro Thr Gly Ala Thr Gly Asn Ile Thr Val Thr Trp Gln Asn
            675                 680                 685

<210> SEQ ID NO 8
<211> LENGTH: 686
<212> TYPE: PRT
<213> ORGANISM: Artificial Sequence
<220> FEATURE:
<223> OTHER INFORMATION: amino acid sequence of a variant of the
      Alicyclobacillus pohliae NCIMB14276 wild type alpha-amylase
      polypeptide

<400> SEQUENCE: 8

Ser Ser Ser Ala Ser Val Lys Gly Asp Val Ile Tyr Gln Ile Ile
1               5                   10                  15

Asp Arg Phe Tyr Asp Gly Asp Thr Thr Asn Asn Asn Pro Ala Lys Ser
            20                  25                  30

Tyr Gly Leu Tyr Asp Pro Thr Lys Ser Lys Trp Lys Met Tyr Trp Gly
        35                  40                  45

Gly Asp Leu Glu Gly Val Arg Gln Lys Leu Pro Tyr Leu Lys Gln Leu
    50                  55                  60

Gly Val Thr Thr Ile Trp Leu Ser Pro Val Leu Asp Asn Leu Asp Thr
65                  70                  75                  80

Leu Ala Gly Thr Asp Asn Thr Gly Tyr His Gly Tyr Trp Thr Arg Asp
                85                  90                  95

Phe Lys Gln Ile Glu Glu His Phe Gly Asn Trp Thr Thr Phe Asp Thr
            100                 105                 110

Leu Val Asn Asp Ala His Gln Asn Gly Ile Lys Val Ile Val Asp Phe
        115                 120                 125

Val Pro Asn His Ser Thr Pro Phe Lys Ala Asn Asp Ser Thr Phe Ala
    130                 135                 140

Glu Gly Gly Ala Leu Tyr Asp Asn Gly Thr Tyr Met Gly Asn Tyr Phe
145                 150                 155                 160

Asp Asp Ala Thr Lys Gly Tyr Phe His His Asn Gly Asp Ile Ser Asn
```

-continued

```
                165                 170                 175
Trp Asp Asp Arg Tyr Glu Ala Gln Trp Lys Asn Phe Thr Asp Pro Ala
            180                 185                 190
Gly Phe Ser Leu Ala Asp Leu Ser Gln Glu Asn Gly Thr Ile Ala Gln
        195                 200                 205
Tyr Leu Thr Asp Ala Ala Val Gln Leu Val Ala His Gly Ala Asp Gly
    210                 215                 220
Leu Arg Ile Asp Ala Val Lys His Phe Asn Ser Gly Phe Ser Lys Ser
225                 230                 235                 240
Leu Ala Asp Lys Leu Tyr Gln Lys Lys Asp Ile Phe Leu Val Gly Glu
                245                 250                 255
Trp Tyr Gly Asp Asp Pro Gly Ala Ala Asn His Leu Glu Lys Val Arg
            260                 265                 270
Tyr Ala Asn Asn Ser Gly Val Asn Val Leu Asp Phe Asp Leu Asn Thr
        275                 280                 285
Val Ile Arg Asn Val Phe Gly Thr Phe Thr Gln Thr Met Tyr Asp Leu
    290                 295                 300
Asn Asn Met Val Asn Gln Thr Gly Asn Glu Tyr Lys Tyr Lys Glu Asn
305                 310                 315                 320
Leu Ile Thr Phe Ile Asp Asn His Asp Met Ser Arg Phe Leu Thr Val
                325                 330                 335
Asn Ser Asn Lys Ala Asn Leu His Gln Ala Leu Ala Phe Ile Leu Thr
            340                 345                 350
Ser Arg Gly Thr Pro Ser Ile Tyr Tyr Gly Thr Glu Gln Tyr Met Ala
        355                 360                 365
Gly Gly Asn Asp Pro Tyr Asn Arg Gly Met Met Pro Ala Phe Asp Thr
    370                 375                 380
Thr Thr Thr Ala Phe Lys Glu Val Ser Thr Leu Ala Gly Leu Arg Arg
385                 390                 395                 400
Asn Asn Ala Ala Ile Gln Tyr Gly Thr Thr Gln Arg Trp Ile Asn
                405                 410                 415
Asn Asp Val Tyr Ile Tyr Glu Arg Lys Phe Phe Asn Asp Val Val Leu
            420                 425                 430
Val Ala Ile Asn Arg Asn Thr Gln Ser Ser Tyr Ser Ile Ser Gly Leu
        435                 440                 445
Gln Thr Ala Leu Pro Asn Gly Asn Tyr Ala Asp Tyr Leu Ser Gly Leu
    450                 455                 460
Leu Gly Gly Asn Gly Ile Ser Val Ser Asn Gly Ser Val Ala Ser Phe
465                 470                 475                 480
Thr Leu Ala Pro Gly Ala Val Ser Val Trp Gln Tyr Ser Thr Ser Ala
                485                 490                 495
Ser Ala Pro Gln Ile Gly Ser Val Ala Pro Asn Met Gly Ile Pro Gly
            500                 505                 510
Asn Val Val Thr Ile Asp Gly Lys Gly Phe Gly Thr Thr Gln Gly Thr
        515                 520                 525
Val Thr Phe Gly Gly Val Thr Ala Thr Val Lys Ser Trp Thr Ser Asn
    530                 535                 540
Arg Ile Glu Val Tyr Val Pro Asn Met Gly Ala Gly Leu Thr Asp Val
545                 550                 555                 560
Lys Val Thr Ala Gly Gly Val Ser Ser Asn Leu Tyr Ser Tyr Asn Ile
                565                 570                 575
Leu Ser Gly Thr Gln Thr Ser Val Val Phe Thr Val Lys Ser Ala Pro
            580                 585                 590
```

```
                                        -continued
Pro Thr Asn Leu Gly Asp Lys Ile Tyr Leu Thr Gly Asn Ile Pro Glu
        595                 600                 605

Leu Gly Asn Trp Ser Thr Asp Thr Ser Gly Ala Val Asn Asn Ala Gln
    610                 615                 620

Gly Pro Leu Leu Ala Pro Asn Tyr Pro Asp Trp Phe Tyr Val Phe Ser
625                 630                 635                 640

Val Pro Ala Gly Lys Thr Ile Gln Phe Lys Phe Phe Ile Lys Arg Ala
                645                 650                 655

Asp Gly Thr Ile Gln Trp Glu Asn Gly Ser Asn His Val Ala Thr Thr
            660                 665                 670

Pro Thr Gly Ala Thr Gly Asn Ile Thr Val Thr Trp Gln Asn
        675                 680                 685
```